United States Patent
Sachs et al.

(10) Patent No.: US 11,284,947 B2
(45) Date of Patent: Mar. 29, 2022

(54) DEVICES AND METHODS FOR ROBOTIC ASSEMBLIES

(71) Applicant: Vicarious Surgical Inc., Charlestown, MA (US)

(72) Inventors: Adam Sachs, Somerville, MA (US); Eric Van Albert, Cambridge, MA (US); Sammy Khalifa, Medford, MA (US); Robert White, Jr., Charlestown, MA (US); Ryan Fish, Allston, MA (US); Eric Kline, Malden, MA (US); Marshall Wentworth, Somerville, MA (US)

(73) Assignee: VICARIOUS SURGICAL INC., Charlestown, MA (US)

( * ) Notice: Subject to any disclaimer, the term of this patent is extended or adjusted under 35 U.S.C. 154(b) by 0 days.

(21) Appl. No.: 17/236,906

(22) Filed: Apr. 21, 2021

(65) Prior Publication Data

US 2021/0290314 A1    Sep. 23, 2021

Related U.S. Application Data

(63) Continuation of application No. PCT/US2020/039203, filed on Jun. 23, 2020.
(Continued)

(51) Int. Cl.
*A61B 34/20* (2016.01)
*A61B 34/30* (2016.01)
(Continued)

(52) U.S. Cl.
CPC .............. *A61B 34/20* (2016.02); *A61B 17/34* (2013.01); *A61B 34/30* (2016.02); *A61B 34/71* (2016.02);
(Continued)

(58) Field of Classification Search
CPC ......... A61B 34/20; A61B 17/34; A61B 34/71; A61B 34/30; A61B 90/361;
(Continued)

(56) References Cited

U.S. PATENT DOCUMENTS 9,066,737 B2    6/2015  Barwinkel et al.
10,285,765 B2   5/2019  Sachs et al.
(Continued)

FOREIGN PATENT DOCUMENTS

WO    WO-2019094896 A1    5/2019

OTHER PUBLICATIONS

PCT/US2020/039203 International Search Report and Written Opinion dated Nov. 19, 2020.

*Primary Examiner* — Richard G Louis
(74) *Attorney, Agent, or Firm* — Wilson Sonsini Goodrich & Rosati

(57) ABSTRACT

Disclosed herein are methods, devices and systems for performing robotic procedures. The devices may include one or more robotic arms. The one or more robotic arms may comprise one or more joints. A joint may include a magnetic sensing system. The one or more robotic arms may be configured to move an elbow joint independently from an end effector or origin of the robotic arm. A working end of the robotic arm may be configured for insertion through a trocar into a body cavity of a subject and may be operatively coupled to a motor unit by one or more electrical or mechanical components housed in a support tube.

30 Claims, 61 Drawing Sheets

Related U.S. Application Data

(60) Provisional application No. 62/912,910, filed on Oct. 9, 2019, provisional application No. 62/882,921, filed on Aug. 5, 2019, provisional application No. 62/877,141, filed on Jul. 22, 2019, provisional application No. 62/865,658, filed on Jun. 24, 2019.

(51) Int. Cl.
| | | |
|---|---|---|
| *A61B 17/34* | (2006.01) | |
| *B25J 9/06* | (2006.01) | |
| *A61B 90/00* | (2016.01) | |
| *A61B 34/00* | (2016.01) | |
| *A61B 17/00* | (2006.01) | |

(52) U.S. Cl.
CPC ............... *A61B 90/361* (2016.02); *B25J 9/06* (2013.01); *A61B 2017/00292* (2013.01); *A61B 2034/2051* (2016.02); *A61B 2034/2059* (2016.02); *A61B 2034/302* (2016.02)

(58) Field of Classification Search
CPC .. A61B 2034/2059; A61B 2017/00292; A61B 2034/302; A61B 2034/2051; A61B 2017/00738; A61B 17/3421; B25J 9/06
See application file for complete search history.

(56) References Cited

U.S. PATENT DOCUMENTS

| | | | |
|---|---|---|---|
| 2008/0064921 A1* | 3/2008 | Larkin | A61B 1/04 600/104 |
| 2011/0282351 A1* | 11/2011 | Cooper | A61B 34/70 606/108 |
| 2017/0014998 A1 | 1/2017 | Langenfeld et al. | |
| 2017/0020615 A1 | 1/2017 | Koenig et al. | |
| 2017/0291297 A1 | 10/2017 | Miyasaka | |
| 2019/0076199 A1 | 3/2019 | Kline et al. | |
| 2019/0142531 A1 | 5/2019 | Wentworth et al. | |

* cited by examiner

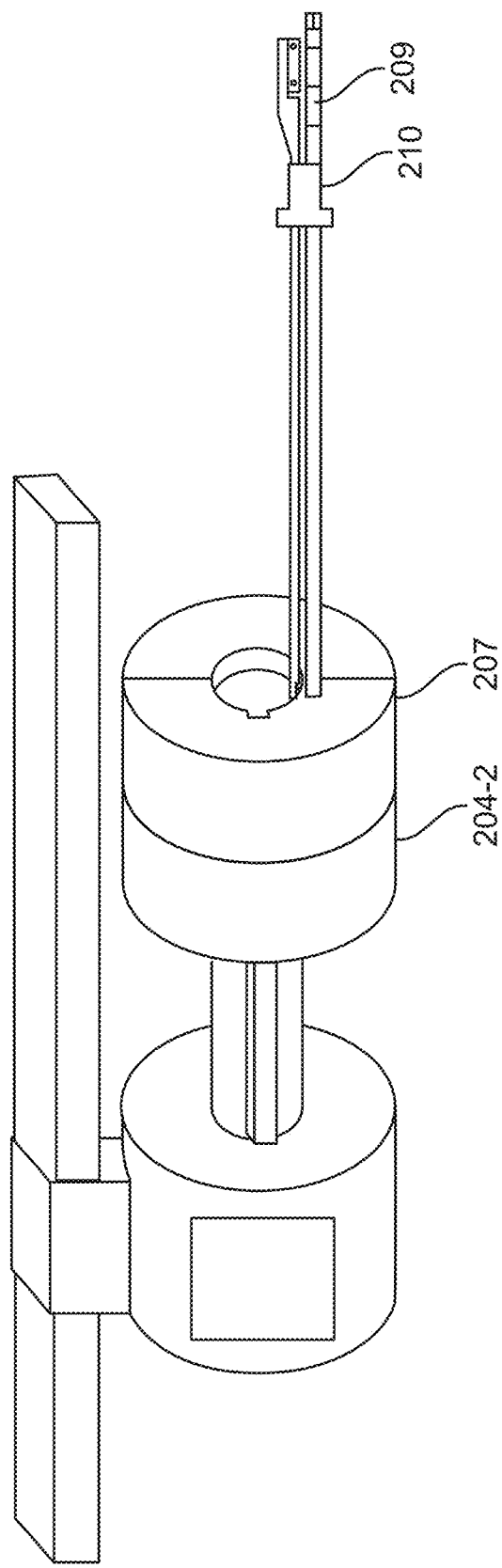

DEVICES AND METHODS FOR ROBOTIC ASSEMBLIES

CROSS-REFERENCE

This application is a continuation of International Application Number PCT/US2020/039203, filed on Jun. 23, 2020, which claims the benefit of U.S. Provisional Application Ser. No. 62/865,658 filed on Jun. 24, 2019, U.S. Provisional Application Ser. No. 62/877,141 filed on Jul. 22, 2019, U.S. Provisional Ser. No. 62/882,921 filed on Aug. 5, 2019, and U.S. Provisional Application Ser. No. 62/912,910 filed on Oct. 9, 2019, the entirety of which are hereby incorporated by reference herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Described herein is a robotic arm comprising: a plurality of joints sequentially coupled from an origin of the robotic arm to an end effector of the robotic arm to form: (i) a first section of the robotic arm comprising the origin, (ii) a second section of the robotic arm comprising a robotic elbow joint, (iii) a third section of the robotic arm comprising the end effector, wherein a joint positioned within the first section and a joint positioned within the third section permits movement of at least a portion of the second section independently from a movement of the origin or the end effector of the robotic arm. In some embodiments, the robotic elbow joint comprises a hinge joint. In some embodiments, the plurality of joints comprise a hinge joint, a rotary joint, or a combination thereof. In some embodiments, the joint positioned within the first section comprises a hinge joint. In some embodiments, the joint positioned within the third section comprises a hinge joint. In some embodiments, the joint positioned within the first section and the joint positioned within the third section permit movement of at least a portion of the second section independent from movement of the origin and the end effector. In some embodiments, the end effector comprises a surgical tool. In some embodiments, the plurality of joints comprises at least 3 hinge joints. In some embodiments, the plurality of joints comprises at least 3 rotary joints. In some embodiments, a movement of a joint is performed by a motor unit. In some embodiments, a displacement of a joint is measured by a magnetic sensing system. In some embodiments, the magnetic sensing system is positioned within a portion of the joint. In some embodiments, a positioning of the plurality of joints to form the robotic arm permits a range of movement of the robotic arm having at least 8 degrees of freedom. In some embodiments, a size of the robotic arm is configured for placement within a body cavity. In some embodiments, the plurality of joints comprise a section of joints positioned with an alternating pattern of a hinge joint and a rotary joint. In some embodiments, the end effector is directly coupled to a hinge joint. In some embodiments, a hinge joint is configured for rotation motion about an axis perpendicular to a lengthwise axis of the robotic arm. In some embodiments, a rotary joint is configured for motion about a lengthwise axis of the robotic arm. In some embodiments, a hinge joint is configured for movement along a singular plane. In some embodiments, the robotic arm comprises a surgical robotic assembly comprising a support tube configured to couple with the robotic arm and deliver the robotic arm through a trocar so that at least a portion of the robotic arm deflects outward when the portion of the robotic arm exits the trocar.

Described herein is a method comprising: inserting through a trocar a plurality of working ends of a robot assembly, wherein a support tube operatively couples a corresponding working end of the plurality with a portion of the robot assembly that is positioned outside of the trocar; and inserting at least a portion of the support tube into the trocar, wherein as the corresponding working end exits from the trocar, at least a portion of the support tube moves radially outward towards a portion of an inner wall of the trocar. In some embodiments, a transition element is coupled to the corresponding working end. In some embodiments, a proximal end of the transition element guides the corresponding working end radially outward upon exiting the trocar. In some embodiments, a stiffness of the support tube drives the support tube radially outward. In some embodiments, the support tube is coupled to an elastic element, and wherein the elastic element drives the support tube radially outward. In some embodiments, the elastic element comprises a spring. In some embodiments, the plurality of working ends comprise at least two of: a working end of a camera, a working end of a first robotic arm, and a working end of a second robotic arm. In some embodiments, the plurality of working ends comprise the working end of a camera, the working end of the first robotic arm, and the working end of the second robotic arm. In some embodiments, at least a portion of the proximal end of the transition element comprises a side that is curved along at least a portion of its length. In some embodiments, at least a portion of the distal end of the transition element comprises a tapered end. In some embodiments, the inserting of the plurality of working ends is sequential. In some embodiments, an order of the inserting of the plurality of working ends is based at least in part on a relative cross-sectional area of each of the plurality of working ends. In some embodiments, the inserting comprises individually inserting each of the plurality of working ends into the trocar. In some embodiments, the inserting is performed by one or more motor units coupled to the robotic assembly. In some embodiments, the one or more motor units comprise a motor, a drivetrain, an electronics, or any combination thereof. In some embodiments, the one or more motor units comprises a mounting member configured to translate the motor unit substantially parallel to an axis of insertion of the plurality of working ends. In some embodiments, each working end of the plurality of working ends is coupled to a corresponding motor unit. In some embodiments, the support tube comprises a mechanical power element, an electrical power element, or a combination thereof. In some embodiments, the trocar maintains insufflation of a body cavity as one or more working ends are inserted through the trocar into the body cavity. In some embodiments, the method further comprises positioning the working end of the camera between the working end of the first robotic arm and the working end of the second robotic arm. In some embodiments, the working end of camera is positioned substantially equidistance between the working end of the first robotic arm and the working end of the second robotic arm. In some embodiments, the positioning is performed by one or more motor units. In some embodiments, the camera comprises a stereoscopic camera. In some embodiments, a portion of the robot assembly is coupled to the trocar. In some embodiments, the method further comprises removing the plurality of working ends by re-entering the trocar. In some embodiments, the transition element guides a working end radially inward upon re-entry to the trocar. In some embodiments, the method further comprises independently adjusting a relative depth of a working end of the plurality.

Described herein is a robotic joint comprising a magnetic sensing system, wherein the magnetic sensing system comprises: (a) an arrangement of magnets that form a magnetic field; and (b) an arrangement of sensors configured to measure a change in at least a portion of the magnetic field, wherein the change corresponds to a displacement of the robotic joint. In some embodiments, the arrangement of magnets comprises two or more magnets forming substantially a magnetic column. In some embodiments, the two or more magnets are positioned with a dipole arrangement of N-S, N-S or S-N, S-N. In some embodiments, the arrangement of magnets comprises a first magnetic column and a second magnetic column. In some embodiments, a magnetization direction of a magnet of the first magnetic column has an opposite dipole arrangement of a magnet of the second magnetic column. In some embodiments, a magnetization direction of a magnet of the first magnetic column has a same dipole arrangement as a magnet of the second magnetic column. In some embodiments, the arrangement sensors are positioned on or near a plane substantially perpendicular to the arrangement of magnets. In some embodiments, the plane that is substantially perpendicular is positioned between first magnet and a second magnet, wherein the first and second magnet form a column of magnets. In some embodiments, the arrangement of magnets and arrangement of sensors is positioned substantially proximal a peripheral edge of the robotic joint. In some embodiments, the magnetic sensing system measures the displacement of the robotic joint with a higher resolution as compared to a comparable robotic joint lacking the arrangement of magnets and the arrangement of sensors. In some embodiments, the arrangement of magnets comprises a set of magnets positioned in separate spatial quadrants of the magnetic sensing system. In some embodiments, a first magnet of the set comprises a magnetization direction aligned with a second magnet in a diagonally positioned quadrant. In some embodiments, a first magnet of a column is positioned within a first quadrant and a second magnet of the column is positioned with a second quadrant. In some embodiments, the magnetic field comprises an orthogonal field component, a parallel field component, a non-parallel field component, or any combination thereof. In some embodiments, a magnet of the plurality of magnets comprise neodymium, iron, or any combination thereof. In some embodiments, a magnet of the plurality of magnetics comprises an electromagnet. In some embodiments, the robotic arm comprises a cable-driven robotic arm. In some embodiments, the arrangement of magnets comprises at least 4 magnets. In some embodiments, the arrangement of sensors comprises an array of sensors. In some embodiments, the array of sensors comprises at least 2 sensors. In some embodiments, a robotic arm comprising the robotic joint. In some embodiments, each of the plurality of robotic joints comprises the robotic joint.

Described herein is a robotic arm comprising a joint, wherein the joint comprises: a portion of an electrical communication component, wherein the portion is associated with a first portion and a second portion of the joint and: (a) is wrapped around an axis of the joint, wherein a number of wraps of the portion varies proportionally to a motion of the joint; or (b) is extended to form a moving bend, wherein during actuation of the joint, the moving bend moves relative to the first portion and the second portion. In some embodiments, the portion is extended to form the moving bend, and wherein the moving bend is positioned and moves within a channel of a housing of the joint. In some embodiments, the channel is positioned outside of a central axis of the joint. In some embodiments, at a first range of motion of the joint, a minimum amount of the moving bend is positioned within the channel and at a second range of motion of the joint, a maximum amount of the moving bend is positioned within the channel. In some embodiments, the robotic arm comprises a pin. In some embodiments, a portion of the joint is operatively configured as a cam and the pin is operatively configured as a cam follower. In some embodiments, the robotic arm comprises an elastic element coupled to the electrical component. In some embodiments, the elastic element comprises a spring or an elastic band. In some embodiments, the elastic element comprises the spring that is a constant force spring. In some embodiments, the portion is wrapped around the axis of the joint, and wherein the joint comprises a rotary joint. In some embodiments, the portion is extended to form the moving bend, and wherein the joint comprises a hinge joint. In some embodiments, association with the first position of the joint, the second position of the joint, or a combination thereof are fixed. In some embodiments, the portion is wrapped around the axis of the joint to at least partially form a helical coil. In some embodiments, the portion is wrapped around the axis of the joint, and wherein the number of wraps are positioned between a housing and a shaft of the joint. In some embodiments, at a first range of motion of the joint, the number of wraps are maximized and the portion is wrapped around the shaft, and at a second range of motion of the joint, the number of wraps are minimized and the portion is expanded against the housing. In some embodiments, the electrical communication component operatively couples an end effector of a robotic arm with a control system. In some embodiments, the electrical communication component is configured to transmit one or more electrical signals to or from a portion of the robotic arm. In some embodiments, the portion is configured to move with respect to a motion of the joint. In some embodiments, during movement of the joint, the portion is configured to substantially maintain a radius of curvature. In some embodiments, the robotic arm comprises a stopping element to limit a range of motion of the robotic arm. In some embodiments, the robotic arm comprises a coating or a film that covers at least a portion of the electrical communication component. In some embodiments, the coating or the film comprises a lubricant.

BRIEF DESCRIPTION OF THE DRAWINGS

This patent application contains at least one drawing executed in color. Copies of this patent or patent application with color drawing(s) will be provided by the Office upon request and payment of the necessary fee.

FIGS. 2-9 and 10A-10K illustrate a surgical robot split arm architecture, in accordance with some embodiments.

The novel features of the disclosure are set forth with particularity in the appended claims. A better understanding of the features and advantages of the present disclosure will be obtained by reference to the following detailed description that sets forth illustrative embodiments.

DETAILED DESCRIPTION

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Any systems, methods, software, and platforms described herein are modular and not limited to sequential steps. Accordingly, terms such as "first" and "second" do not necessarily imply priority, order of importance, or order of acts.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

Figure 40:
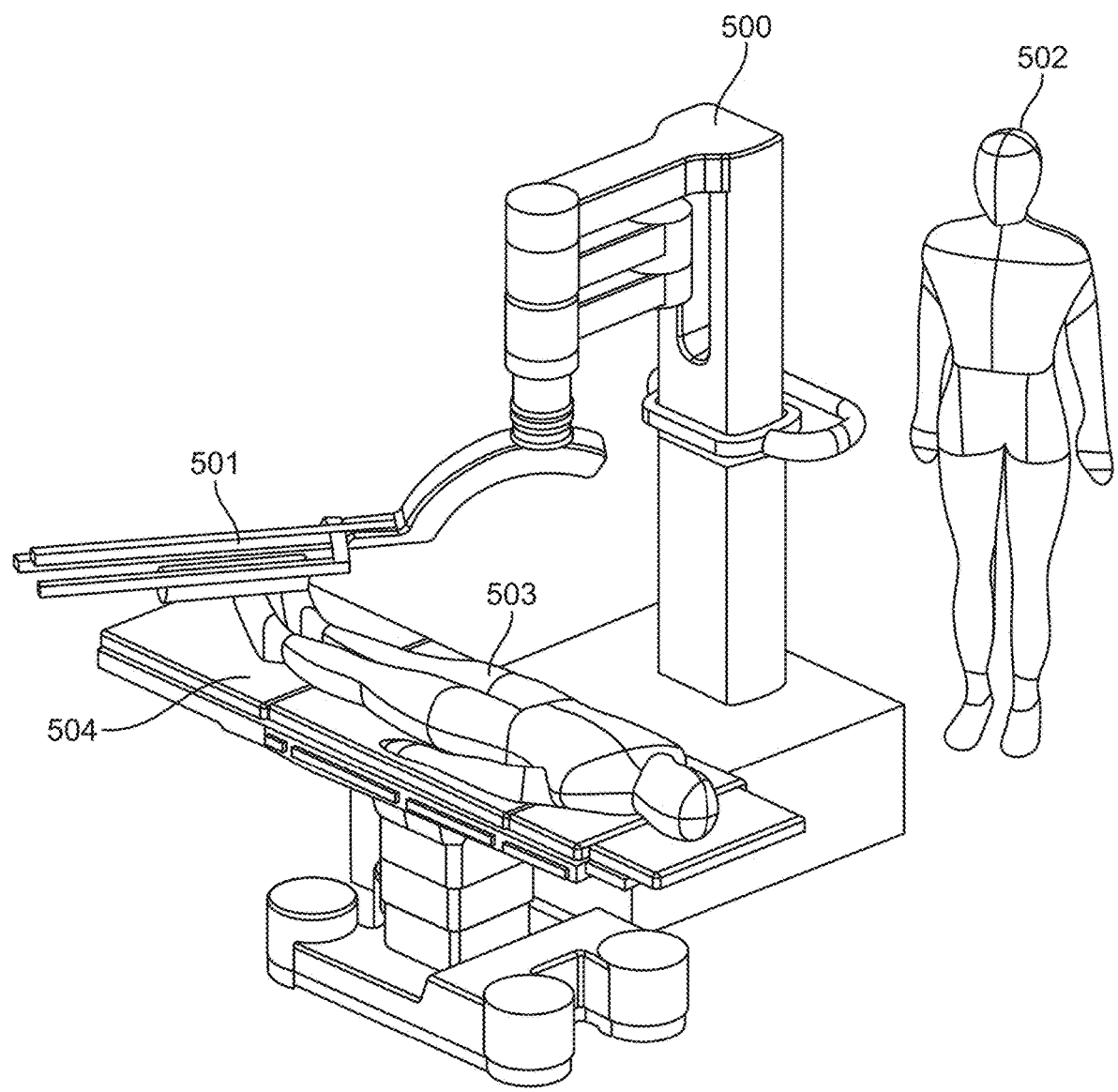
FIGS. 40-42 illustrate a robotic assembly positioned relative to a patient receiving a surgical procedure and a medical professional performing the surgical procedure with the assistance of the robotic assembly.
Figure 41:
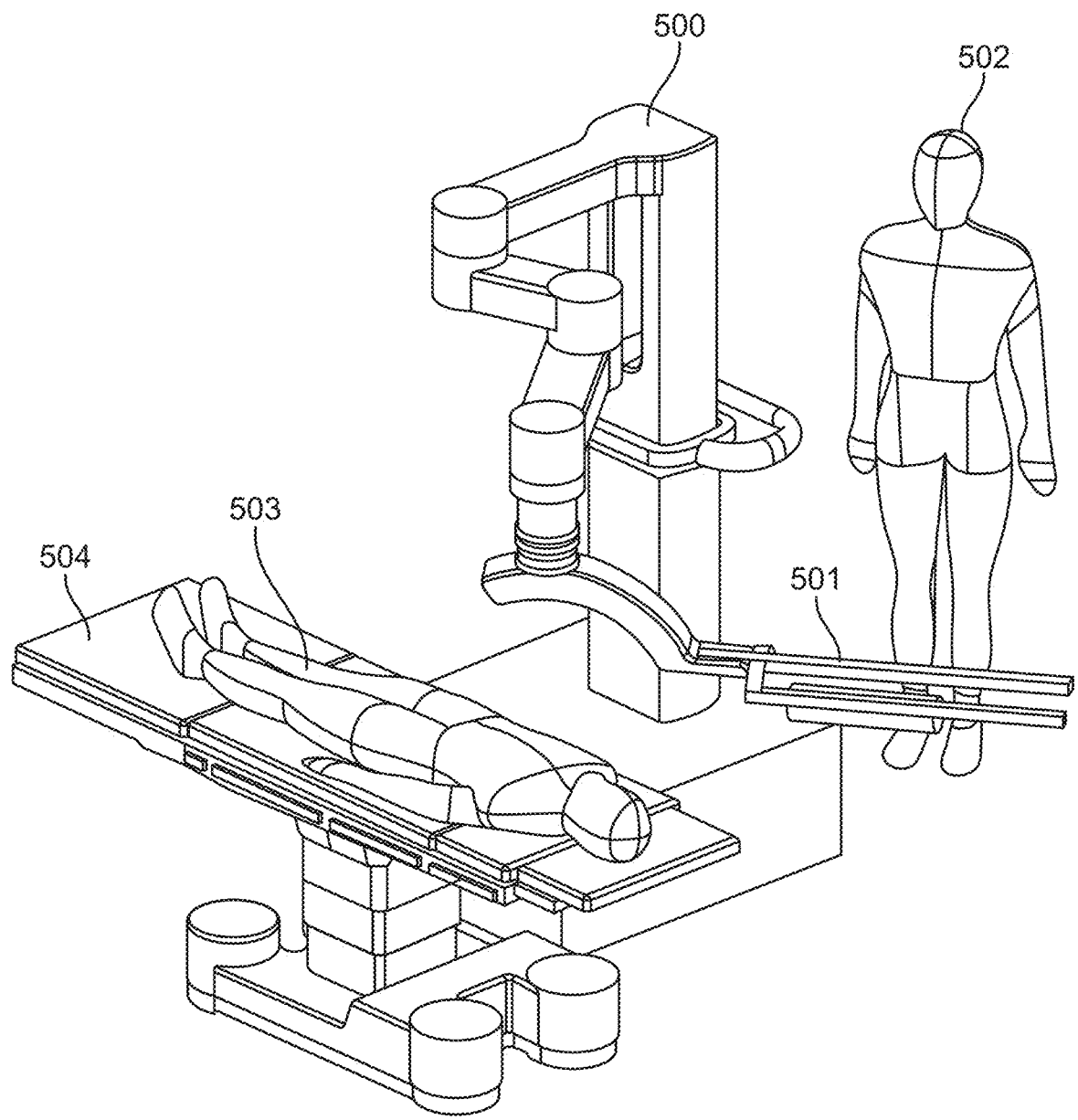
Figure 42:
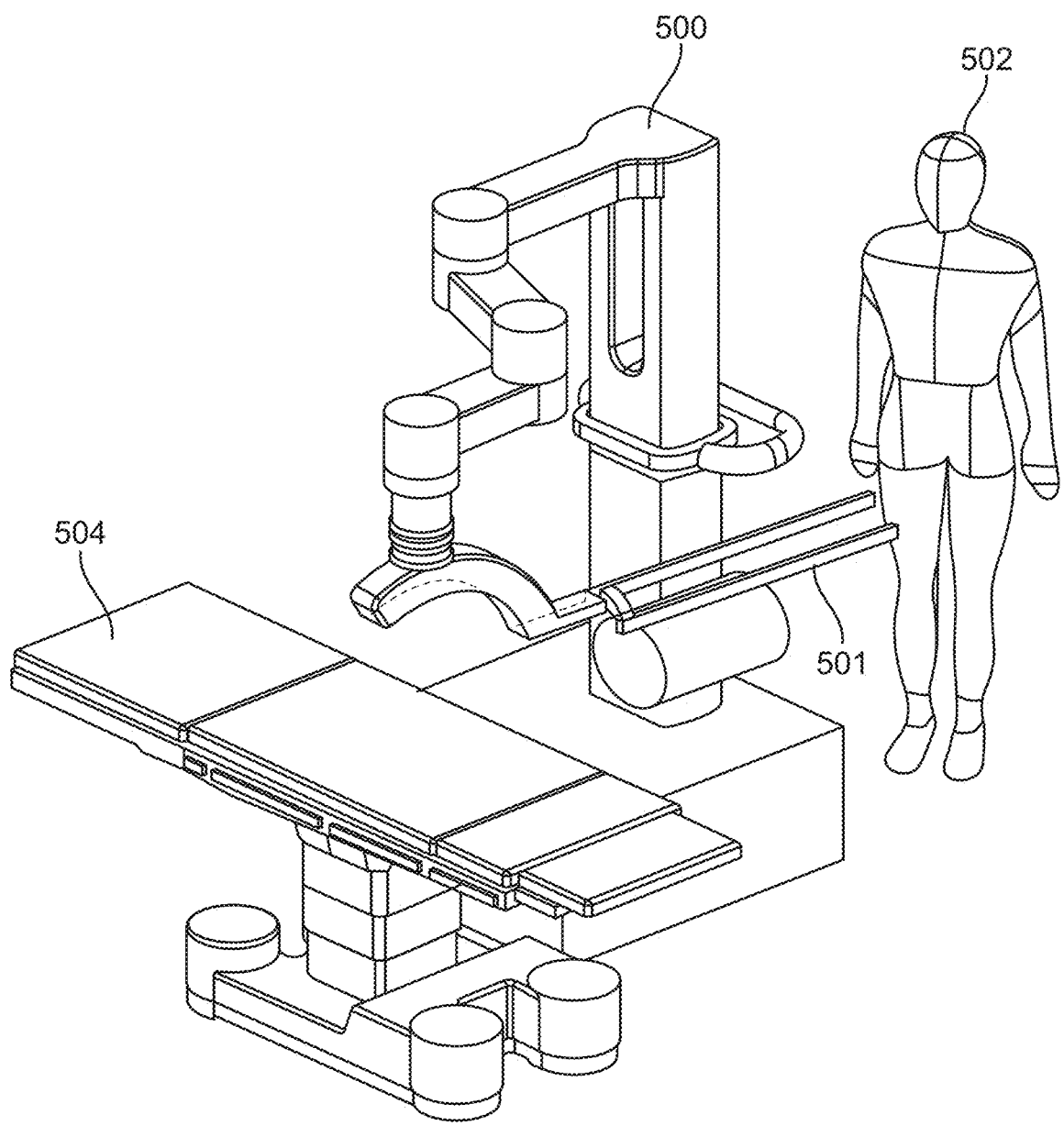

As shown in the sequence of images of FIG. 40-42, a surgical procedure may be performed by a medical professional 502 (such as a surgeon) on a patient 503 with the assistance of a robotic machine 500 having a robotic assembly 501. At least a portion of the robotic assembly 501 may be inserted in a portion of the patient 503. At least a portion of the robotic assembly 501 may remain outside of the patient 503. The portion that may be inserted may include a camera and two robotic arms. The portion that may remain outside of the patient 503 may include motor units, rails, portions of support tubes, control systems, and others. The patient 503 may be positioned on a surface 504, such as an operating table. The robotic assembly 501 may be movable. The robotic assembly 501 may be positioned over an area of a patient. The surgical procedure may include inserting a portion of the robotic assembly 501 into a portion of the patient 503, in some cases, through one or more trocars. The surgical procedure may include a therapeutic procedure, a diagnostic procedure, a prophylactic procedure, a theranostic procedure or any combination thereof.

A robotic assembly may comprise one or more magnets, such as a magnetic sensing system of a robotic assembly. The magnetic sensing system may be positioned within a portion of the robotic assembly, such as a joint. One or more joints of a robotic assembly may comprise a magnetic sensing system, comprising one or more magnets. A magnetic field of one or more magnets may change as a result of a displacement or movement of a portion of the robotic assembly, such as a joint. A corresponding one or more sensors may be configured to measure the change in the magnetic field. A magnet of the magnetic sensing system may be a ring magnet, a circular magnet, a bar magnet, a horse shoe magnet, a ball magnet, a cylindrical magnet, or any combination thereof. A magnet or portion thereof may be a ceramic magnet. A magnet or portion thereof may comprise neodymium, boran, iron, or any combination thereof. A magnet or portion thereof may comprise neodymium, ferrite, rubber, iron, lodestone, magnetite, or any combination thereof. A magnet or portion thereof may comprise NdFeB. A magnet or portion thereof may comprise a magnetic strength from about N33 to N52. A magnet may comprise a magnetic strength of about N35. A magnet may comprise a magnetic strength of about N42. A magnet or portion thereof may comprise a magnetic strength from about Y10 to Y30BH. A magnet or portion thereof may be an isotropic magnet, A magnet or portion thereof may be an anisotropic magnet. A magnet or portion thereof may comprise a rubber magnet. A magnet or portion thereof may comprise ferrite, AlNiCo (AN), SmCo (SC), NdFeB (ND), or any combination thereof. A magnet or portion thereof may comprise an electromagnet.

A robotic assembly may comprise one or more sensors. A magnetic sensing system of a robotic assembly may comprise one or more sensors. The sensors may be positioned within a portion of the robotic assembly, such as a joint. One or more joints of a robotic assembly may comprise a magnetic sensing system, comprising one or more sensors. A sensor may be configured to measure a change in a portion of a magnetic field of one or more magnets that corresponds to a displacement or movement of a portion of the robotic assembly, such as the joint. A sensor may be configured to measure a change in a portion of a magnetic field. A sensor may comprise a search-coil magnetometer, a flux-gate magnetometer, an optically pumped magnetometer, a nuclear-procession magnetometer, a SQUID magnetometer, a Hall-Effect sensor, a magnetoresistive magnetometer, a magnetodiode, a magnetotransistor, a fiber-optic magnetometer, a magneto-optical sensor, or any combination thereof.

A robotic assembly may comprise 1, 2, 3, 4, 5, 6, 7, 8, 9, 10, 11, 12, 13, 14, 15, 20, 25, 30, 35, 40, 45, 50, 75, 100, 150, 200 sensors or more. A joint of a robotic assembly may comprise 1, 2, 3, 4, 5, 6, 7, 8, 9, 10 sensors or more. A joint may comprise from about 1 to about 10 sensors. A joint may comprise from about 1 to about 8 sensors. A joint may comprise from about 1 to about 6 sensors. A joint may comprise from about 2 to about 8 sensors. A joint may comprise from about 2 to about 6 sensors. A joint or other component of a robotic assembly may comprise an even number of sensors or an odd number of sensors. A joint may comprise 2, 4, 6, 8, 10 sensors or more. A joint may comprise 1, 3, 5, 7, 9 sensors or more. One or more sensors may form an arrangement of sensors. An arrangement may comprise an arrangement that positions sensors substantially to a periphery of a component of the robotic assembly, such as a joint. An arrangement can comprise one or more sensors along a same axis or within a given plane. One or more sensors may form an array of sensors. An array of sensors may comprise 2×2 sensors, 3×3 sensors, 4×4 sensors, 2×3 sensors, 2×4 sensors, 3×4 sensors, or other combinations.

A robotic assembly may comprise a plurality of joints. At least two joints of the plurality of joints may be of a same type. At least two joints of the plurality of joints may be of a different type. A robotic arm of the robotic assembly may comprise a plurality of joints. A joint may be configured for translational motion, configured for rotary motion, or any combination thereof. A robotic assembly may comprise a joint configured for translational motion, a joint configured for rotary motion, or a combination thereof. A joint may be a linear joint, an orthogonal joint, a rotational joint, a twisting joint, or a revolving joint. A robotic assembly may comprise a linear joint, an orthogonal joint, a rotational joint, a twisting joint, a revolving joint, or any combination thereof. A joint may comprise a hinge joint or a rotary joint. A robotic assembly may comprise a hinge joint, a rotary joint, or a combination thereof.

A robotic assembly may comprise 1, 2, 3, 4, 5, 6, 7, 8, 9, 10, 15, 20 joints or more. A robotic assembly may comprise at least about 2, 3, 4, 5, 6, 7, 8, 9, 10, 15, 20 joints or more. A robotic arm may comprise 1, 2, 3, 4, 5, 6, 7, 8, 9, 10, 15, 20 joints or more. A robotic arm may comprise at least about 2, 3, 4, 5, 6, 7, 8, 9, 10, 15, 20 joints or more. A robotic assembly may comprise one or more hinge joints. A robotic assembly may comprise one or more rotary joints. A robotic arm of a robotic assembly may comprise one or more hinge joints, one or more rotary joints, or a combination thereof. A robotic arm may comprise from about 1 to 10 hinge joints, from about 1 to 10 rotary joints, or a combination thereof. A robotic arm may comprise from about 2 to 15 hinge joints, 2 to 15 rotary joints, or a combination thereof. A portion of a robotic arm may comprise an alternating pattern of hinge joints and rotary joints. A portion of a robotic arm may comprise a repeating pattern of hinge joints or a repeating pattern of rotary joints. A pattern of joints may be configured such that the robotic arm moves with at least 7 degrees of freedom, with at least 8 degrees of freedom, or more.

A robotic assembly may include a robotic arm. A robotic assembly may include more than one robotic arm. At least a portion of the robotic arm may be configured to enter and execute tasks within a body cavity of a subject. A robotic arm may comprise an end effector. The end effector may be coupled to a distal end of the robotic arm. A robotic arm may comprise more than one end effector, such as 2, 3, or more end effectors. An end effector may be coupled and de-coupled from a robotic arm. An end effector of a first robotic arm may be a different type as an end effector of a second robotic arm of the robotic assembly. An end effector of a first robotic arm may be a same type as an end effector of a second robotic arm of the robotic assembly. An end effector may comprise a forceps, a needle, a scalpel, a clamp, a scissors, a hook, a retractor, a clamp, a suction tool, a stapler, a cystoscope, a saw (such as a bone saw), an arthroscope, an energy tool (such as an electrocautery tool, an ultrasonic tool, or an endostapler), or any combination thereof.

A robotic assembly may include one or more working ends. A robotic assembly may comprise 1, 2, 3, 4, 5, 6, 7, 8, 9, 10 working ends or more. A robotic assembly may comprise at least 2, 3, 4, 5, 6, 7, 8, 9, 10 working ends or more. A working end may be a portion of a robotic assembly that enters a body cavity. A working end may comprise a camera, a robotic arm comprising an end effector, or other robotic component. A working end may be inserted through a trocar to enter the body cavity. In some cases, 1, 2, 3, 4, 5, 6, 7, 8, 9, 10 working ends or more may be inserted through a trocar. In some cases, at least about 2, 3, 4, 5, 6, 7, 8, 9, 10 working ends may be inserted through a trocar. In some cases, a subset of working ends may be inserted into a body cavity by passing through a first trocar and a second subset of working ends may be inserted into the body cavity by passing through a second trocar. In some cases, a robotic assembly comprises 3 working ends that pass through a single trocar.

A robotic assembly may comprise an elastic element. The elastic element may be configured to be operatively connected to or embedded within a working end of the robotic assembly (such as a working end of a robotic arm or a working end of the camera), a transition element, a support tube, a motor unit or any combination thereof. A working end of the robotic assembly may be operatively coupled to a corresponding elastic element. Each working end of the robotic assembly may be operative coupled to a corresponding elastic element. The elastic element may cause an outward bias of working ends inserted into a trocar such that a connect support tube is drive radially outward to a position adjacent to an inner wall of the trocar. The elastic element may comprise a spring or elastic band or rubber band. A spring may comprise a compression spring, an extension spring, a torsion spring, a constant force spring, or any combination thereof. A spring may comprise a flat spring, a spiral spring, a helical spring, a disc spring, a tubular spring, a membrane, an aneroid box, a bellow, or any combination thereof.

A robotic assembly or portion thereof as described herein may comprise one or more coatings. For example, electrical components of a robotic arm of the robotic assembly may be coated with a coating. The coating may comprise a conformal coating. A coating or portion thereof may be polymer-based, such as an amorphous fluoropolymer. A coating or portion thereof may comprise an acrylic resin, a silicone resin, a urethane resin, an epoxy resin, a parylene, a silicone, or any combination thereof. A coating or portion thereof may comprise a nano-coating, a thin film coating, or a combination thereof.

Robotic Arms—Range of Movement

Previous generations of surgical robotics arms generally have no more than seven degrees of freedom, including the end effector. In fact, many surgical robots operate with fewer than seven degrees of freedom. Seven degrees of freedom, in most instances, allows the user to both position and orient the end effector of the robot/surgical tool in a range of positions or orientations within a work space (seven degrees of freedom=x, y, z, yaw, pitch, roll, end effector open/close). However, there is typically only one permissible position for each joint of the robot for each position and orientation of the end effector. For example, the elbow of the robot can typically only be in one place for a given position and orientation of the end effector.

Seven degrees of freedom is insufficient for certain surgical procedures. A human arm has additional degrees of freedom that permit a human to move his or her elbow while keeping the shoulder and hand stationary. With more than seven degrees of freedom, a human arm is able to move/rotate the elbow to various positions (e.g., up and down) while keeping the hand in the same place. For certain surgical procedures, the choice of approach path is important. For example, the choice is important for open surgeries where surgeons need to keep their arm and elbow above the patient to prevent collision with the patient's abdominal contents. In some instances, choosing the approach path of a surgical robot is also important in non-robotic surgeries.

By incorporating eight degrees of freedom, the disclosed robotic arm is able to execute certain approach paths not available for robotic arms with only seven degrees of freedom (e.g., reaching up toward the ceiling of the abdomen (ventral wall) and operate). In some embodiments, the robot can reach around tissue and approach any organ from the back, just like a human can pick up a coffee mug from the back without rotating the mug. This is impossible with the existing technology including, e.g., the Intuitive Surgical Da Vinci robot. According to some embodiments, the disclosed robotic arm enables a surgeon to choose a more ideal approach path and approach any tissue from almost any angle.

A robotic assembly, such as a surgical robotic assembly, may comprise a robotic arm. In some cases, a robotic arm comprises a plurality of joints. The plurality of joints can be arranged sequentially from an origin of the robotic arm to an end effector of the robotic arm. The plurality of joints may form one or more sections, such as a plurality of sections. In some cases, a first section of the robotic arm may comprise the origin, such as a shoulder of the robotic arm. A second section of the robotic arm may comprise a robotic elbow joint. A third section of the robotic arm may comprise an end effector (such as a surgical tool). The robotic arm may comprise a joint positioned within the first section (such as a hinge joint) and a joint positioned with the third section (such as a hinge joint) to provide movement of at least a portion of the second section independently from a movement of the origin or the end effector of the robotic arm. In some cases, a combination of a joint positioned within the first section and a joint positioned within the third section permit movement of at least a portion of the second section independent from movement of the origin and the end effector. The robotic elbow joint may be a hinge joint, to mimic a human elbow. The plurality of joints of the robotic arm may comprise any combination of different types of joints, such as a hinge joint, a rotary joint, or a combination thereof. The plurality of joints of the robotic arm may comprise at least 3 hinge joints, at least 3 rotary joints, or a combination thereof. Positioning of the plurality of joints to form the robotic arm, such as an arrangement of joints or a pattern of joints. A portion of the robotic arm may comprise a section of joints positioned with an alternating pattern of a hinge joint and a rotary joint. An end effector may be coupled to a hinge joint. The positioning of the plurality of joints may permit a range of movement of the robotic arm. The range of movement of the robotic arm may comprise at least 7 degrees of freedom, at least 8 degrees of freedom, or more. The range of movement of the robotic arm may be substantially similar to a human arm. A size of the robotic arm may be configured for placement through a trocar and into a body cavity.

A hinge joint may be configured for rotational motion about an axis substantially perpendicular to a lengthwise axis of the robotic arm. A hinge joint may be configured for movement along a singular plane. A rotary joint may be configured for a parallel motion about an axis substantially lengthwise of the robotic arm.

Movement of one or more joints of the robotic arm may be performed by a motor unit. A joint of the plurality of joints may be operatively coupled to a corresponding motor unit. Each joint of the plurality of joints may be operatively coupled to a corresponding motor unit. Displacement of one or more of the plurality of joints may be measured by a magnetic sensing system. The robotic arm may comprise a magnetic sensing system. A joint of the plurality of joints may comprise a corresponding motor unit. Each joint of the plurality of joints may comprise a magnetic sensing system.

A magnetic sensing system may be positioned within a portion of a joint of the robotic arm.

Figure 1:
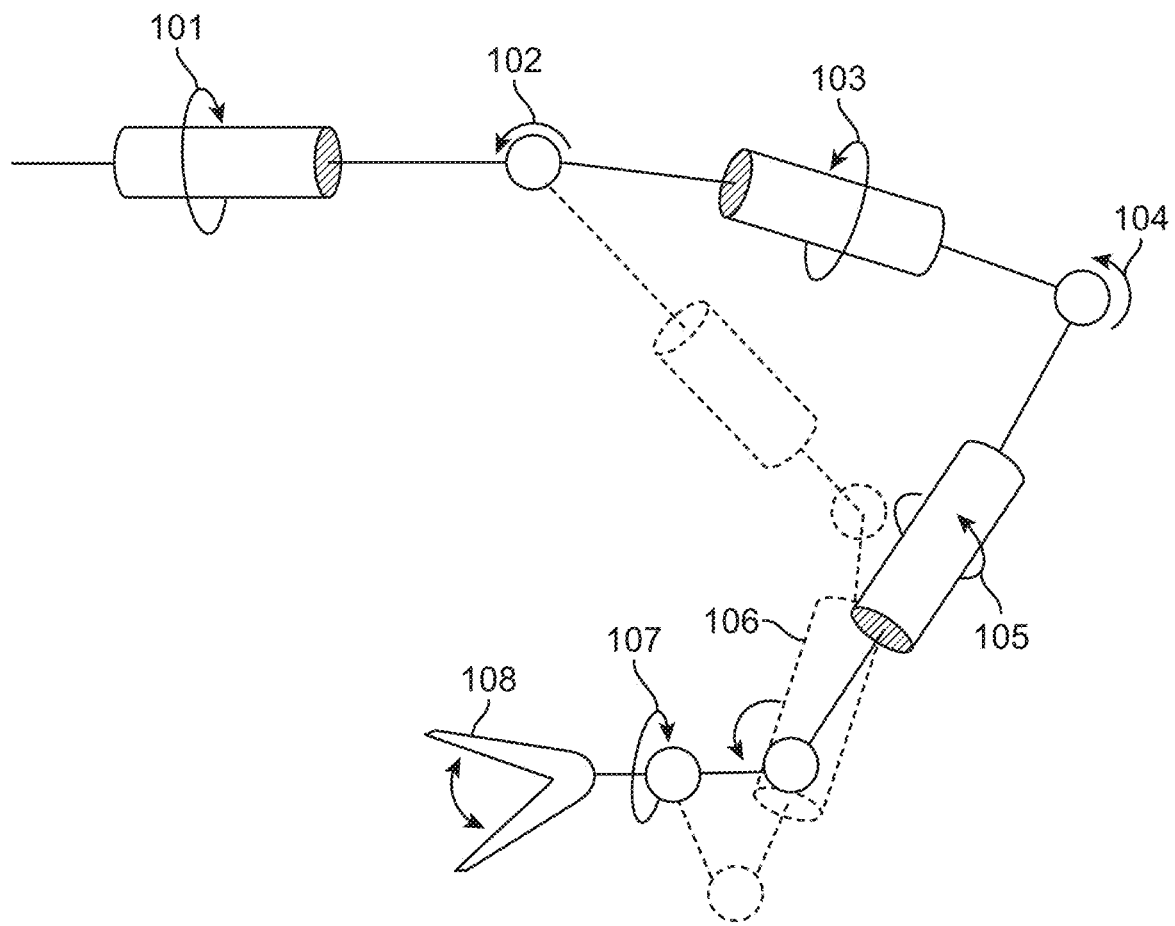
FIG. 1 illustrates a robotic arm comprising a plurality of joints, in accordance with some embodiments.

FIG. 1 illustrates a surgical robot according certain embodiments of the invention. The arm of the robot has the same configuration as a human arm. That is, the robot can drop its elbow and operate on the ceiling of the abdomen while keeping the end effector in the same position and orientation. As shown in FIG. 1, the configuration of the robot is (from the shoulder and in order): a first rotary joint 101, a first hinge joint 102, a second rotary joint 103, a second hinge joint 104, a third rotary joint 105, a third hinge joint 106, a fourth hinge joint 107, and an end effector 108. In some embodiments, the hinge joints 102, 104, 106, and 107 are defined as having rotational motion in an axis perpendicular to the lengthwise axis of the arm. In some embodiments, the rotary joints 101, 103, and 105 are defined as having motion parallel to the lengthwise axis of the arm.

According to certain embodiments, a range of motions based on these eight degrees of freedom can be achieved entirely within the abdominal cavity or bodily cavity in a human-like orientation. In some embodiments, a range of motions can be achieved with any number of degrees of freedom outside of the abdominal cavity. In some instances, similar to a Da Vinci-like robot, a motion based on four degrees of freedom can be achieved outside of the incision site.

According to certain embodiments, various suitable robotic actuators or other surgical robotic technologies including flexible robotics can be used with the disclosed system. According to some embodiments, the surgical apparatus system of FIG. 1 incorporates specialized actuators disclosed in U.S. Pat. No. 10,285,765 B2 titled Virtual Reality Surgical Device, and/or in United States Patent Application Publication 2019/0142531 A1 titled Virtual Reality Wrist Assembly, both references are attached in the appendix and are herein incorporated in their entirety.

Referring back to FIG. 1, the solid and dotted lines depict two exemplary configurations/positions of the robot arm. Notably, the elbow (at the second hinge joint 104) can move into various positions without moving/adjusting the end effector or the origin of the arm (e.g., shoulder).

Insertion of a Plurality of Working Ends Through a Trocar

The Individual Surgical Robot Arm Architecture also referred herein as the Split Arm Architecture, is a system that is designed to simplify and increase efficiency of the insertion of surgical instruments through a trocar, deployment of said surgical instruments into a surgical ready state, as well as the subsequent removal of said surgical instruments through that trocar. As an example, a surgical instrument may be inserted through a trocar to access and perform an operation on the abdominal cavity of a patient. In some embodiments, various surgical instruments may be utilized, including but not limited to robotic surgical instruments, as well as other surgical instruments known in the art.

A cross sectional area of a trocar is limited in space. Inserting multiple working ends of a robotic arm through a limited space can be challenging. Additionally, working ends are coupled to support tubes carrying electrical and mechanical components to operatively connect the working ends to motor units and other large components that remain outside of the body cavity. As such, as least a portion of each support tube remained in a portion of the trocar. A benefit of the current design permits, by adding an element to each inserted component that bias the working end radially outward and biases the corresponding support tube against in inner wall of the trocar, multiple working ends to pass through the trocar and into a body cavity.

Methods as described herein may including inserting a working end of a robot assembly through a trocar and into a body cavity. Methods may include inserting plurality working ends of a robot assembly through a trocar and into a body cavity of a subject. The cross-sectional area of an inner lumen of the trocar may be limited such that insertion of multiple working ends may be optimized. Additionally, one or more working ends may be operatively coupled to a corresponding support tube that operatively couples a working end to a portion of the robot assembly (such as a motor unit) that is not inserted through the trocar. At least a portion of the support tube (operatively coupling the working end to, for example, a motor unit) may remain inside of the trocar. Therefore, optimizing spatial distribution of a support tube within an inner lumen of the trocar may be important for accommodating multiple working ends and corresponding support tubes.

Methods as described herein may include inserting through a trocar a plurality of working ends of a robot assembly. For example, 1, 2, 3, 4, 5, 6, 7, 8 working ends or more may be inserted through a single trocar. At least a portion of the working ends may be inserted sequentially. An order of insertion may be determined based on a comparison of cross-sectional area of each of the plurality of working ends. At least a portion of the working ends may be inserted simultaneously. A support tube may be operatively coupled to a corresponding working end of the plurality of working ends with a portion of the robot assembly that is positioned outside of the trocar—such as a motor unit or control system. Methods may include inserting at least a portion of the support tube into the trocar. The portion of the support tube that enters the trocar may be drawn in by movement of the working end to which it is coupled. The portion of the support tube that enters the trocar may be drawn in as the corresponding working end exits from the trocar (such as into a body cavity of a subject). At least a portion of the support tube may move radially outward towards a portion of an inner wall of the trocar as the corresponding working end exits the trocar.

A transition element may be coupled to a working end. A transition element may be coupled to a distal end of the working end. For example, a working end may comprise a camera and the transition element may be coupled to the distal end opposite from the end that comprises the camera. The working end may comprise a transition element. The transition element may operatively couple the working end to a corresponding support tube. A portion of the transition element (such as a curved edge or tapering) may guide the working end radially outward upon exiting the trocar.

The working end may be operatively coupled to a corresponding support tube. The support tube may facilitate connections between the working end and a portion of the robot assembly that is not inserted into the trocar, such as a motor unit that drives the working end but may not be inserted into the trocar. A property of robot assembly (for example, the support tube, the transition element or a combination thereof) may provide for a radially outward bias, a radially outward force, or a deflection such that the working end after passing through the trocar is forced radially outward. This property of the robot assembly may also cause the portion of the support tube that remains in the trocar to move substantially adjacent to an inner wall of the trocar. A support tube comprises a mechanical power element, an electrical power element, or a combination thereof.

The property to provide the radially outward force may include stiffness of the support tube, the transition element or a combination thereof. The stiffness may be modified by adjusting a wall thickness of the support tube or transition element, a material composition of the support tube or transition element, a shape or length of the support tube or transition element, or any combination thereof. The property may include incorporating a hinge, such as a hinge on a motor unit or support tube. The property may include incorporating an elastic element in the robot assembly, such as a spring. The property to provide for a radially outward bias may include an attachment (such as a reversible attachment) between the support tube and the trocar.

A plurality of working ends may be inserted into a trocar. For example, a camera working end (such as for a stereoscopic camera), a working end of a first robotic arm and a working end of a second robotic arm may be inserted into the trocar. Insertion may be manual insertion by a user. Insertion may be performed with assistance of a motor unit. A relative depth of a working end may be independently adjusted, without further movement to the remaining working ends. A working end may be operatively coupled to a corresponding motor unit. Each working end may be individually coupled to a corresponding motor unit. Motor units may operative independently from one another. A motor unit may comprise a motor, a drivetrain, an electronics component, a control system, or any combination thereof. A motor unit may comprise a mounting member configured to translate the motor unit substantially parallel to an axis of insertion of the plurality of working ends.

A portion of the robot assembly may be coupled to the trocar. In some cases, a portion of the support tube may be coupled to the trocar. In some cases, a rail of the robotic assembly may be coupled to the trocar. The coupling may be reversible.

One or more working ends may be removed from a body cavity by re-entering the trocar. Re-entry of the working ends may be sequential or simultaneous. Initially, re-entry may include moving the support tube away from an inner wall of the trocar or overcoming the radially outward bias such that the working end can re-enter the trocar substantially through a central point of the cross-section area of the trocar. The transition element (such as a shape of the transition element) may guide the working end radially inward to re-enter the trocar.

Figure 2:
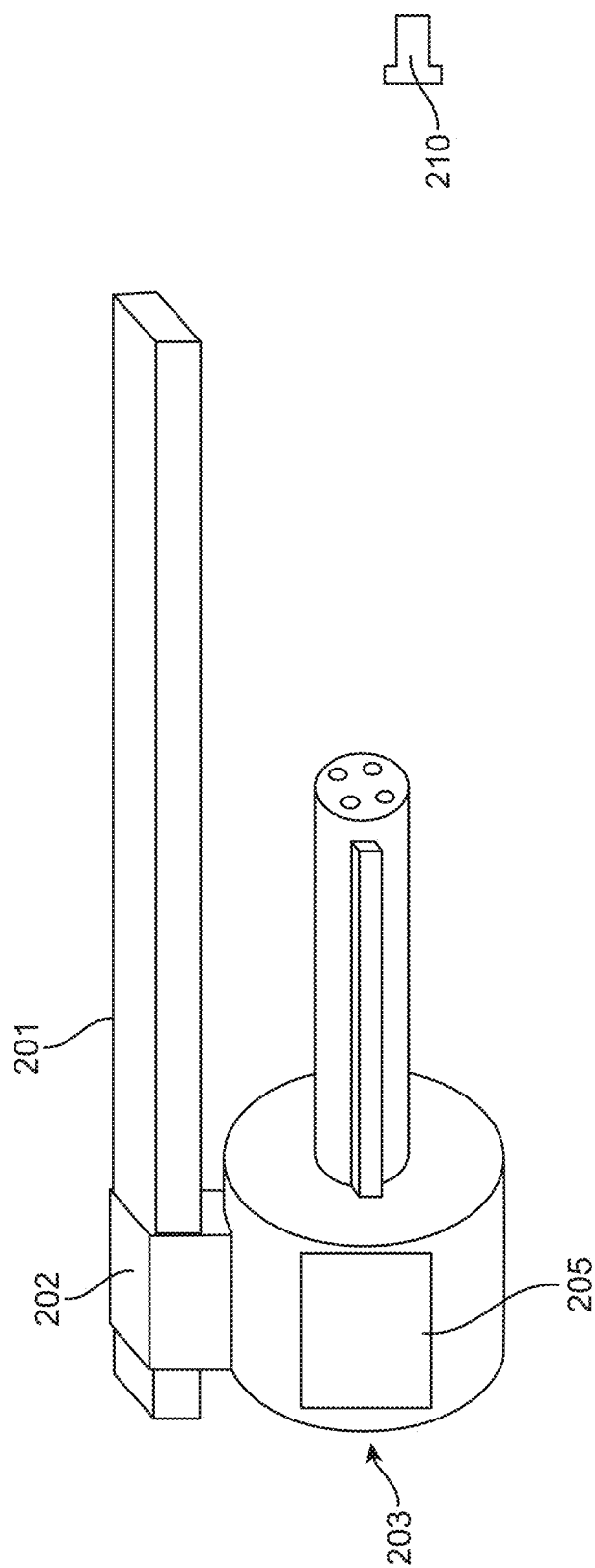
Figure 3:
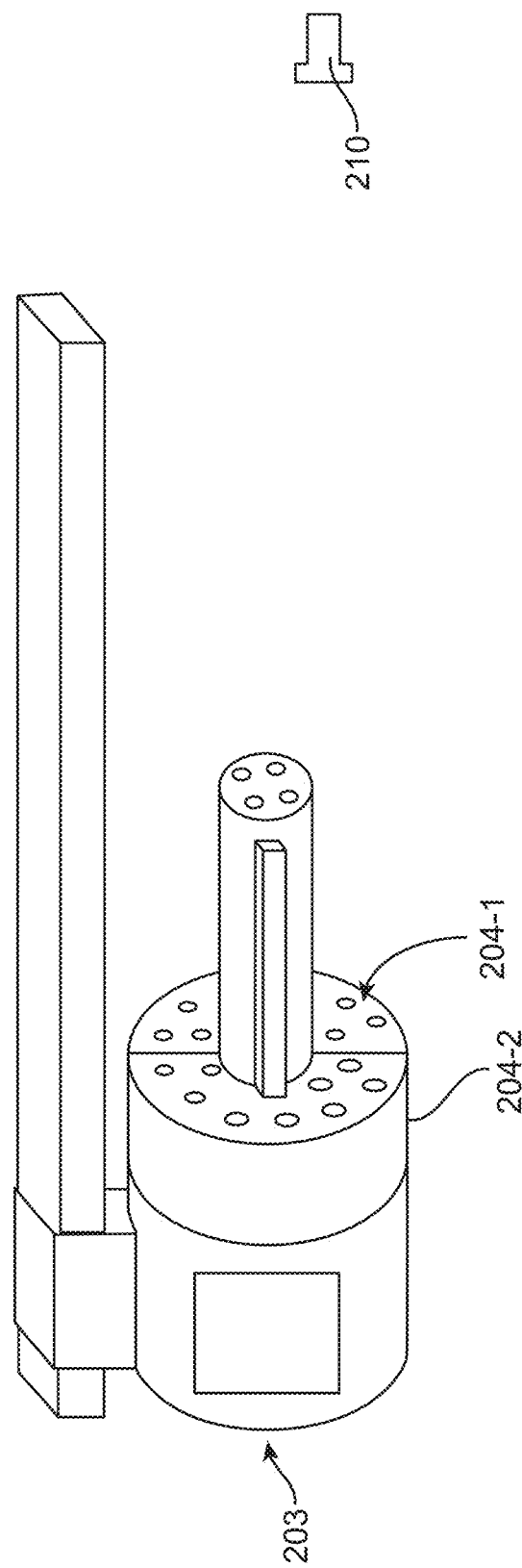
Figure 10A:
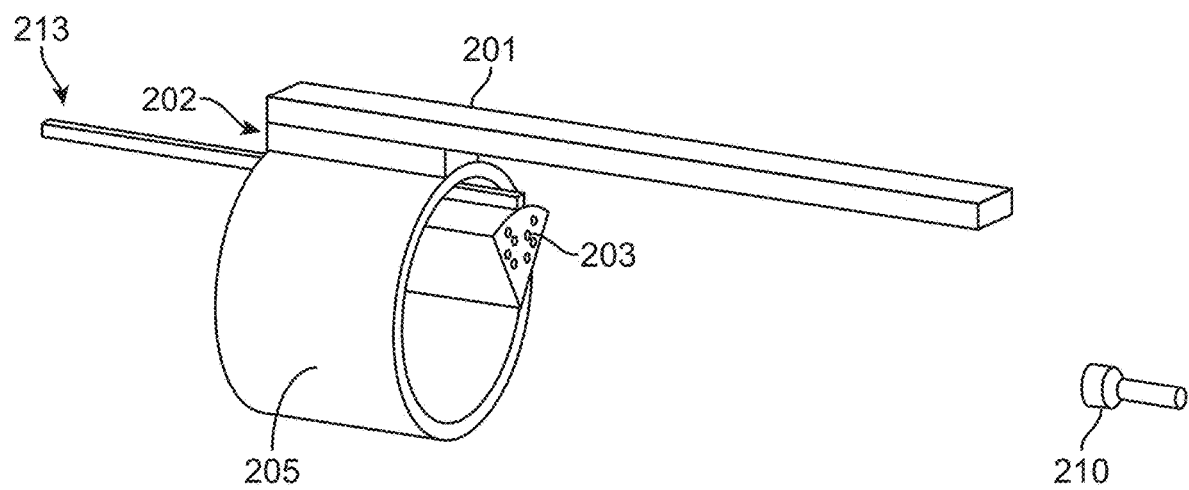

In some embodiments, the system is supported by a structure with several degrees of freedom such that the structure can be maneuvered over the patient into a position suitable for using the system. In some embodiments, the structure may be directly mounted to a surgical table or to the floor or ceiling. In some embodiments, the mounting is achieved by various fastening means, including but not limited to clamps, screws, or a combination thereof. In some embodiments, the structure may be free standing. The structure is referred to herein as the robot support system (RSS), as illustrated in FIG. 2 and FIG. 10A In some embodiments, the system comprises two segments. The first segment is permanently coupled to the RSS and has multiple moveable bodies, each is called a motor unit (MU). In some embodiments, the multiple moveable bodies may comprise a camera MU 203, a first arm MU 204-1 and a second arm MU 204-2 as shown in FIG. 3 and also FIG. 10B. The second segment, which can be coupled and decoupled from the first segment at will, is called a robot assembly. In some embodiments, the system is made of three (3) robot assemblies; a camera robot assembly and two (2) arm robot assemblies. In some embodiments, the system comprises more than three (3) robot assemblies. In some embodiments, the system comprises less than three (3) robot assemblies.

In some embodiments, the motor unit (MU) houses the motors, drivetrain, and electronics may be required to control the working end of a robot assembly. The MU is electrically coupled to a greater electrical system such that each MU is provided with the appropriate power and communication channels to be operated. In some embodiments, the MU comprises one or more mounting member, MU electronics housing, and MU engagement element.

A camera MU may comprise a centrally located element, such as shown in FIG. 2. A camera MU may comprise a wedge, such as shown in FIG. 10A. The housing 205 can comprise a roll cage. The housing 205 can provide rotational motion or a track or channel within the housing 205 can provide rotation motion.

Figure 10B:
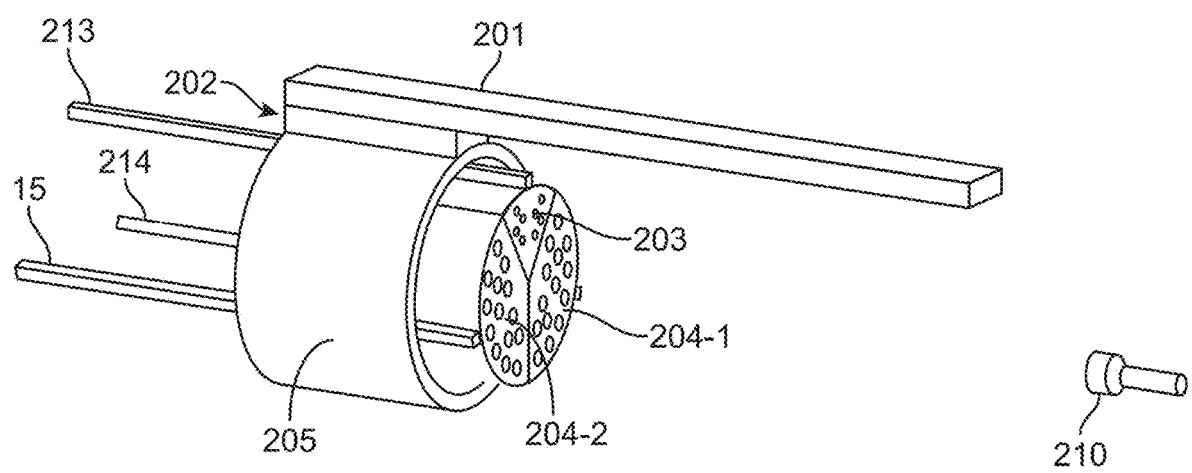
Figure 10C:
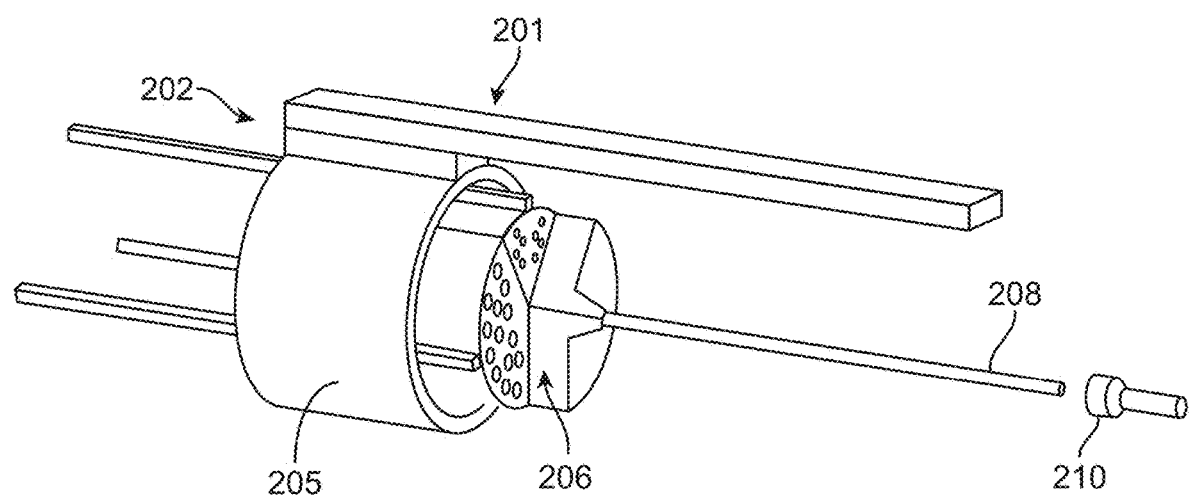
Figure 10D:
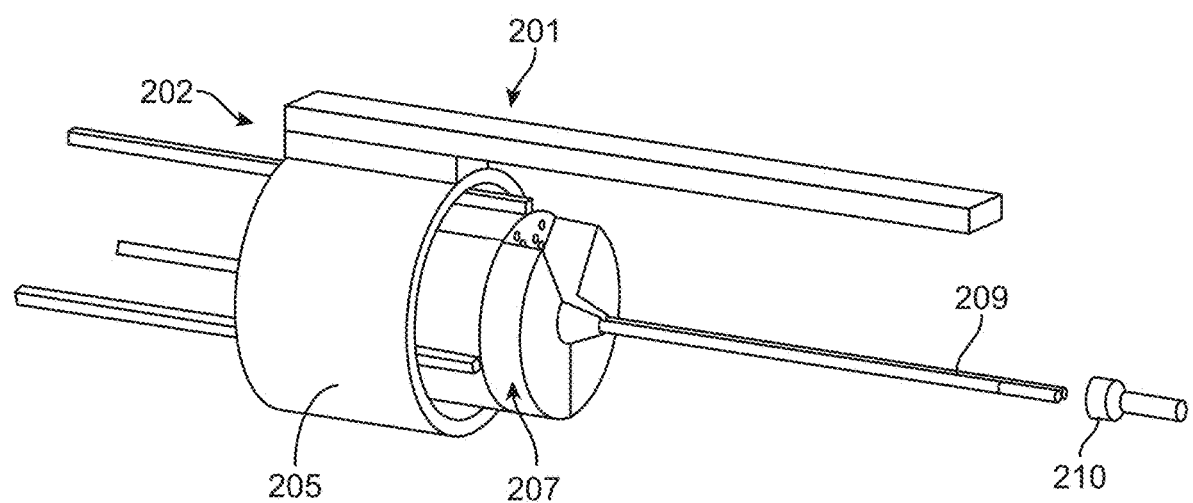
Figure 10E:
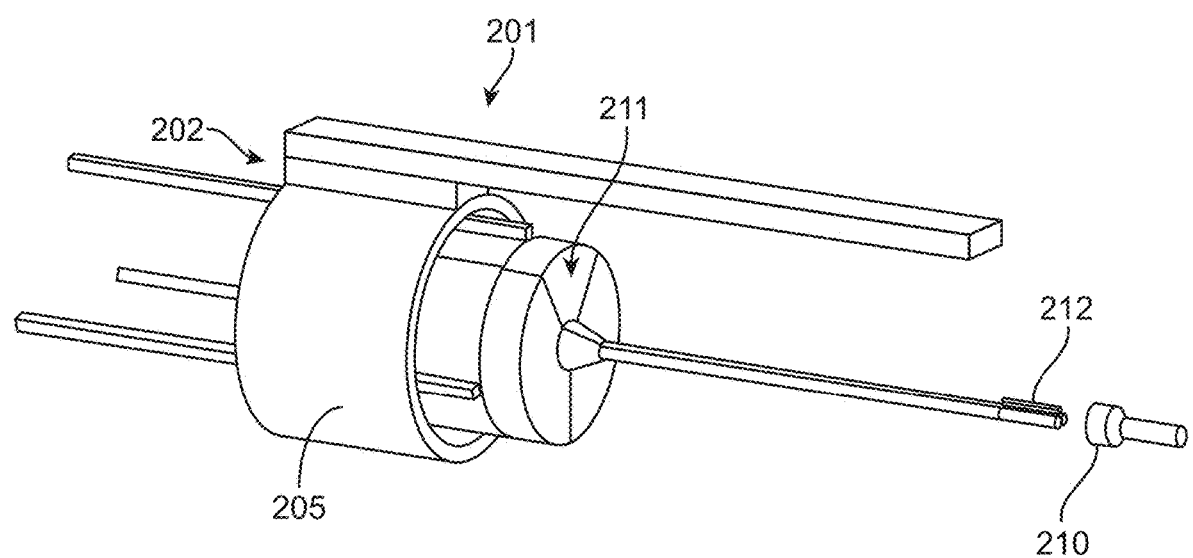
Figure 10F:
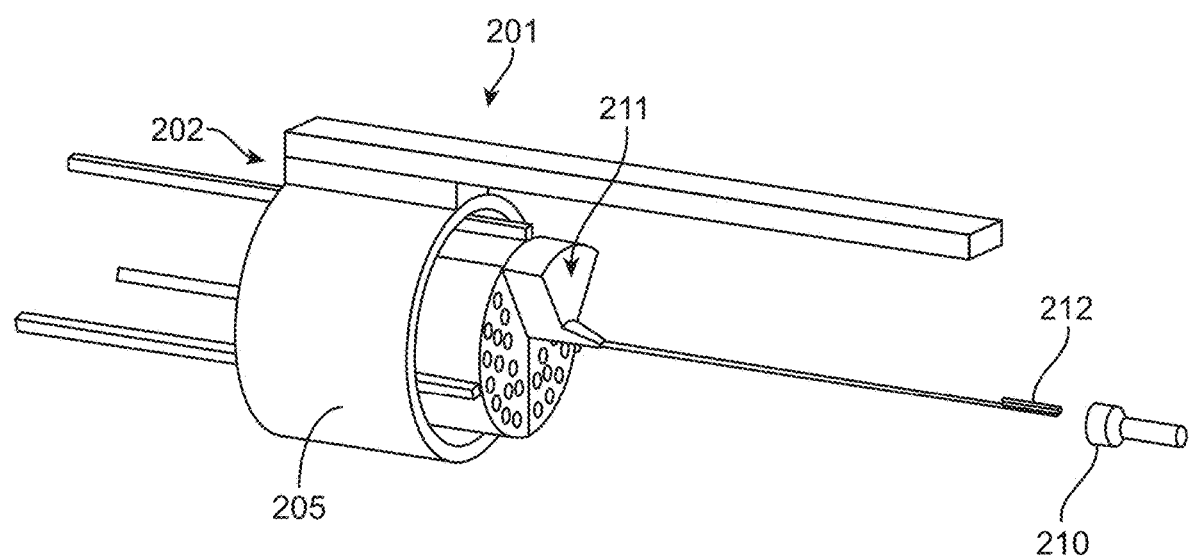
Figure 10G:
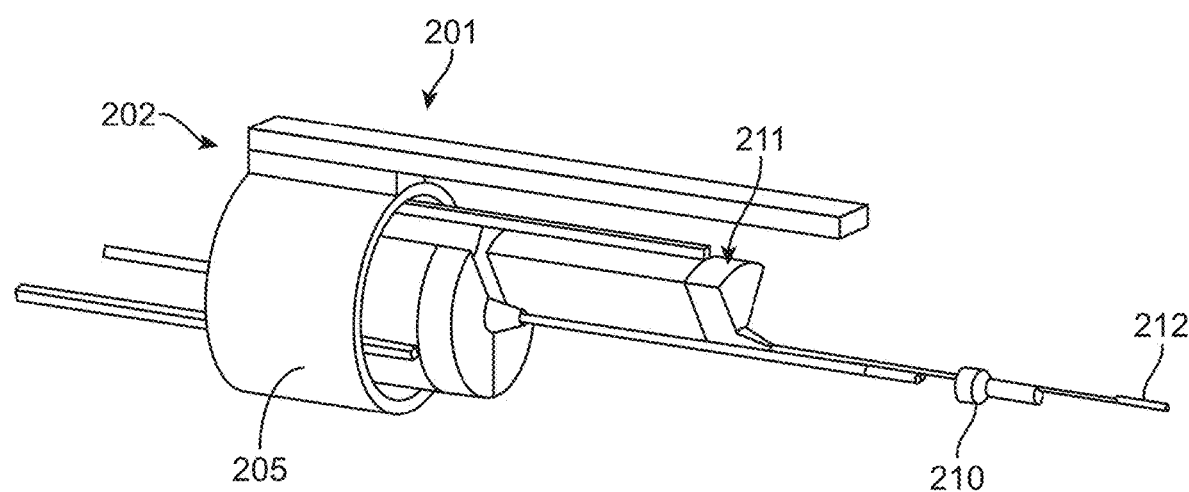
Figure 10H:
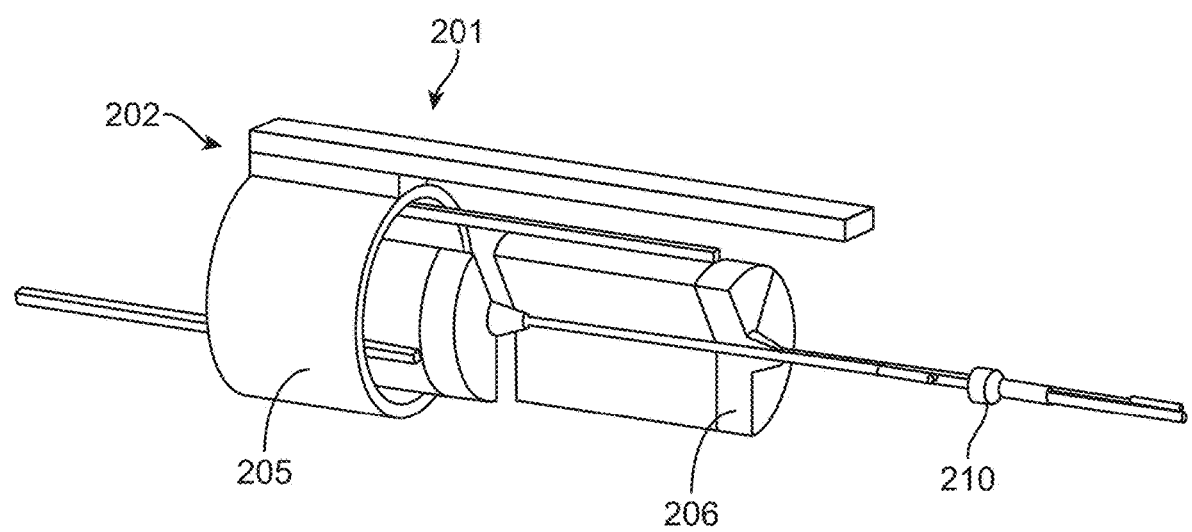
Figure 10I:
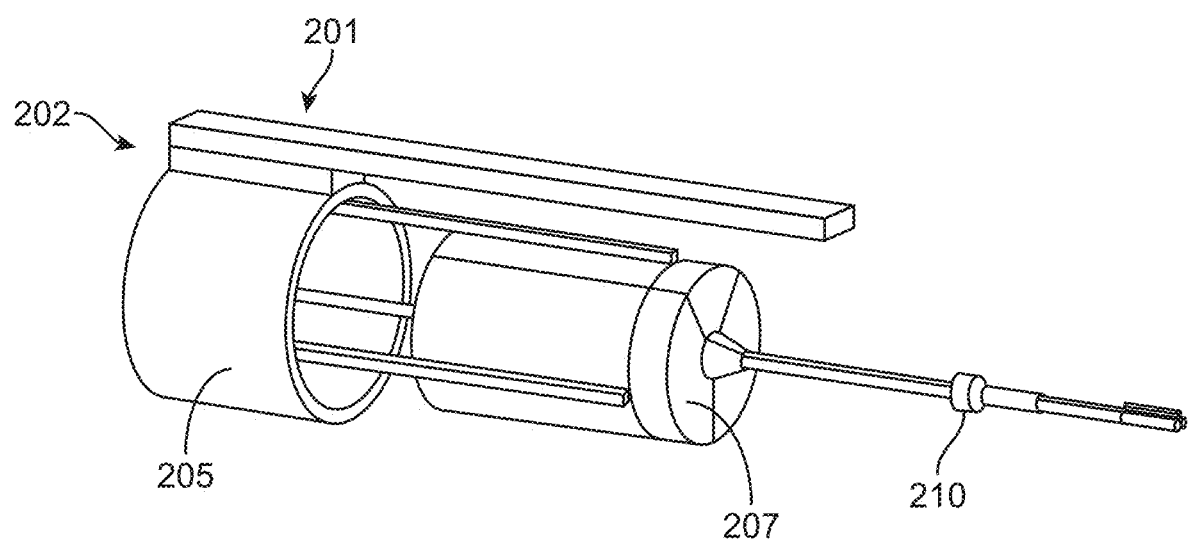
Figure 10J:
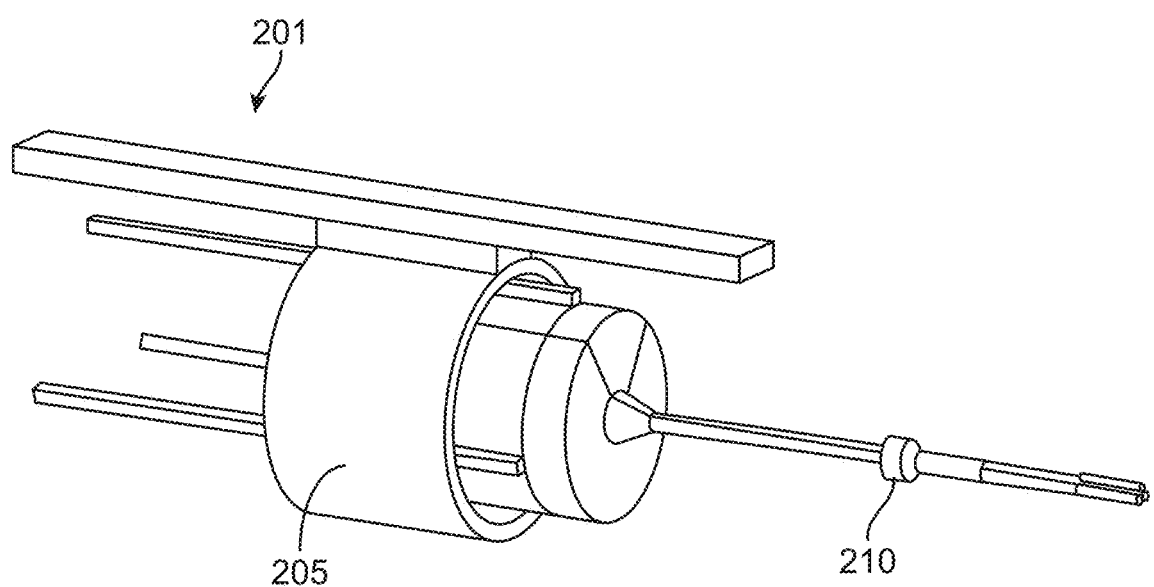
Figure 10K:
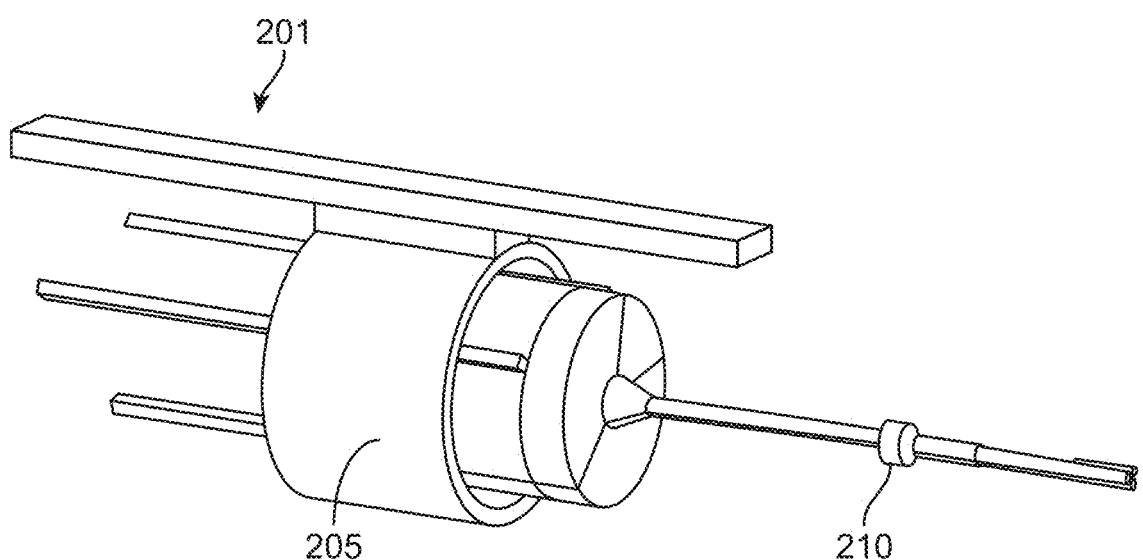

An arm MU may comprise a half disc, such as shown in FIG. 3 as 204-1 and 204-2. An arm MU may comprise a wedge, such as shown in FIG. 10B, as 204-1 and 204-2. Each working end of a robot assembly may be coupled to a respectively MU. The MU for a robotic assembly may be subdivided within the housing 205 to form individual wedges, such as 203, 204-1, and 204-2. A larger number of working ends could be accommodated with a larger number of wedges, each wedge having a relative smaller size than the 3 wedges shown in FIG. 10B. One or more MUs can move independently from one another, such as along a rail as shown in FIG. 10B. One or more MUs can move collectively with one or more MUs, such as a rotational motion as shown in FIG. 10J and FIG. 10K.

Figure 6:
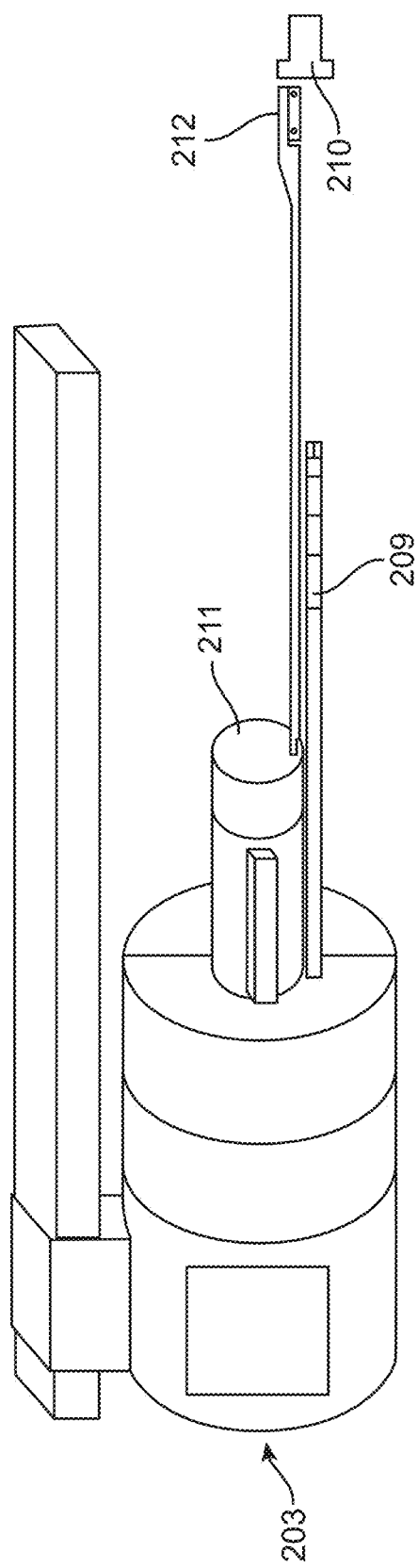
Figure 7:
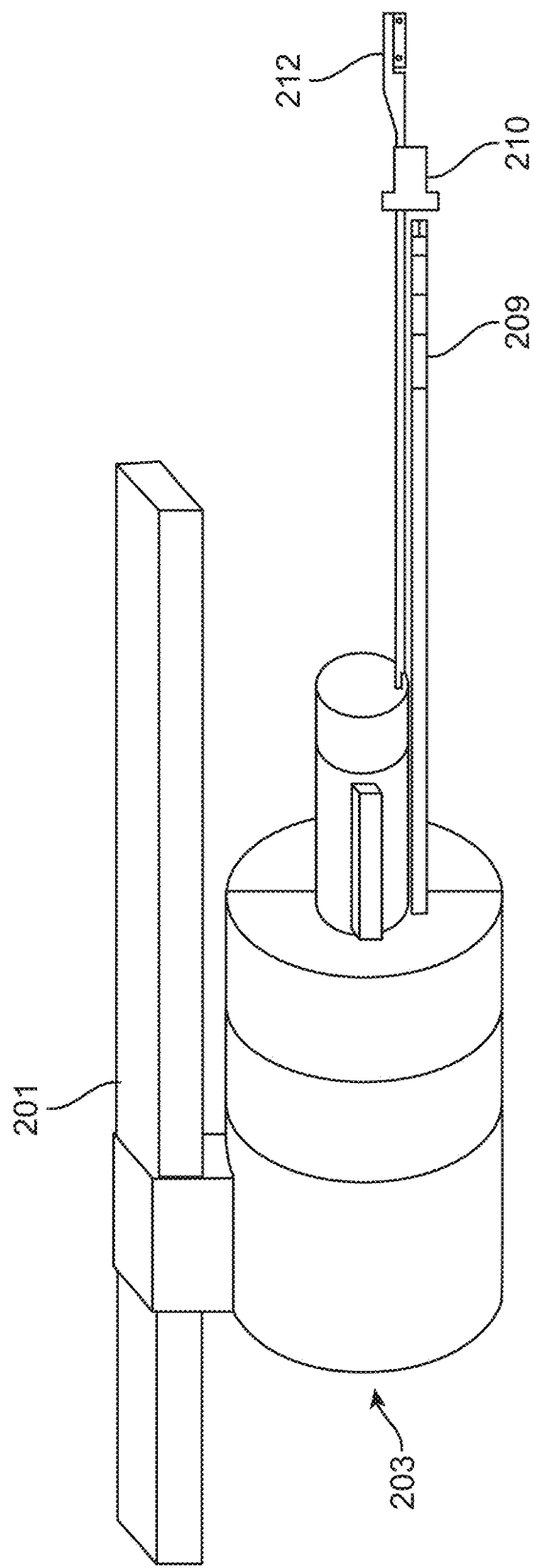
Figure 8:
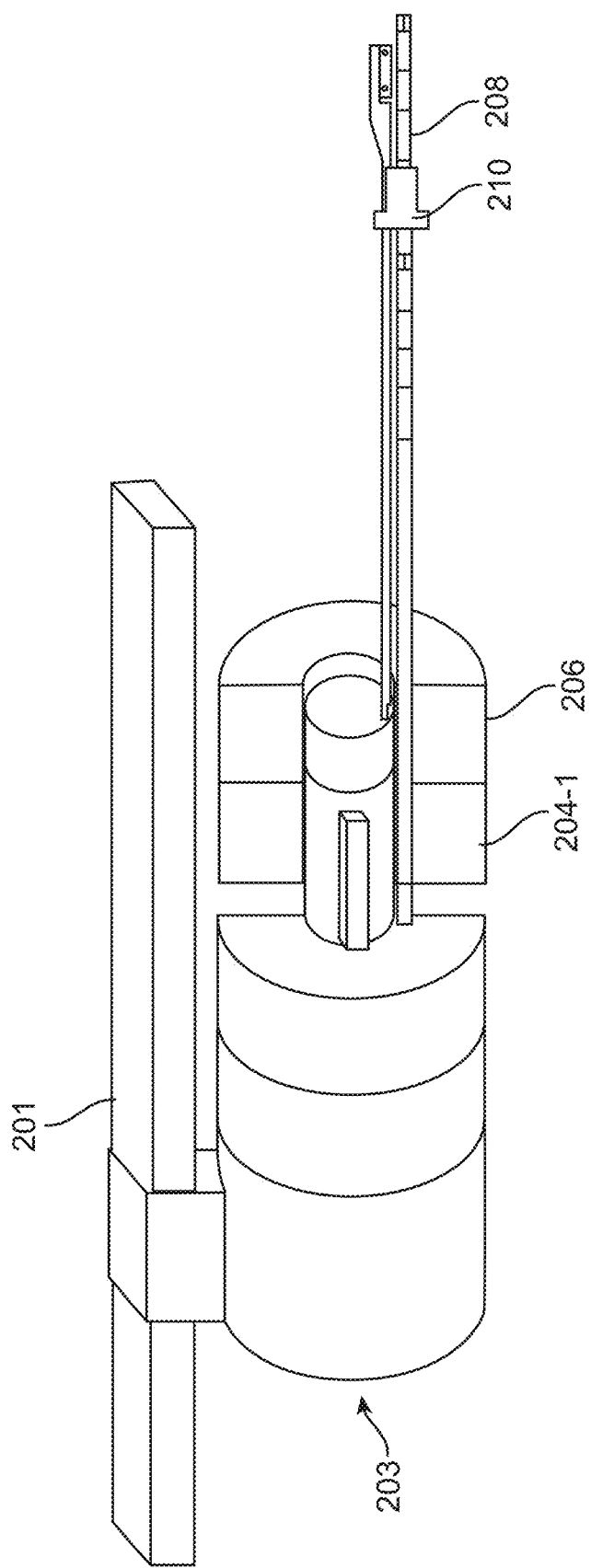

To permit linear motion of the working ends, such as into and out of the trocar, the collective assembly can slide along the bar 201, as shown in FIG. 6 to FIG. 7. Alternatively, an individual working end, such as the camera working end 212, can be inserted into a trocar by linearly translating the camera MU and engagement element 211, without moving the housing 205 along the bar 201 and/or without moving an arm working end.

FIG. 2 illustrates a bar 201 that is coupled to a mounting member 202. The mounting member 202 is coupled to a camera MU electronics housing 205 for a camera MU 203. The mounting member 202 supports the camera MU 203 and allows the camera MU 203 to translate relative to other MUs of the system, parallel to the axis of insertion through a trocar 210. In some embodiments, the camera MU 203 is coupled to a rail 213. The rail 213 may be positioned parallel to the bar 201. The rail may be configured to permit motion of the camera MU 203 on its track. The rail 213 may be configured to extend substantially away from the trocar, such that the rail 213 does not encroach upon space proximal the trocar. FIG. 3 illustrates that a first arm MU 204-1 and a second arm MU 204-2 can be coupled individually to a first rail 214 and a second rail 215. The first rail 214 and the second rail 215 may be positioned parallel to the bar 201. The rails 214 and 215 may be configured to permit motion of the first arm and the second arm independently. The rails 214 and 215 may be configured to extend substantially away from the trocar, such that the rails 214 and 215 do not encroach substantially upon space proximal the trocar. A rail can be a collapsing rail, such as a telescoping rail. A motor unit (203, 204-1, 204-2) coupled to a respective rail (213, 214, 215) can permit movement of the motor unit independent from the housing 205 and independently from another motor unit.

In some embodiments, a workspace visual can be manipulated to create roll of the workspace respective to the working ends of the robot assembly. In some embodiments, one or more working ends are rotated about an axis mechanically. This can be achieved may rotating one or more MUs.

In some embodiments, each MU (that can be operatively connected to a working end) can roll or rotate about the axis of insertion, such as shown in FIGS. 10J-10K. Each MU can roll independently. One or more MUs can roll as a collective. Two arm MUs can roll as a collective, independently from a camera MU. A rail may roll with a MU respective to the housing 205. A housing may roll with the MU and the rail. In some embodiments, a workspace is visually manipulated such that the one or more working ends can be rotated by the visual manipulation of the workspace. In certain embodiments, the MU electronics housing houses at least a motor, and in some embodiments, other electronics for controlling the motor. The MU engagement element may be fabricated to house the elements that may be required to mechanically and electrically couple the MU to its corresponding robot assembly. In some embodiments, the first segment of the system is fabricated to comprise at least one MU. In some embodiments, there are as many MUs as there are robot assemblies.

In some embodiments, there are three Motor Units (MU). In these embodiments, one MU is intended to connect to a camera robot assembly as defined below and is called the camera motor unit 203. The two remaining MUs are each individually known as arm MUs 204-1 and 204-2 and are intended to connect separately to two (2) arm robot assemblies as detailed below.

Figure 4:
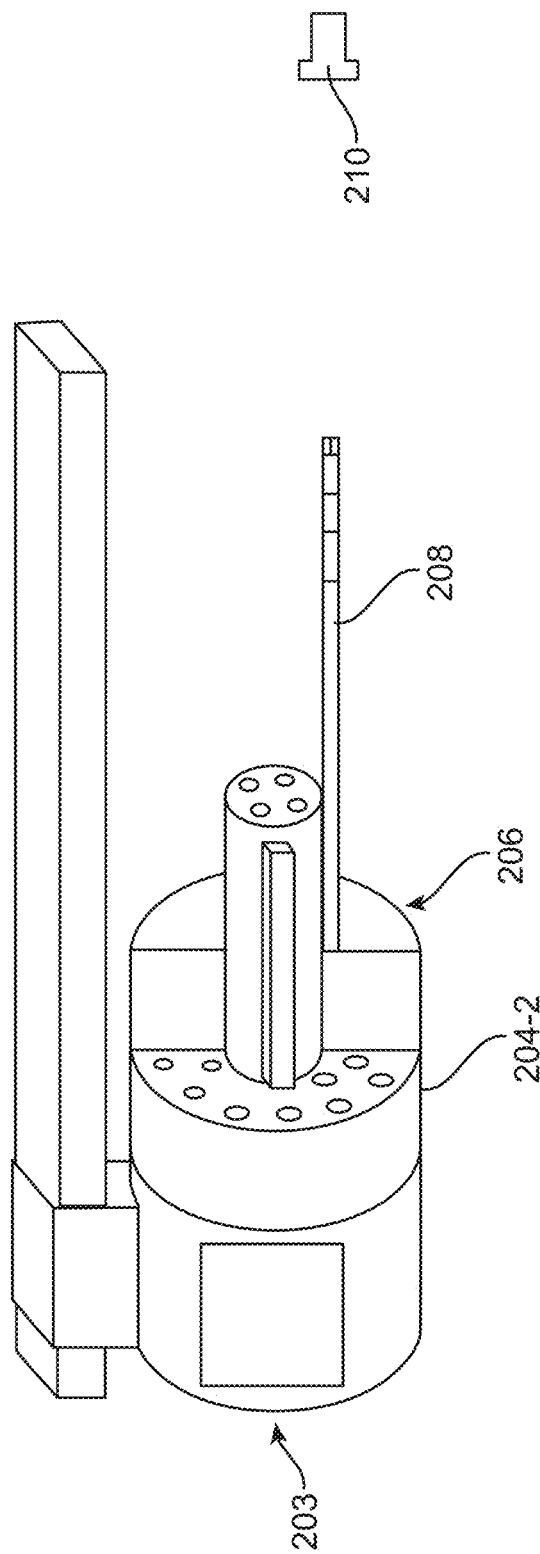
Figure 5:
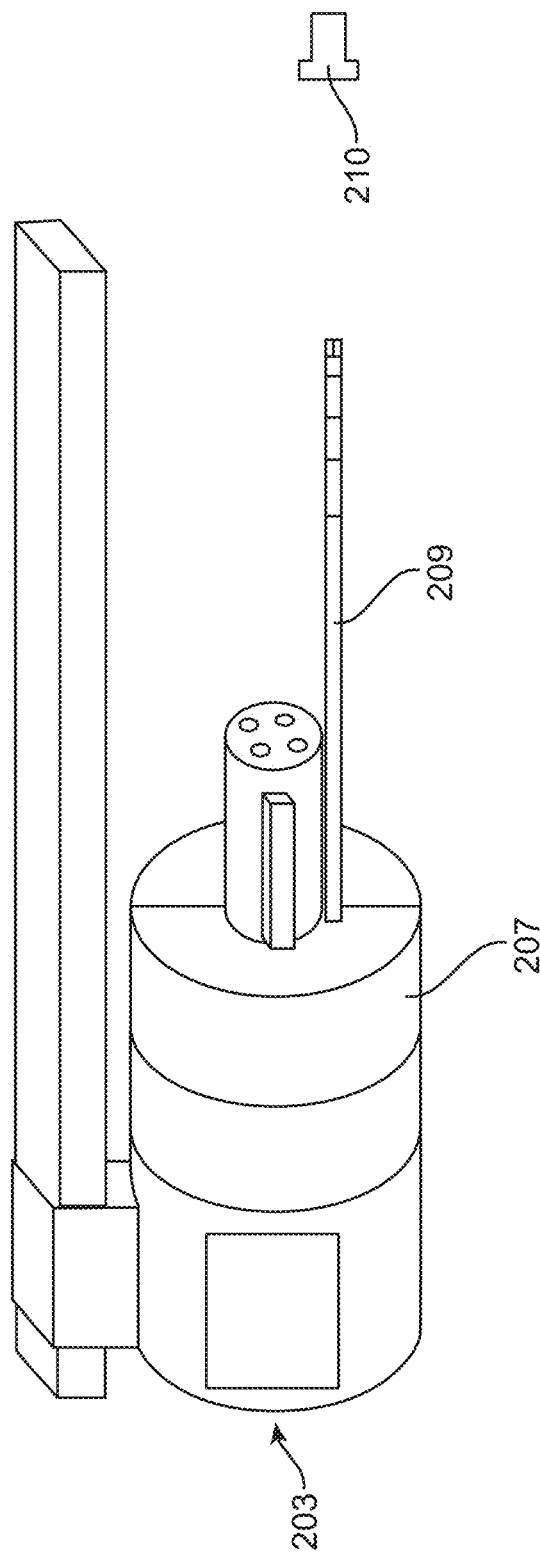

In some embodiments, a robot assembly comprises a robot engagement element, a support tube, a transition element, and a working end. The robot engagement element, according to some embodiments, comprises one or more elements that can mechanically and/or electrically couple the robot assembly to its corresponding MU. FIG. 4 and FIG. 10C illustrates a first robot engagement element 206 for the first arm MU 204-1 and a first working end 208 for the first arm MU 204-1. FIG. 5 and FIG. 10D illustrates a second robot engagement element 207 for the second arm MU 204-2 and a second working end 209 for the second arm motor unit 204-2. FIG. 6 and FIG. 10E illustrates a camera robot engagement element 211 for the camera motor unit 203 and a camera motor unit working end 212 for the camera motor unit 203. The support tube, according to some embodiments, mechanically supports the working end of the robot assembly and facilitates the transmission of mechanical and electrical power and communication. The transition element, according to some embodiments, enables the working end of the robot assembly to translate radially within a trocar as it is inserted through the trocar. FIGS. 11-15 illustrates a camera motor unit transition element 220 that enables the camera motor unit working end 212 to translate radially within the trocar 210 during insertion through the trocar 210.

Figure 11:
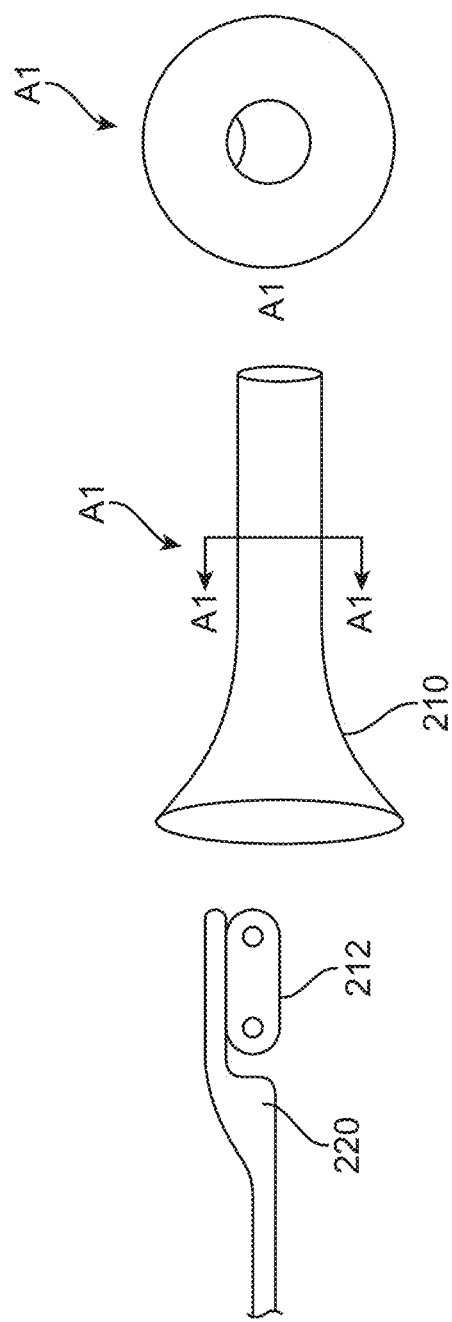
FIGS. 11-15 illustrate an insertion of a camera motor unit through a trocar, in accordance with some embodiments.
Figure 12:
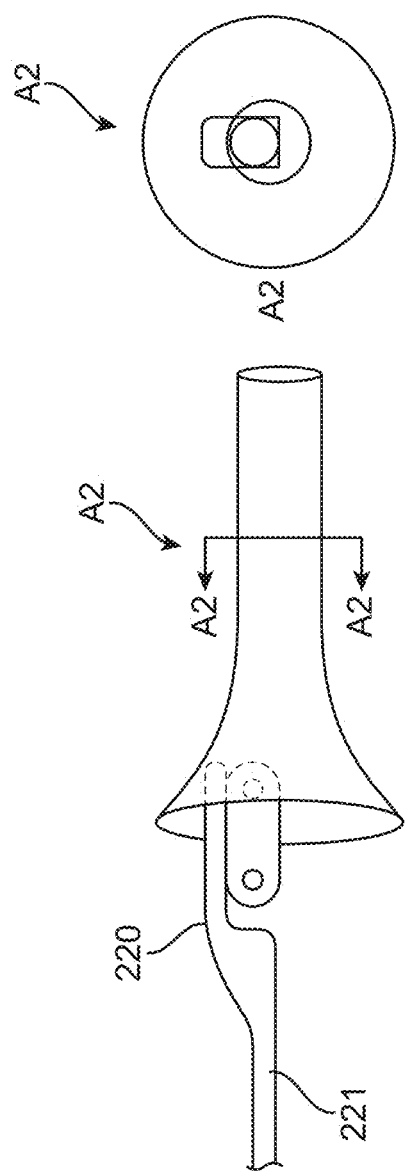
Figure 13:
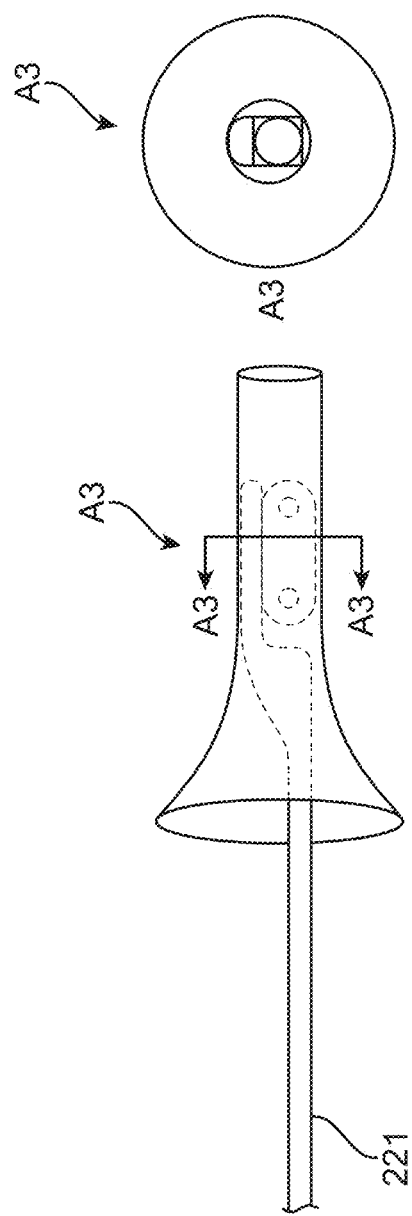
Figure 14:
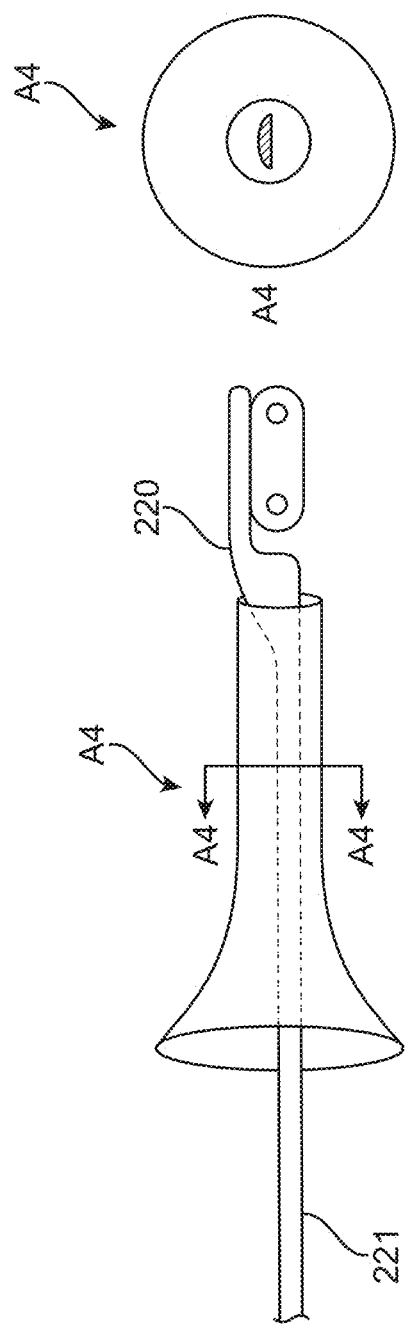
Figure 15:
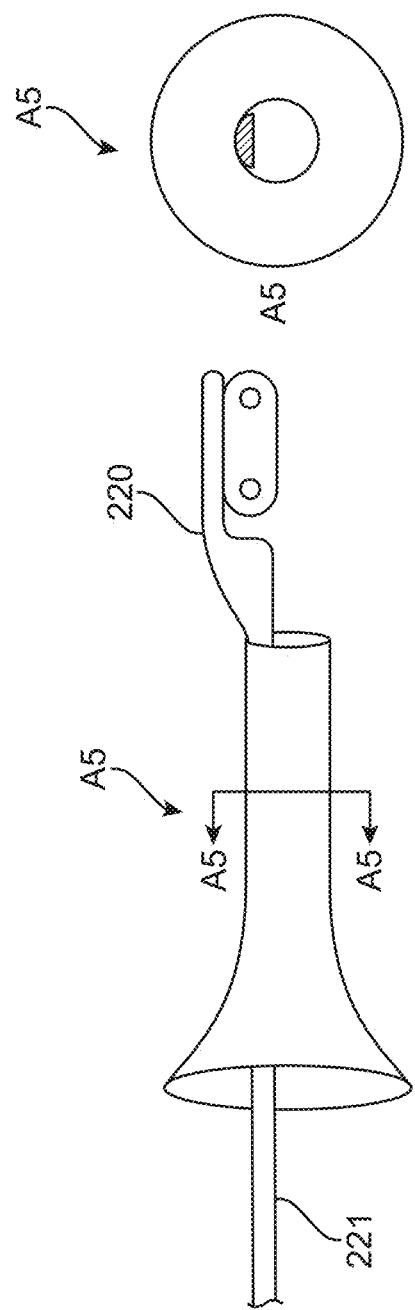

As shown in the cross section view A1 of FIG. 11, the camera working end 212 can be slightly visible as it enters a cross section of the inner lumen of the trocar. As shown in the cross section view of A2 of FIG. 12, a portion of the camera working end 212 can be fully visible within the cross section of the inner lumen of the trocar. As shown in the cross section view of A3 of FIG. 13, a portion of the camera working end 212 and a portion of the transition element 220 that can be coupled to the camera working end 212 can both be fully visible within the cross section of the inner lumen of the trocar. As shown in the cross section view of A4 of FIG. 14, a portion of the support tube can be visible within a central region of the inner lumen of the trocar, as the working end has passed thru the trocar. As shown in the cross section view of A5 of FIG. 15, a portion of the support tube can be moved radially outward and can be visible adjacent an inner wall of the trocar, as the working end has passed thru the trocar. As shown in the cross section view A6 of FIG. 16, a portion of the support tube can be visible adjacent an inner wall of the trocar. A working end of a robotic arm can begin to be inserted into the trocar. As shown in the cross section view A7 of FIG. 17, a portion of the support tube can be visible adjacent an inner wall of the trocar and a portion of a working end of a robotic arm can be visible in a central region of the trocar. As shown in the cross section view A9 of FIG. 18, a portion of the support tube attached to the camera working end and a portion of the support tube attached to the working end of the robotic arm can both be visible adjacent the inner wall of the trocar. The support tube can be moved radially outward to be adjacent the inner wall. As shown in the cross section view A10 of FIG. 19, a portion of the support tube attached to the camera working end and a portion of the support tube attached to the working end of the robotic arm can both be visible adjacent the inner wall of the trocar and a working end of a second robotic arm can be beginning entry to the trocar. As shown in the cross section view A11 of FIG. 20, a portion of the working end of the second robotic arm can pass through the available cross section area of the trocar. As shown in the cross section view A12 of FIG. 21, a portion of a support tube attached to the working end of the second robotic arm can pass through the available cross section area of the trocar. As shown in the cross section view A13 of FIG. 22, each of the support tubes for the camera working end, the working end of the robotic arm, and the working end of the second robotic arm can be positioned adjacent the inner wall of the trocar.

FIGS. 12-15 illustrates a support tube 221 that mechanically supports the camera motor unit working end 212 and facilitates the transmission of mechanical and electrical power and communication.

As stated above, in some embodiments, the system contains three separate robot assemblies, the camera robot assembly, and two arm robot assemblies. In these embodiments, each robot assembly is attached to a corresponding motor units 203, 204-1, or 204-2 (see, e.g., FIGS. 2-6 and FIGS. 10A-10E). In some embodiments, the working end of the camera robot assembly is designed to incorporate and utilize the stereoscopic camera assembly disclosed in U.S. patent application Ser. No. 16/130,734 titled Virtual Reality Surgical Camera System, which is attached in the appendix and is herein incorporated in its entirety. In other embodiments, the Working End of the Camera Robot Assembly is designed to incorporate and utilize other camera systems, for instance, a stereoscopic camera capable of actuating in a yaw and pitch direction. In some embodiments, the Working End of the Arm Robot Assembly is designed to incorporate and utilize a multi-degree of freedom robot with an end effector at the distal end, such as the robotic arms disclosed in U.S. Pat. No. 10,285,765 B2 titled Virtual Reality Surgical Device, and/or the wrist assemblies disclosed in United States Patent Application Publication No. 2019/0142531 A1 titled Virtual Reality Wrist Assembly. Both references are attached in the appendix and are herein incorporated in their entirety. In other embodiments, the working end of the arm robot assembly is designed to incorporate and utilize other robotic surgical instruments.

In some embodiments, the system comprises multiple camera robot assemblies. In some embodiments, each motor unit and its corresponding robot assembly can be unified such that the Working End of the Robot Assembly cannot be easily separated from the motor unit.

In some embodiments, a user may setup the RSS such that it is in a location that is suitable for surgery and is positioned such that the appropriate robot assemblies are ready to be attached to their corresponding motor units. Each motor unit may be properly draped (covered by a sterile barrier) before, during or after the attachment of each robot assembly. Once the robot assemblies are attached and properly draped (if applicable), the patient can be brought in and placed on the surgical table and prepared for surgery. The incision for a trocar 210 will then be made, and the trocar will be inserted into the patient to provide access to the desired operation site. For example, in order to access a patient's abdominal cavity, a trocar 210 may be inserted into the patient's abdominal wall. In this example, the patient's abdomen will then be insufflated with carbon dioxide. With the patient's abdomen insufflated, the RSS can then be maneuvered into position, over the patient and the trocar 210. The RSS can then be coupled to the trocar 210. Once the trocar 210 is aligned and attached to the RSS, the Robot Assemblies can be inserted one by one into the patient (see, e.g., FIGS. 7-9 and FIGS. 10G-10I).

In some embodiments, as the working end of a robot assembly is inserted into the trocar 210, it is deflected towards the center of the trocar 210 by contacting the interior wall of the trocar 210 allowing the working end of the robot assembly to pass through the trocar 210. In some embodiments, as the working end passes through the trocar 210 the trocar 210 maintains a seal around it such that insufflation is maintained. Once the working end passes through the trocar 210, the transition element guides the working end to un-deflect such that it moves radially outward within the trocar 210 giving space for the next working end to pass through. In some embodiments, the radial motion within the trocar 210 can be achieved automatically or in a controlled fashion by incorporating additional actuated joints or mechanisms within the support tube of the robot assembly or within its corresponding motor unit or on the RSS. As shown in FIG. 10J and FIG. 10K, one or more working ends can collectively rotate while maintaining relative positioning to one another. This rotational motion can be achieved by rotating housing 205. This rotational motion can be achieved by rotating a channel or a track within an inner surface of housing 205.

In some cases, a working end may be operatively coupled to a support tube, such as via a support tube. In some cases, the support tube may comprise the transition element. In some cases, the support tube may be a separate element from the transition element. The transition element may comprise a tapered end. The transition element may comprise a curved edge. In some cases, the support tube may not comprise a transition element.

A shape of the transition element (such as a curved edge or a tapered end) may at least in part provide the radially outward movement of the working end upon exiting the trocar and entering the body cavity. A stiffness of the support tube, the transition element, or a combination thereof may at least in part provide the radially outward movement of the working end upon exiting the trocar and entering the body cavity. A stiffness of a transition element, a support tube or a combination thereof may be selected at least in part by selecting a thickness of the support tube, selecting one or more materials to form the support tube, selecting a length of the support tube, or any combination thereof.

The radially outward movement of the working end upon exiting the trocar and entering the body cavity may at least in part be provided by manipulating a stiffness of the support tube, hinging the support tube or motor unit to which the support tube is connect, by addition of a spring component, or any combination thereof. In some cases, the support tube may be partially coupled or temporarily coupled to the trocar to provide or increase a radially outward force upon the working end as it exits the trocar.

Figure 43:
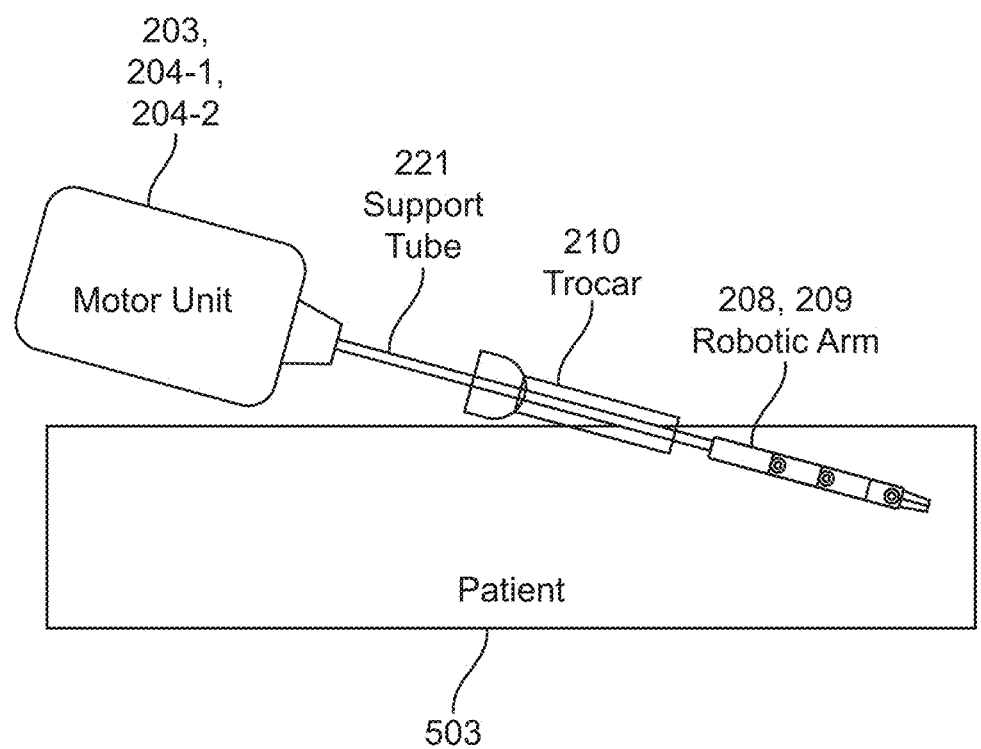
FIG. 43 illustrates entry of a robotic arm through a trocar into a patient.
Figure 44:
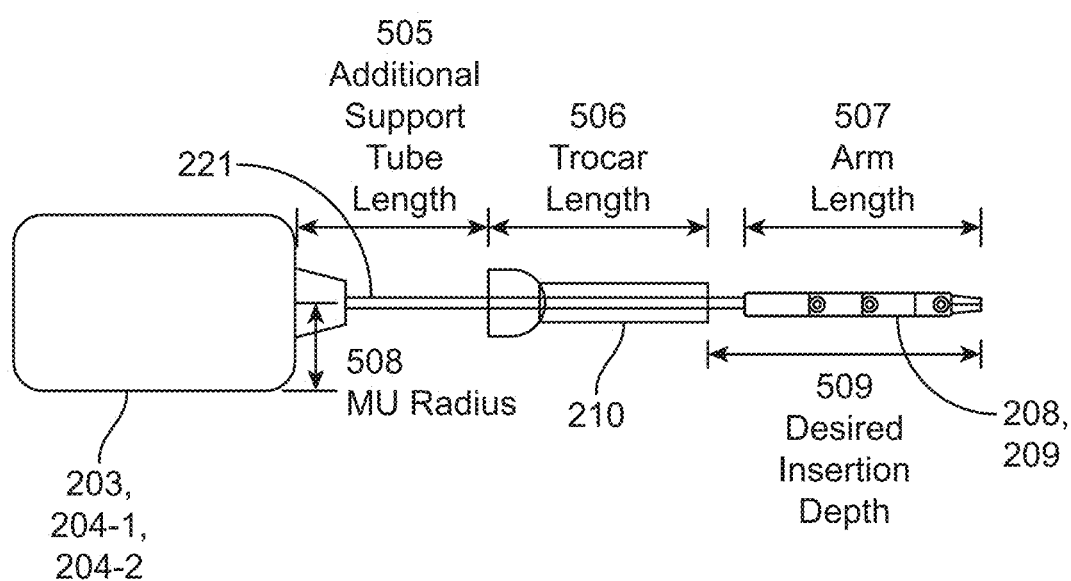
FIG. 44 illustrates various dimensions of the robotic assembly.

Referring to FIG. 43 and FIG. 44, a robotic arm, such as 208 or 209 is inserted into a portion of a patient 503 by inserting the robotic arm through a trocar 210. The robotic arm (208 or 209) may be operating connect to a motor unit (203, 204-1, 204-2) that remains outside the patent 503 by a support tube 221. The support tube 221 may contain electrical components, mechanical components, or a combination thereof. The length of the support tube 221 may be driven by a geometry of the support robot, the parameters of the procedure for robot placement, lengths of components used in the surgical procedure, or any combination thereof. An additional support tube length 505 may be modified. A trocar length 506 may be modified. A robotic arm length 507 may be modified. A desired insertion depth 509 of a robotic arm within a body cavity of the patient 503 may be modified. A radius 508 of the motor unit may be modified.

Figure 45:
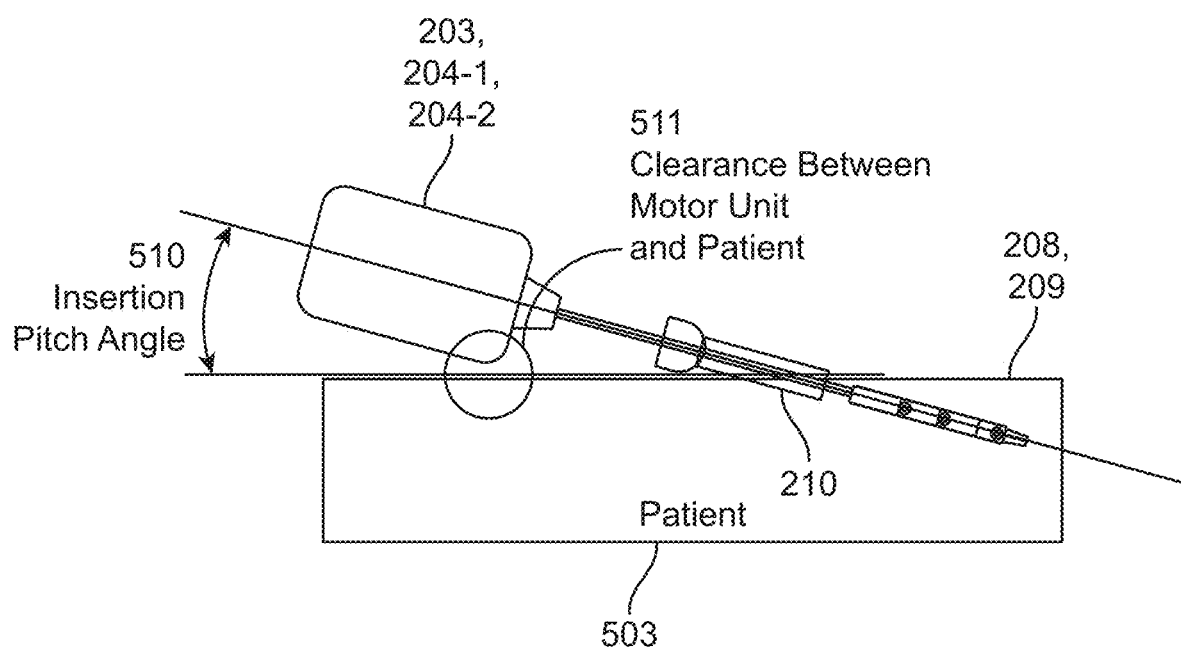
FIG. 45 describes an insertion pitch angle and clearance between a motor unit and a patient when a portion of the robotic assembly is inserted through a trocar and into a patient.

As FIG. 45 shows, there may be an additional support tube length that may keep the motor unit further from the patient to avoid contact and provide a clearance 511 between a motor unit and the patient 503 across a range of insertion pitch angles 510. A distance that the robotic arm may extend beyond the trocar may be driven by parameters of one medical procedure from another. A trocar length 506 may be fixed by the size of the orifice and may be fixed based on off-the-shelf components, such as those that are supplied to a hospital. A motor unit size may be determined by one or more design parameters. Therefore, a length of the support tube may be one parameter that permits a robotic arm to be inserted to a desired depth 509 while maintaining a sufficient separation between the motor unit and the patient. In some cases, a length of the support tube may be about 500 millimeters (mm) between the robotic arm and the motor unit. In some cases, a length of a support tube may be from about 400 mm to about 600 mm. In some cases, a length of a support tube may be from about 300 mm to about 700 mm. In some cases, a length of a support tube may be from about 300 mm to about 800 mm. In some cases, a length of a support tube may be from about 400 mm to about 1000 mm. In some cases, a length of a support tube may be at least about 400 mm. In some cases, a length of a support tube may be at least about 300 mm. In some cases, a length of a support tube may be at least about 500 mm.

In some cases, it may be advantageous for a support tube to provide sufficient stiffness (for example, during insertion) to support at least a portion of a weight of the robotic arm (preferably, substantially the entire weight of the robotic arm) and be able to push the robotic arm through the trocar (for example, during initial insertion). The trocar may comprise a sealing membrane. The sealing membrane may provide friction to the insertion of the arm. Given this friction, the stiffness of the support tube may overcome this force without substantially buckling of the support tube. Once inserted, a trocar may provide additional stiffness to the support tube, either by direct coupling or by associating the support tube with an portion of an inner wall of the trocar. The amount of or a length of the support tube that exits the trocar may be shorter than the total length of the support tube and may be substantially stiffer in bending over that length. This design or similar may permit the robotic arm to exert more force during one or more actions, such as when the robotic arm may be pulling a suture or blunt dissecting a tissue.

Figure 46:
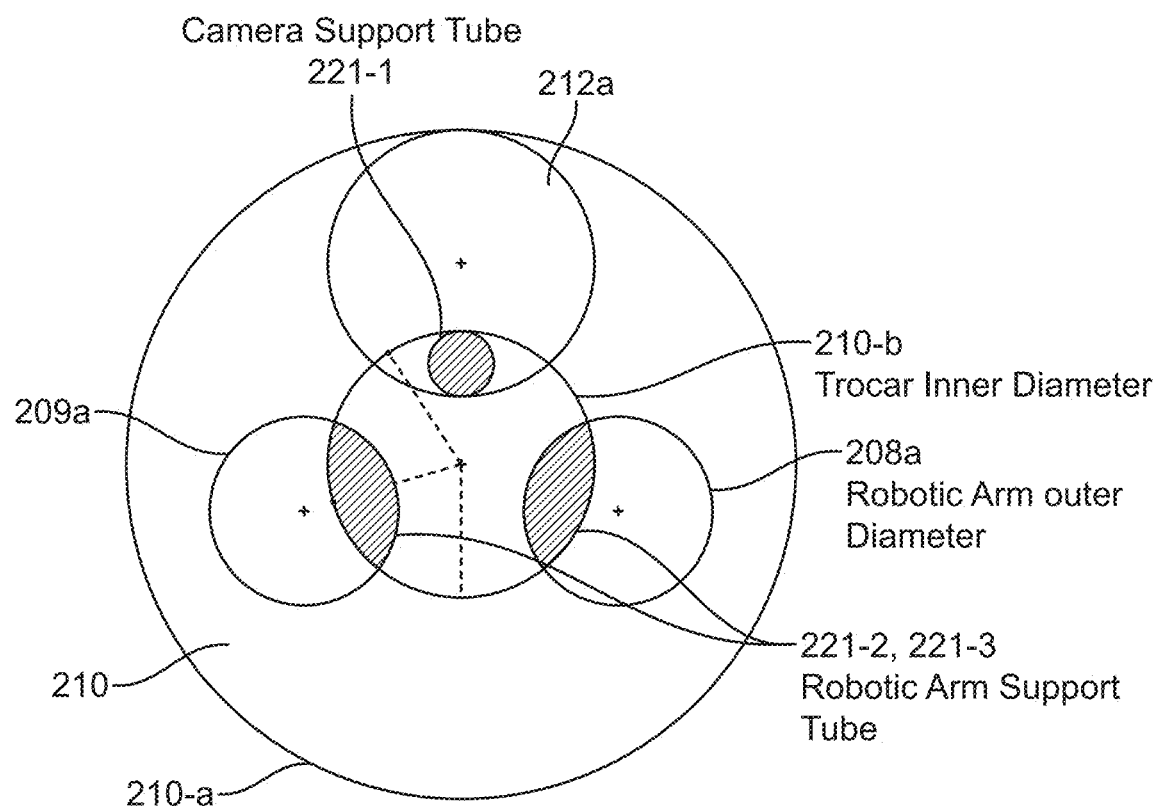
FIG. 46 illustrates a cross sectional area of the trocar and diameter or related components.

Referring to FIG. 46, two robotic arms and a robotic camera may be sequentially inserted through a trocar. An inner diameter of the trocar 210-*b* and therefore the outer diameter of the trocar 201-*a* may be minimized to facilitate the sequential insertion. FIG. 46 shows the inner diameter of the trocar 210-*b* and the placement of the three support tubes (two arms and one camera) once inserted into the trocar.

Depending on the diameters of the arms and camera at their maximum, and the inner diameter of the trocar, the available space for a support tube may be very important. The highlighted areas 221-1, 221-2, 221-3 may be the acceptable sizes of each support tube, assuming that the camera may be inserted first, then one arm, and finally the other in a sequential order. When the second arm is inserted through the trocar, it may fit in the trocar inner diameter 210-*b* along with the camera support tube and the other arm support tube. FIG. 46 shows the trocar 210 having an inner diameter and an outer diameter 210-*a*. The highlighted areas show a camera support tube 221-1, a support tube of a first robotic arm 221-2, and a support tube of a second robotic arm 221-3. The outer diameter of the camera 212*a*, the outer diameter of the robotic arm 208*a*, and the outer diameter of the robotic arm 209*a* are also shown.

Figure 47:
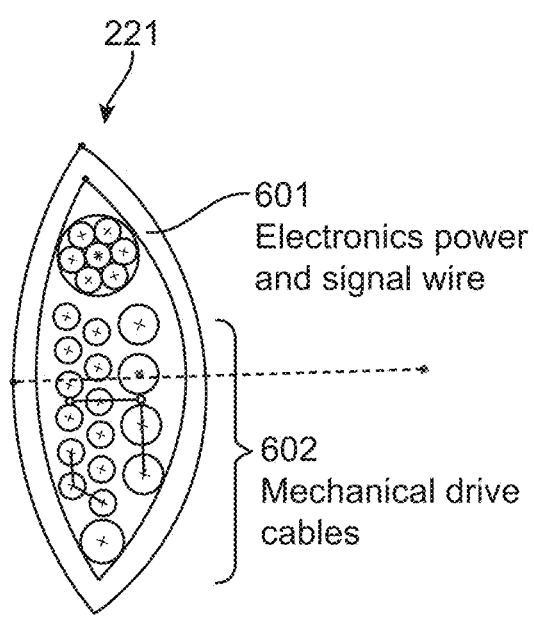
FIG. 47 illustrates a cross sectional area of a support tube and an example of the electrical components and mechanical components housed within.

A purpose of the support tube may be to at least partially provide mechanical support for the robotic arm as well as a conduit for one or more electronic communication components 601 and mechanical components 602 (such as drive cables). The support tube may be hollow. The support tube may comprise an inner lumen along at least a portion of its length. FIG. 47 shows a layout of some of these components as they pass through the support tube.

To create area inside a support tube for a plurality of electrical and mechanical components (such as drive cables, one or two electrical signal/power wires), a thickness of the walls of the support tube may be minimized. Minimizing the thickness of the support tube to accommodate electrical and mechanical components may compromise a stiffness of the support tube in bending and in compression. The support tube cross sectional shape, wall thickness, material, fabrication method, attachment methods, usage parameters and potential failure modes may be considered when choosing an implementation.

Fabrication Methods

For support tubes, various fabrication methods may be implemented. In some cases, we may roll form a circular tube to create an iris-shaped profile. Another option may be to weld together two circular segments of tubes. Welding may be difficult and may leave a rough or unclean internal seam. Another option may be to draw form the support tube using a die. This method may allow the material to be cold worked as it is shaped.

Figure 48:
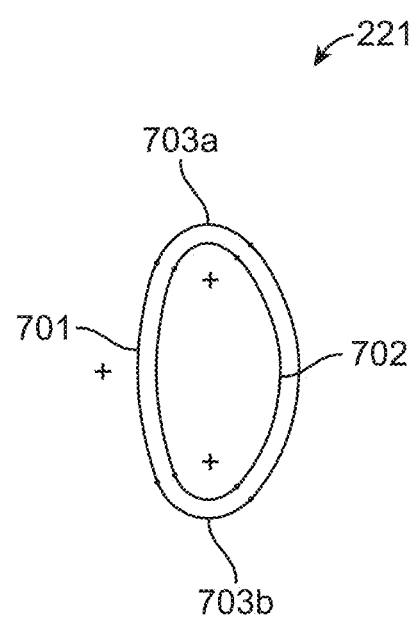
FIG. 48 illustrates a cross sectional area of a support tube demonstrating an example of the curvature of each side of an exemplary support tube.

The resulting cross sectional shape rounds over the corners of the profile shown in FIG. 48, which may be desirable in that the internal surface is smoother, and the compression and bending performance of the support tube may be more predictable.

The support tube profile may have an outer (left) curve 701 that efficiently nests up against the inner diameter of the trocar while the inner (right) curve 702 may be of smaller diameter which may make the overall support tube wider. The top curve 703*a* and bottom curve 703*b* may smoothly translate from one to the other without creasing the metal tube, which may be weaker in bending. The corner radius may be large enough to accommodate one or more data wires.

Figure 49:
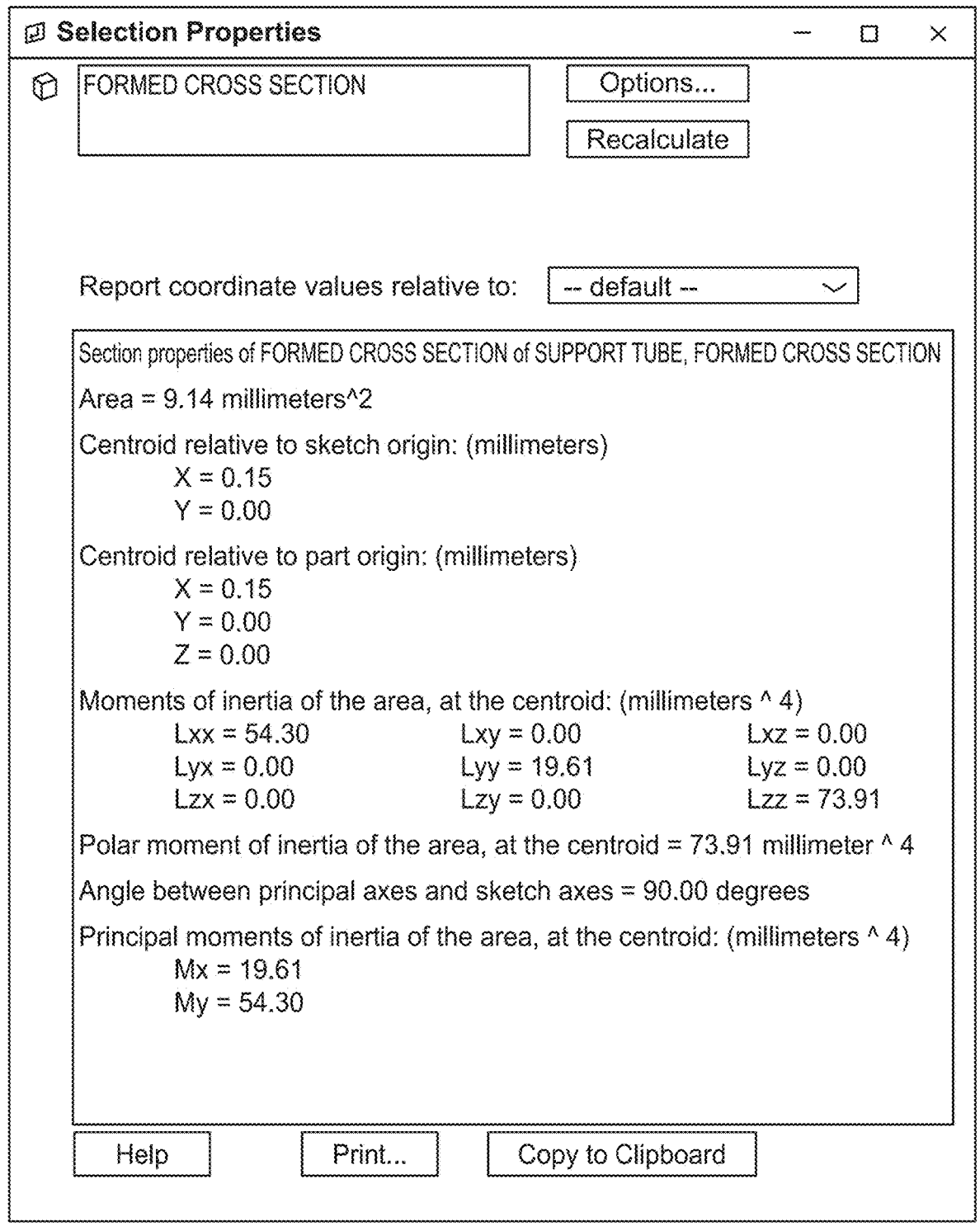
FIG. 49 illustrates use of a software program (Solidworks™) to calculate various parameters, such as an area moment of inertia.

Bending stiffness of the cross section shown in FIG. 48 may be governed by the following equation (when the support tube is assumed to behave as a beam):

$$M(x) = -EIK$$

where 'M' is the bending moment, 'E' is the material's modulus of elasticity, 'I' is the area moment of inertia, and 'K' is the curvature of the beam due to bending. The material may be 304 Stainless Steel (it may be compatible with medical applications and may have improved weldability over 316 stainless). The modulus may be determined. The cross section of the formed support tube may determine the area moment of inertia, which was calculated in Solidworks™ (See FIG. 49.)

The principle moments of inertia may be calculated to be 19.6 mm^4 in the 'x' bending direction (the thinner dimension) and 54.3 mm^4 in the 'y' bending direction. So by cross sectional shape, one can see that the support tube may be almost three times stiffer in the vertical direction than in the horizontal. On the robot, the 'y' direction may be more closely aligned to the gravitational direction so that the support tube may be stiffer under the weight of the robotic arm.

The support tube may contain one or more drive cables (such as 14 drive cables). The drive cables may be in tension (sometimes constantly in tension) to varying levels. The support tube may be in constant compression along its long axis. Traditionally, a long beam in compression may be less desired because it may tend to buckle if the flexural stiffness is too low or the compressive load is too high. The tensioned cables internal to the support tube may provide a mechanism to improve the bending stiffness of the tube.

Different Properties that May Affect Bending Stiffness

Thicker tube wall thickness (in the inward direction, outer profile remains): may increase the second moment of area ('I' in the beam bending equation) approximately linearly. A rough approximation for a thin walled round support tube may be based on the following equation, where I=Pi*r^3*t, where t=thickness; may increase buckling strength slightly; may increase the weight of the support tube (may be by a small amount); may increase the compressive strength of the cross section appreciably; may decrease the internal area of the support tube (where cables and wires may be run); or any combination thereof.

Thicker tube wall thickness in outward direction: may increase the second moment of area significantly (again I=Pi*r^3*t, where 'r' is the radius of the support tube that may be increasing; may increase buckling strength slightly; may increases the weight of the support tube slightly; may not change the compressive strength appreciably unless the dimension changes significantly; may maintain the internal area of the support tube for wires and cables; or any combination thereof.

Longer support tube: may be weaker in bending; may have a lower natural frequency; may decrease buckling strength (compressive stiffness along the axial direction), or any combination thereof.

Support Tube Attachment Methods

Figure 50:
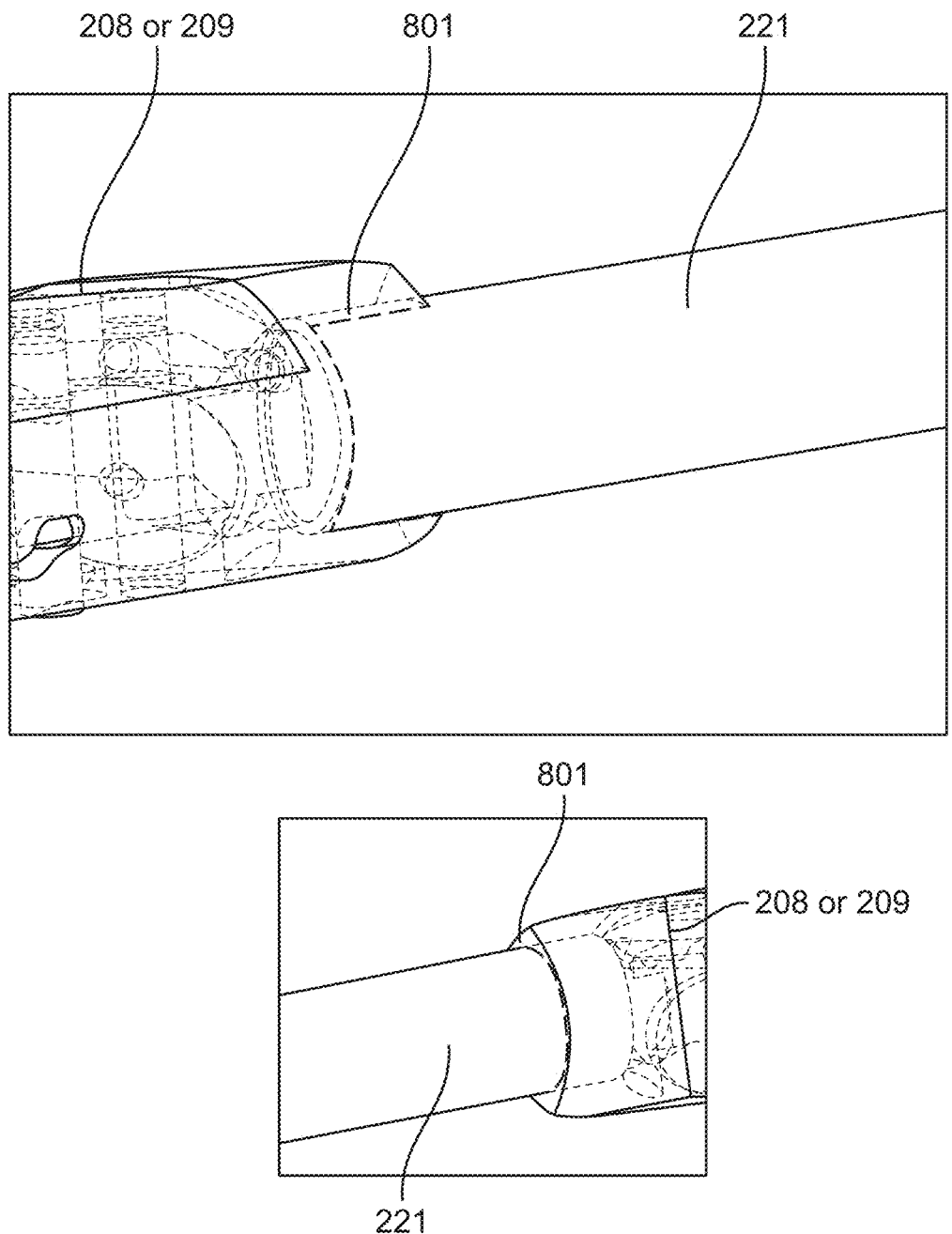
FIG. 50 illustrates an example of attachment between a support tube to a corresponding robotic arm.

It may be desirable for a support tube to be rigidly attached to both the robotic arm and the motor unit. Because the robotic arm may comprise steel at the proximal end, welding the two bodies together may be desired. Rather than use a butt joint, the support tube may be partially inserted into the proximal end of the robotic arm body and a longer, substantially stiffer in bending, weld line 801 may be created. FIG. 50 shows how the support tube 221 and robotic arm (208 or 209) may interface. The dotted red line is the weld line 801.

The proximal end of the support tube may mount to the motor unit, which may comprise aluminum. Directly welding the support tube to the motor unit may not be an option. Alternatively, one or more brackets and one or more stiffening plates may be welded on to the support tube at the proximal end to allow the support tube to be bolted to the motor unit.

The support tube may need to be positioned with accuracy relative to the motor unit. In such cases, one or more alignment dowel pins may be used.

Figure 51:
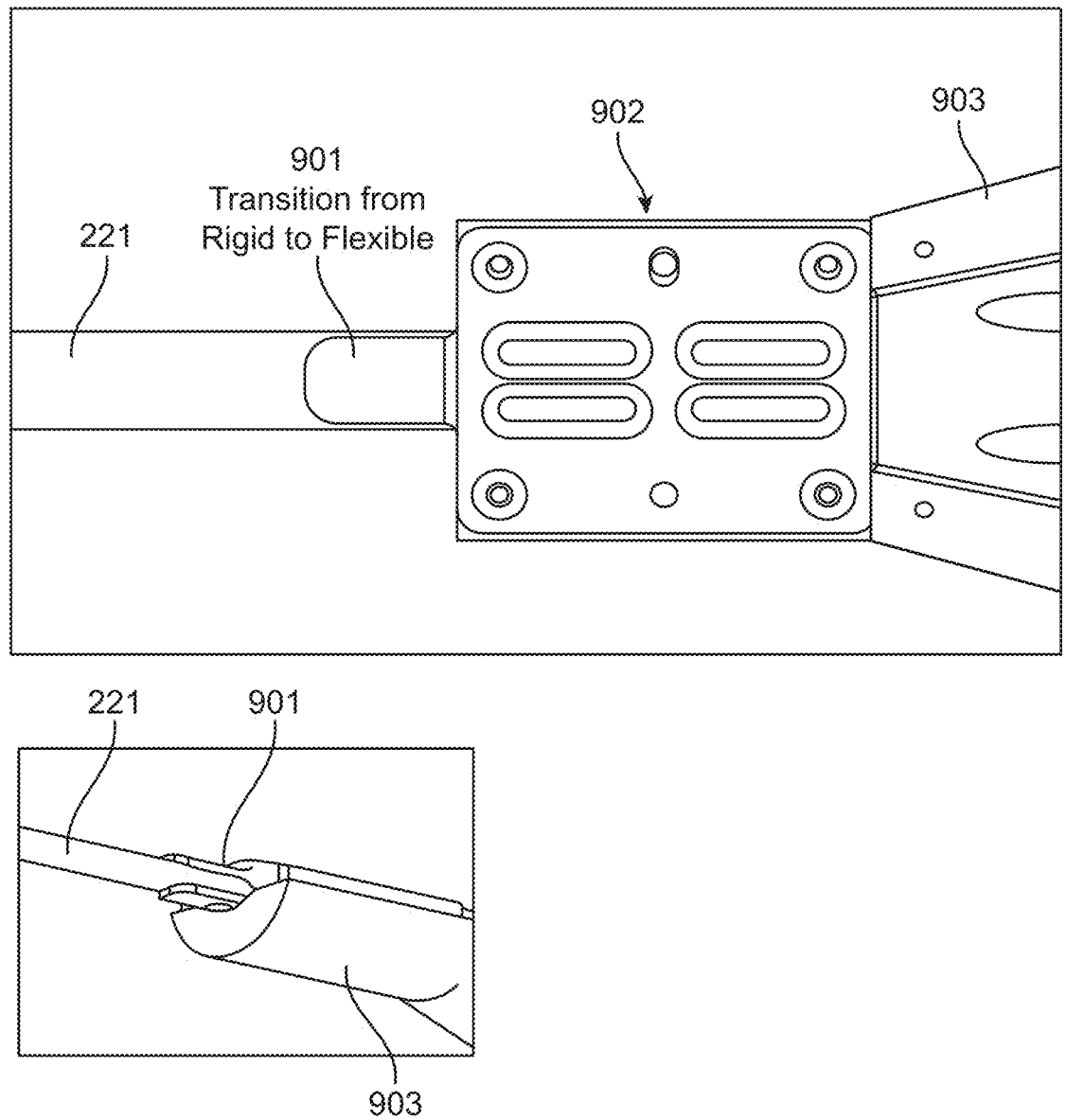
FIG. 51 illustrates an example of attachment between a support tube and corresponding motor unit.

As shown in FIG. 51, the cross section of the support tube may be clamped between two substantially rigid brackets 903 under a large compressive load from the bolts. To ensure that the cross section does not collapse under this force, the bracket 903 itself and a small stiffening plate 902 may be welded to the support tube 221. The stiffening plate 902 and the thin protrusion 901 from the bracket 902 may be extended beyond the mounting bracket 903 to help create a smoother transition in bend stiffness. The sharp transition in bending stiffness between the support tube 221 and the mounting bracket 903 may cause a weak point when the support tube 221 is under bending moment. One or more added plates may help to minimize this effect.

Figure 16:
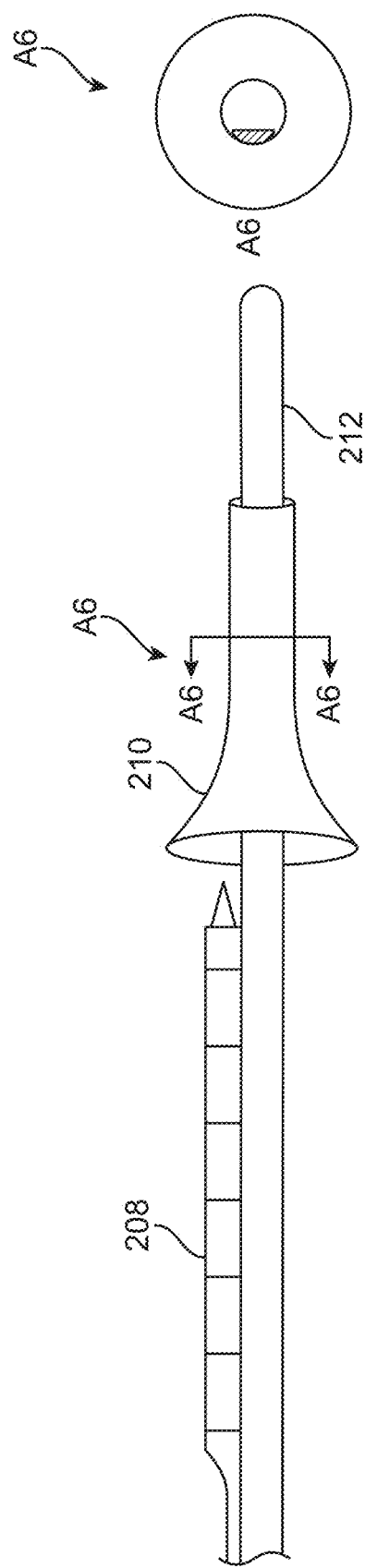
FIGS. 16-22 illustrate a first arm motor unit, a second arm motor unit, and a camera motor unit being inserted through a trocar, in accordance with some embodiments.
Figure 17:
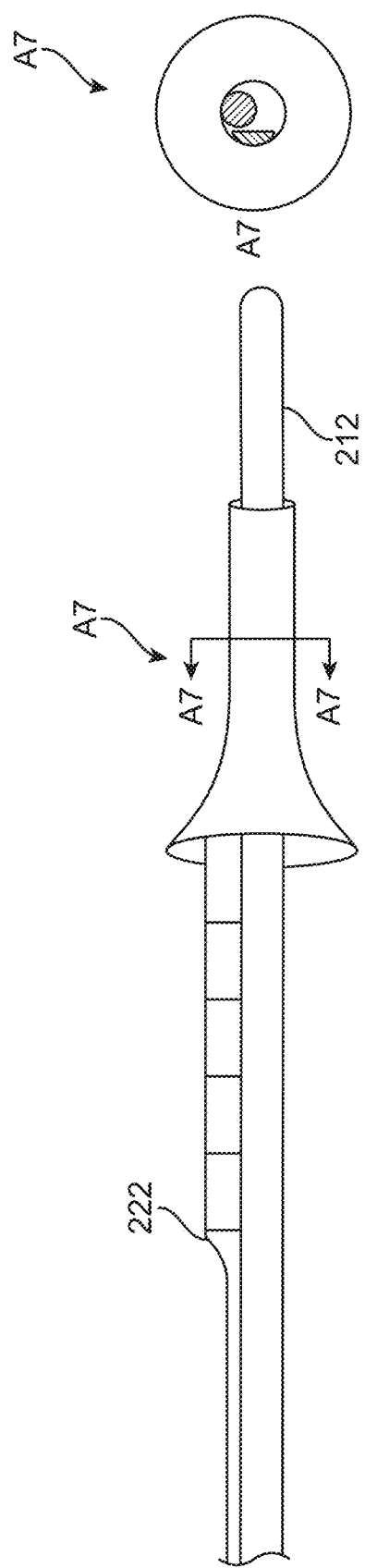
Figure 18:
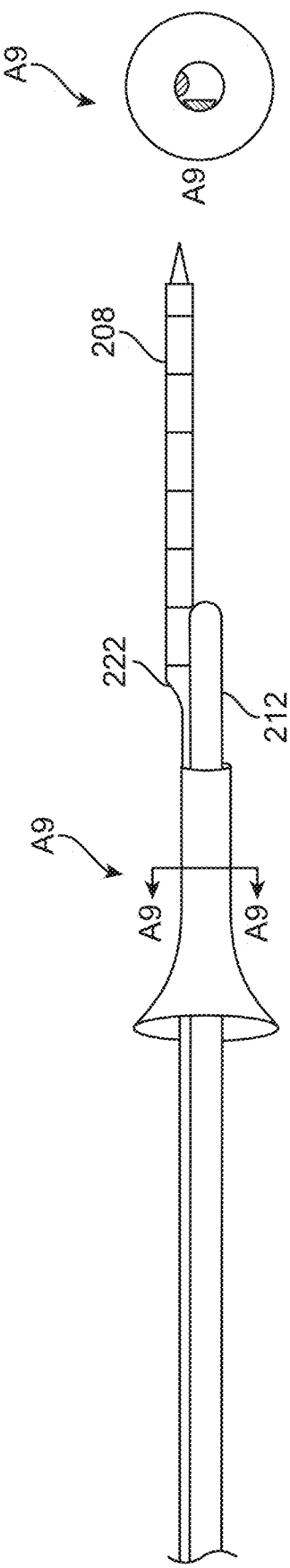
Figure 19:
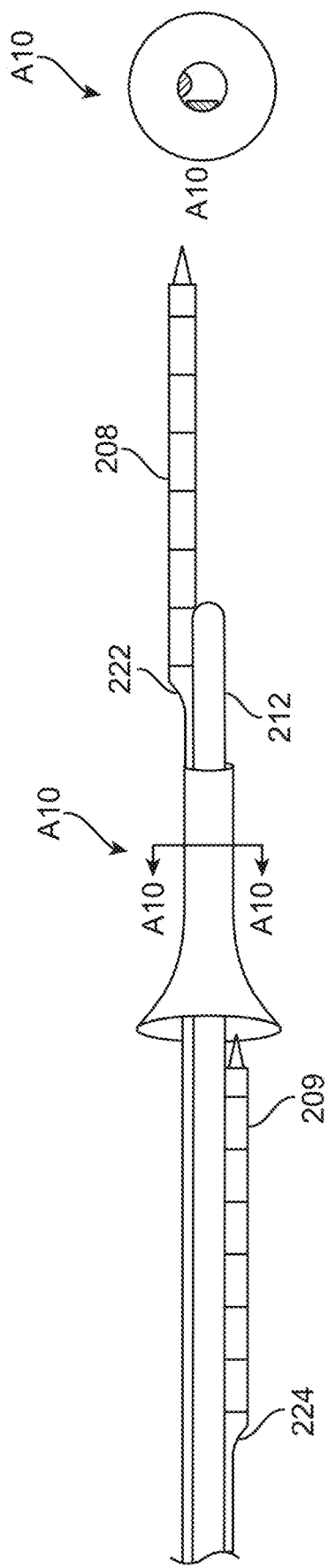
Figure 20:
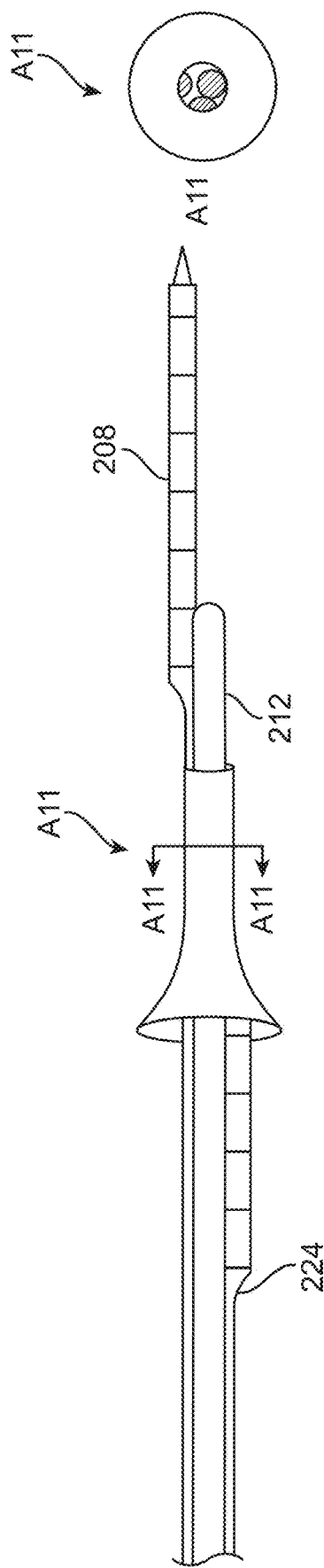
Figure 21:
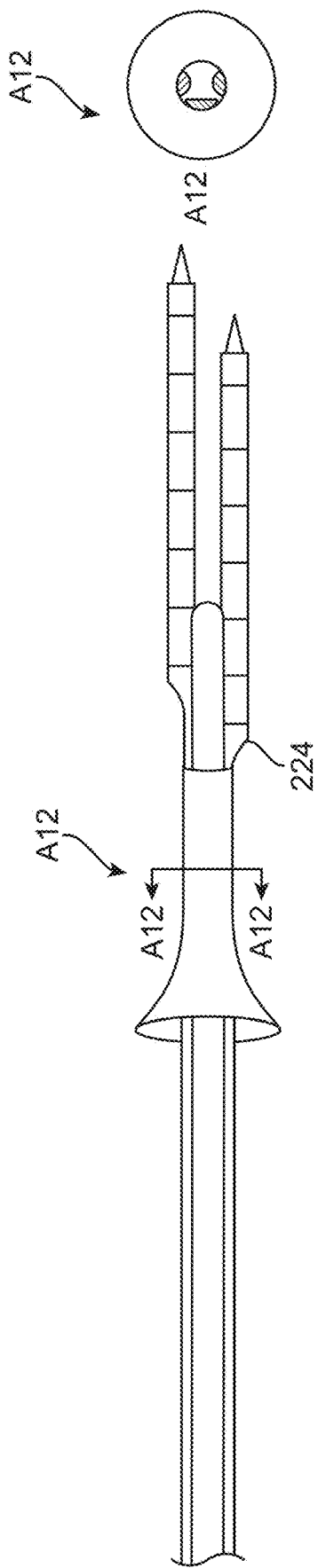
Figure 22:
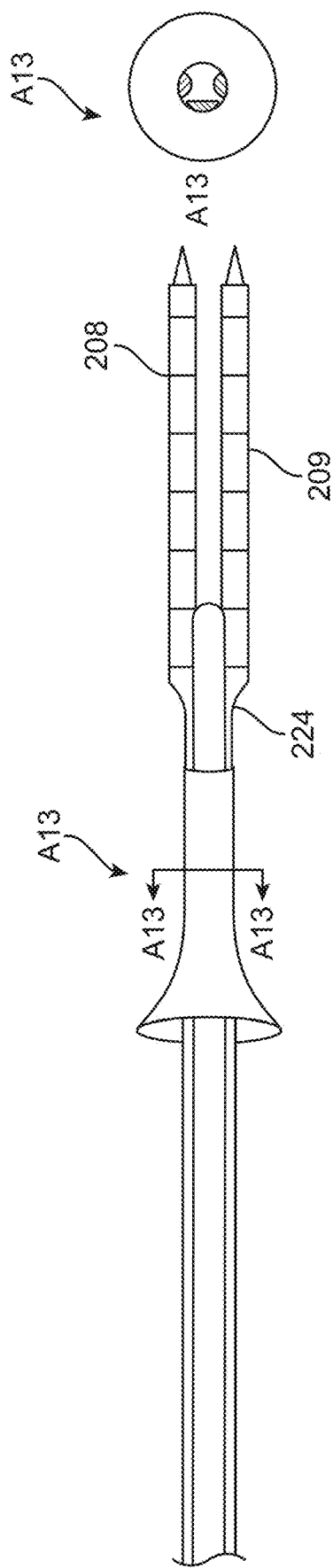
Figure 23:
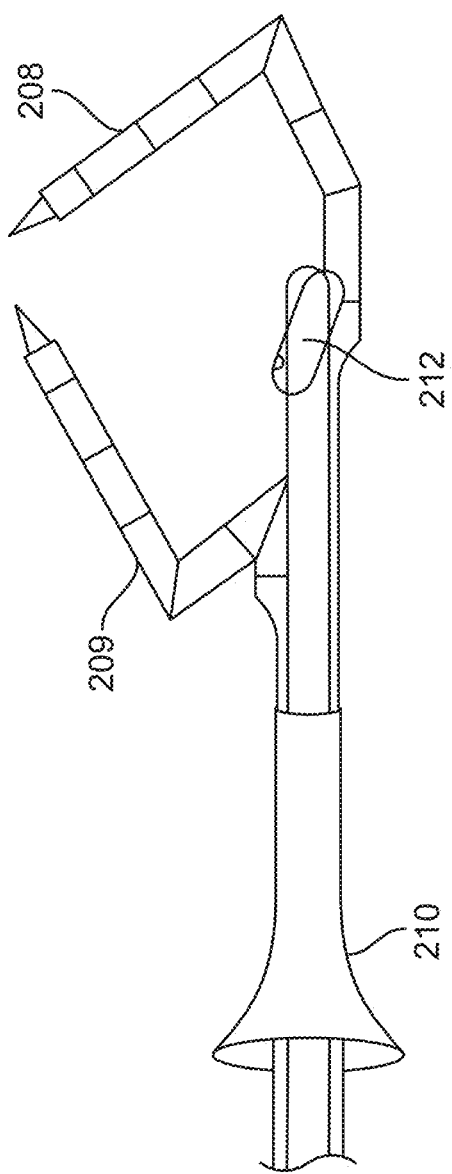
FIGS. 23-25 illustrate a first arm motor unit, a second arm motor unit, and a camera motor unit after insertion through a trocar, in accordance with some embodiments.
Figure 24:
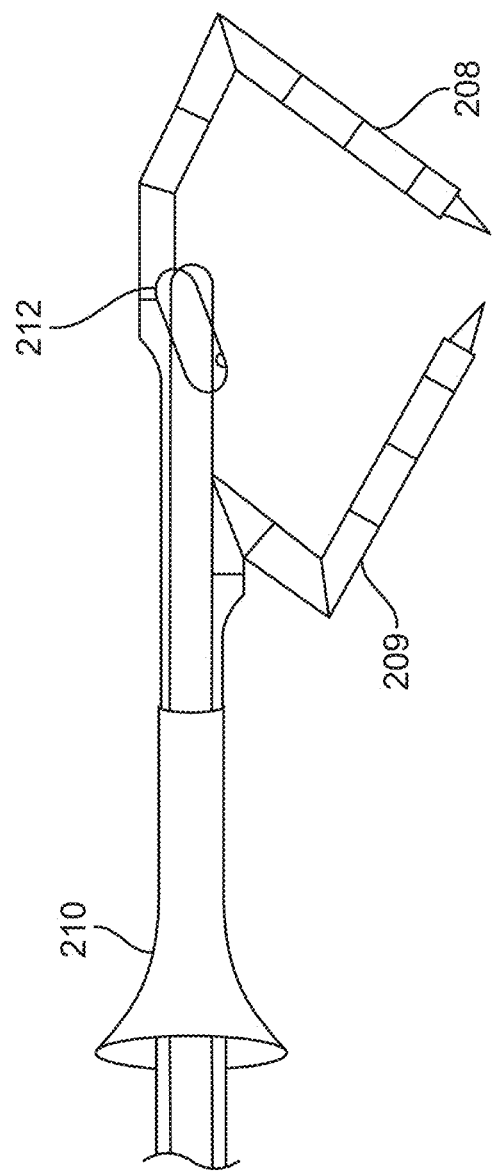
Figure 25:
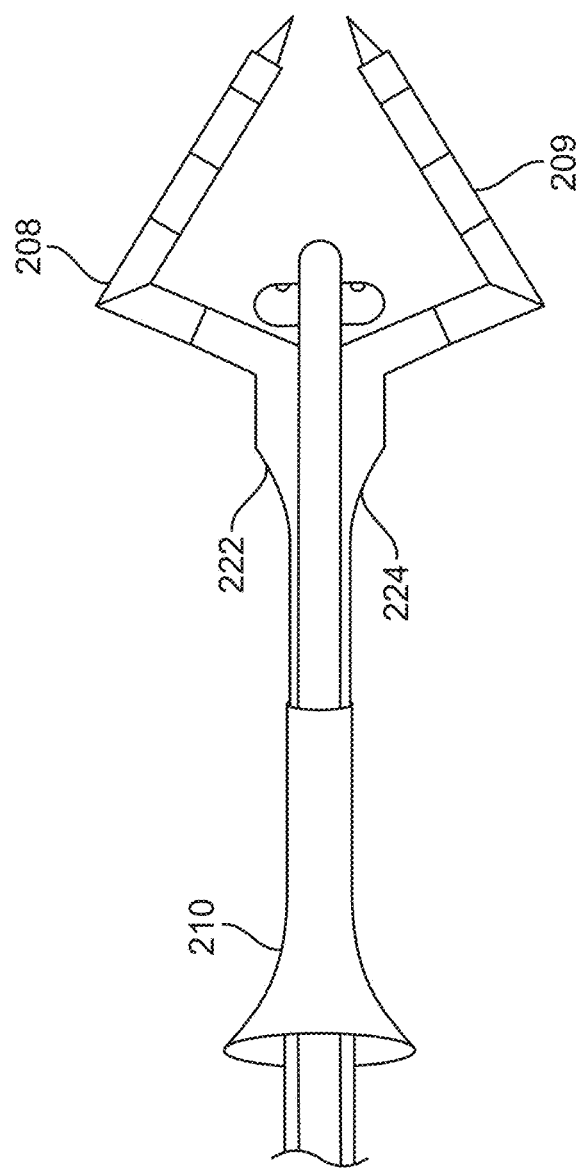

FIG. 16 illustrates a first working end 208 of a first arm MU and a camera MU working end 212 being inserted through a trocar 210. As shown in FIGS. 17-22, a transition element 222 for the first arm MU may guide the first working end 208 of the first arm MU through the trocar 210. Further, a transition element 224 for the second arm MU may guide the second working end 209 of the first arm MU through the trocar 210. The transition elements 222 and 224 for the first arm MU and the second arm MU may guide the first working end 208 of the first arm MU and the second working end 209 of the second arm MU through the trocar. As described above, the camera MU transition element may likewise guide the camera MU working end through the trocar 210 such that all three working ends are inserted through the trocar. FIGS. 23-25 shows the first working end 208 of the first arm MU, the second working end 209 of the second arm MU, and the camera MU working end 212 inserted through the trocar 210. The transition element 222 for the first arm MU and the transition element 224 for the second arm MU may also be inserted through the trocar 210.

After each robot assembly is inserted, the remaining cross-sectional area in the trocar 210 through which additional robot assemblies and/or other instruments can be inserted would decrease because the support tube of each robot assembly would occupy some space within the interior of the trocar 210. According to certain embodiments, this is illustrated in FIGS. 11-22. As such, to ensure that there is adequate space for the requisite robot assemblies or other instruments to be inserted into the operation site, robot assemblies or instruments with larger cross-sectional areas are inserted first, followed by bobot assemblies or instruments with smaller cross-sectional areas. One way to insert a set of instruments of different sizes is to insert the largest instrument first, followed by the second largest, followed by the third largest, and so on.

In some embodiments, where all robot assemblies or instruments have similar or identical cross-sectional areas or where all the cross-sectional areas of the robot assemblies or instruments are sufficiently small, the order of insertion can be based on other factors. In embodiments where the cross-sectional area of one of the robot assemblies or instruments is much larger than the others (such that it cannot be inserted if the others have already been inserted) the larger instrument should be inserted first. For example, if a camera robot assembly has such a large cross-sectional area that it cannot be inserted if the arm robot assemblies have already been inserted, the camera robot assembly should be inserted first.

According to some embodiments, this procedure is repeated for each robot assembly until all desired robot assemblies are inserted through the trocar 210 and into the patient. Once inserted into the patient, each robot assembly can be moved to a surgery ready position either at the direction of the surgeon or in an automated fashion. In some embodiments, the stereoscopic camera of the camera robot assembly is configured such that it is equidistant from the shoulder joint of each robotic arm and is thus centered between the arms. This alignment of the stereoscopic camera and the two shoulder joints is the virtual shoulder of the robot. In some embodiments, there are at least two robotic arms with at least 6 degrees of freedom, and at least one stereoscopic camera with 2 degrees of freedom allowing the robots to face and work in discrete directions (e.g., left, right or straight). In some embodiments, the robot can be configured to move continuously between multiple discrete positions to work in any desired positions (FIGS. 23-25). According to some embodiments, the continuous movement is achieved by changing the facing angle of the virtual shoulder of the robot. The facing angle is the direction defined by the center of the user's workspace at a given point in time. Another way to describe it is that the facing angle is the direction that a user would define as straight ahead of them. According to some embodiments, the facing angle of the virtual shoulder is controlled by adjusting the relative insertion depths of each robot and by simultaneously adjusting the angles of the joints of each robotic arm and the camera robot, such that a smooth transition is achieved.

After the insertion, the user can begin operating using the input device and HMD disclosed in U.S. Pat. No. 10,285, 765 B2. In some embodiments, the facing angle of the system can be adjusted by the user while operating such that it would appears to the user as if he or she is just rotating about a seat. According to some embodiments, this effect can be accomplished by incorporating certain user interface (UI) elements such as tracking the user's chair, pinch or click to drag and rotate world, buttons on hand controllers, etc. The areas in which the user can access the surgical environment and work is sometimes referred to as the workspace. This ability to rotate in place gives the user a larger workspace for a given trocar placement and thus allows more freedom to complete the procedure. Additionally, in some embodiments, the user can take advantage of the additional degrees of freedom provided by the RSS to move and pivot the robot assemblies throughout the surgical field, thereby further enhancing the usable workspace.

Once the user has completed the procedure, the robot assemblies need to be removed through the trocar 210. In some embodiments, the robot assemblies automatically move to a removal ready orientation. For example, the working ends of the robotic assemblies may be straightened such they are aligned with their axis of insertion. In some embodiments, the robot assemblies can be allowed to go slack. Once the robot assemblies are ready to be removed, in some embodiments, they are removed one by one by translating them backwards through the trocar 210. In one embodiment, as each robot assembly is moved towards the trocar 210, the transition element would contact the inner tip of the trocar 210 and guide the working end of the robot assembly to deflect radially inward relative to the trocar 210.

This allows the working end of the robot assembly to continue passing though the trocar 210. In this embodiment, after the working end passes through the trocar 210, the trocar wall guides the working end to un-deflect. At this point the robot assembly can be pulled back until it is fully removed. The user can now proceed with the removing the remaining robot assemblies until they are all removed. In other embodiments, the radial retraction motion within the trocar 210 can be achieved automatically or in a controlled fashion by incorporating additional actuated joints or mechanisms within the support tube of the robot assembly or within its corresponding MU or on the RSS.

In embodiments where all robot assemblies or instruments have similar or identical cross-sectional areas or where all the cross-sectional areas of the robot assemblies or instruments are sufficiently small, the order of removal can be based on other factors. In embodiments where the cross-sectional area of one of the robot assemblies or instruments is much larger than the others (such that it cannot be removed if the others have not yet been removed), the larger instrument is removed last.

In some embodiments, each MU is coupled relative to the others or may be one unified MU and the linear travel that may be required for insertion may be provided for by linear extension of each support tube of each robot assembly. In some embodiments, two MU's are linearly translatable relative to the third MU and the third MU can linearly translate relative to the RSS (see, e.g., FIGS. 7-9). In these embodiments, when the third MU translates, the other two MU's translate with it. In some embodiments, each MU is coupled to its own RSS and aligned independently.

There are several significant advantages of the setups detailed above. At the outset, the ability of the working ends to translate radially outward within the trocar creates space thus allowing for other instruments to be inserted through the same trocar (see, e.g., FIGS. 11-22). Additionally, once the robot assemblies are inserted, the workspace of the system can be moved to work on one side, straight on or on the other side simply by adjusting the relative depths of the robot assemblies, such as by adjusting the relative depth of the camera robot assembly and the two arm robot assemblies. Hence, allowing the user to access a greater area from a single insertion site. Furthermore, the insertion of the camera robot assembly and the arm robot assemblies, according to some embodiments, can be performed by inserting them in a straight line. And, in some embodiments, each robot assembly can be removed from the patient by retracting each assembly straight out.

Aspects of the subject matter described herein can be implemented in digital electronic circuitry, or in computer software, firmware, or hardware, including the structural means disclosed in this specification and structural equivalents thereof, or in combinations of them. Further, aspects of the subject matter described herein can be implemented using one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

It is contemplated that systems, devices, methods, and processes of the disclosure invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps.

It should be understood that the order of steps or order for performing certain action may be immaterial so long as the disclosure remains operable. Moreover, two or more steps or actions may be conducted simultaneously.

It is to be understood that the disclosed subject matter is not limited in its application to the details of construction and to the arrangements of the components set forth above or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter.

Magnetic Sensing Systems

In the following description, numerous specific details are set forth regarding the systems and methods of the disclosed subject matter and the environment in which such systems and methods may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are illustrative, and that it is contemplated that there are other systems, apparatuses, and/or methods that are within the scope of the disclosed subject matter.

While the present system/method is designed for tracking and sensing the orientation and actuation of a joint and/or joints of a miniaturized surgical robotic device, this system may be implemented in any device that utilizes magnets to track and/or sense the actuation and orientation of robotic Joints. The present system/method can also be implemented in any device or system that may require and/or utilize magnetic tracking and/or sensing when the currently available magnetic tracking and sensing systems are too large for the imposed geometric constraints.

A robotic assembly may comprise a magnetic sensing system, such as a magnetic sensing system for a robotic joint (such as a robotic joint of a cable-drive robotic arm). A robotic joint may be operatively coupled to a corresponding magnetic sensing system. A robotic joint may comprise a corresponding magnetic sensing system. The magnetic sensing system may be configured for sensing displacement or movement of the robotic joint.

A magnetic sensing system may comprise a magnet and a sensor. The sensor may be configured to sense a change in at least a portion of a magnetic field of the magnet. The magnetic sensing system may comprise a plurality of magnets and a plurality of sensors. A sensor may be configured to measure a change in at least a portion of a magnetic field of at least a portion of the plurality of magnets.

One or more magnets of a magnetic sensing system may be positioned in an arrangement. The arrangement of magnets may form a magnetic field. One or more sensors of a magnetic sensing system may be positioned in an arrangement. The arrangement of sensors may individually measure at least a portion of the magnetic field produced by the one or more magnets. An arrangement of sensors and magnets may be configured to optimize (i) space for a plurality of components (such as cables) to be housed or pass through a joint (such as a cable driven robotic arm), (ii) range of motion or movement of the joint, (iii) accuracy of a measurement of the magnetic sensing system, or (iv) any combination thereof.

An arrangement may include one or more magnets. An arrangement may include at least 2 magnets. An arrangement may include at least 4 magnets. Two or more magnets may be arranged substantially in a column. Two or more magnets may be arranged substantially within a single plane, such as 4 magnets arranged substantially within a single plane. An arrangement of magnets may comprise an array of magnets, such as 2×2 magnets, 2×3 magnets, 2×4 magnets, 3×4 magnets, 4×4 magnets, or others.

Magnets each having a N pole and a S pole may be arranged relative to each other in a number of different ways. Two magnets (such as magnets each arranged substantially in a different column) may be oriented with opposing dipoles to one another such that the first magnet is oriented N-S relative to the second magnet and the second magnet is oriented S-N relative to the first magnet. Magnets of a first column may be positioned so that their dipoles are oriented in an alternating orientation relative to dipoles of a second column, such as a first column oriented N-S, N-S and a second column oriented S-N, S-N. A magnet having a dipole of N-S may be positioned diagonally, obliquely, or transversely from a magnet with a dipole of S-N. A S pole of a magnet may directly face a N pole of a second magnet. A side of a magnet moving from a N pole to a S pole may directly face a side of a second magnet positioned to move from a S pole to a N pole.

Arrangement of the one or more magnets may form a magnetic field. A change in at least a portion of the magnetic field may be measured by one or more sensors. The magnetic field may comprise an orthogonal field component, a parallel field component, a non-parallel field component, or any combination thereof.

Magnets may be arranged within sections of the joint. For example, a joint comprising two magnets may have a first magnet positioned in a first half of the joint and a second magnet positioned in a second half of the joint. A joint comprising four magnets may have a first magnet positioned in a first quadrant of the joint, a second magnet positioned within a second quadrant of the joint, a third magnet positioned within a third quadrant of the joint, and a fourth magnet positioned within a fourth quadrant of the joint. This positioning of multiple magnets within subsections of the joint has be implemented with about 2, 3, 4, 5, 6, 7, 8, 9, 10 magnets or more within a single joint.

One or more sensors may form an arrangement of sensors substantially along a single plane. The plane of sensors may be positioned substantially perpendicular to one or more magnets or an arrangement of magnets. The plane of sensors may be positioned substantially parallel to one or more magnets or an arrangement of magnets. One or more sensors may form an arrangement of sensors along more than one plane. An arrangement of sensors may comprise an array of sensors, such as 2×2 sensors, 2×3 sensors, 2×4 sensors, 3×4 sensors, 4×4 sensors, or others.

A plane of sensors (such as positioned substantially perpendicular to an arrangement of magnets) may be positioned between two or more magnets. A plane of sensors may be positioned outside of the arrangement of magnets. A plane of sensors may be positioned between a first magnet of a column and a second magnet of the column. A plan of sensors may be positioned between a first magnet of a first column and a second magnet of a second column.

One or more magnets of the magnetic sensing system may be positioned substantially to a peripheral edge of the robotic joint. One or more sensors may be positioned substantially distal to a central location of the robotic joint. One or more sensors of the magnetic sensing system may be positioned substantially to a peripheral edge of the robotic joint. One or more magnets may be positioned substantially distal to a central location of the robotic joint.

Arrangement of the magnet and sensor of the magnetic sensing system may provide measurement of robotic joint displacement with a higher resolution as compared to a comparable robotic joint lacking the arrangement. The higher resolution may be about 1.1×. 1.2×, 1.3×, 1.4×, 1.5×, 1.6×, 1.7×, 1.8×, 1.9×, 2.0× greater or more.

Arrangement of the magnet and sensor of the magnetic sensing system may provide measurement of robotic joint displacement with a higher accuracy as compared to a comparable robotic joint lacking the arrangement. The accuracy of measurement may be at least about 70%, 80%, 85%, 90%, 95%, 96%, 97%, 98%, 99% or more accurate.

The virtual diametric magnet system disclosed herein may be designed to be incorporated in and/or utilized with the robotic arms disclosed in U.S. Pat. No. 10,285,765 B2 titled Virtual Reality Surgical Device, and/or the wrist assemblies disclosed in International Patent Application No. PCT/US2018/60656 (published as International Patent Application No. WO2019094896A1) titled Virtual Reality Wrist Assembly, according to some embodiments. Both references are attached in the appendix and are herein incorporated in their entirety. In some embodiments, the virtual diametric magnet system can also be implemented and utilized by other existing and future surgical robotic systems or devices.

As used herein, a magnet at least includes an object or collection of objects capable of generating a magnetic field, including but not limited to Neodymium, Iron, and other formulations of permanent magnets, electromagnets, and/or any other objects capable of generating magnetic fields.

As used herein, a sensor includes an object or collection of objects capable of measuring magnetic field strength, or capable of measuring some quantity from which magnetic field strength can be derived, including but not limited to, integrated circuits (ICs), MEMS systems, discrete electronic components, mechanical transducers, purely mechanical computational machines, and/or any other objects known in the art capable to measure or transduce magnetic fields.

As used herein, a joint includes an object or collection of objects capable of relative displacement, either translational or angular.

As used herein, a sensor array includes a single sensor, or a collection of sensors, positioned relative to a magnet and each other such that the sensor is positioned to measure one or more components of the magnetic field that vary with joint displacement.

Figure 26:
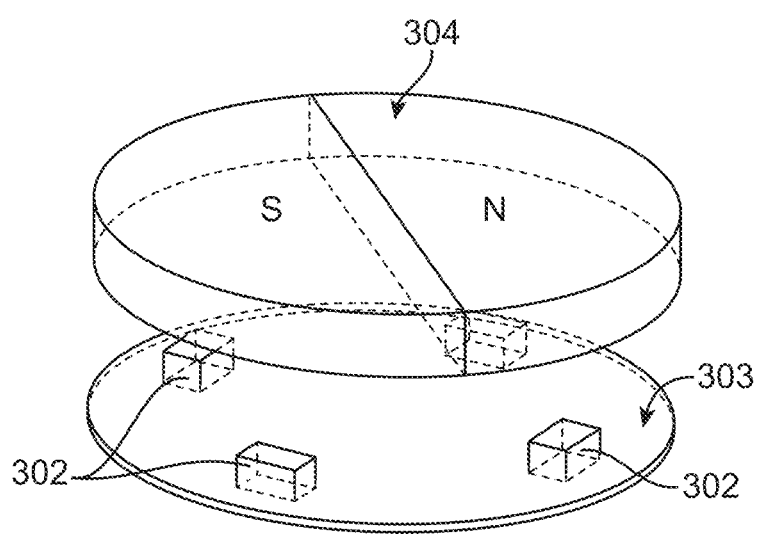
FIGS. 26 and 27 illustrates a system comprising a sensor array and a rotating magnet, in accordance with some embodiments.
Figure 28:
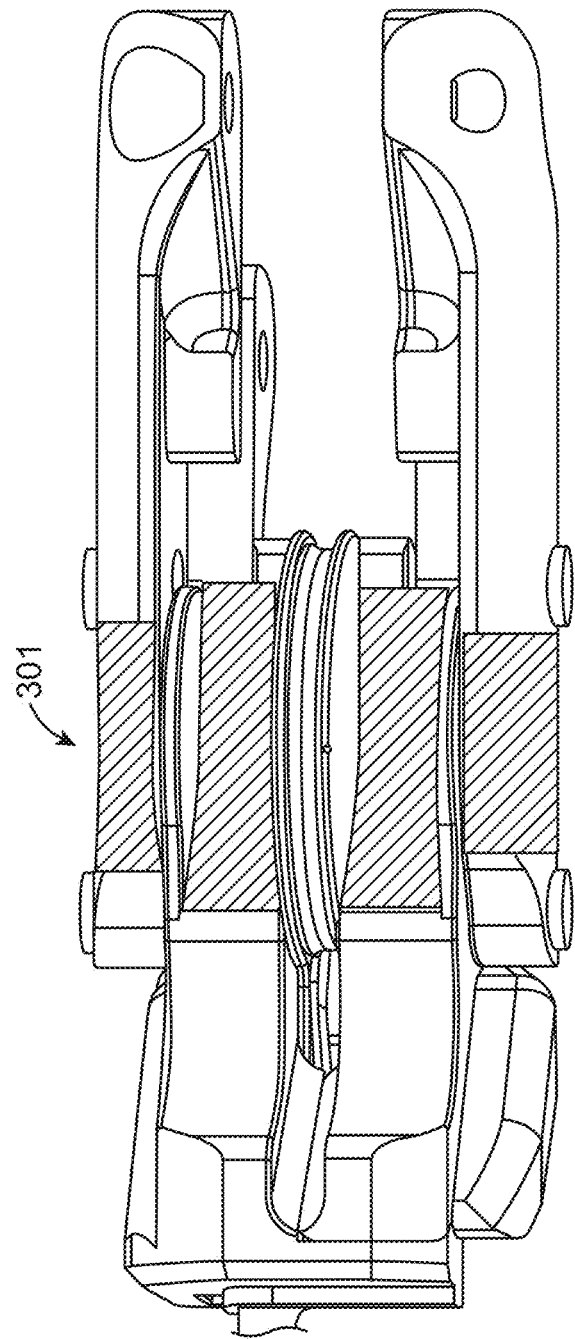
FIG. 28 illustrates a robotic joint assembly, in accordance with some embodiments.

As stated above, the system disclosed herein has been designed to be incorporated and utilized with the robotic arms disclosed in U.S. Pat. No. 10,285,765 B2 according to some embodiments. FIG. 28 shows a robotic joint 301 according to certain embodiments. The robotic joint 301 shown in FIG. 28 is a cable-driven joint. FIG. 28 illustrates the regions of the robotic joint 301 that are reserved for other components of the joint and thus cannot be used for the sensing components. According to some embodiments, the hatch areas illustrated in FIG. 28 are used by the drive cables of distal joints, or by the bearings that carry cable loads to provide smooth motion of the robotic arm. Due to the constraints imposed by a cable-driven robotic joint, there is an insufficient amount of free space for implementing any of the previously discussed standard magnetic sensing solutions. In FIG. 28, the available space in the center of the joint 301 is less than about 1 millimeter (mm) thick by about 5 mm in diameter, which is insufficient to generate a magnetic field with acceptable strength using currently available Magnets. Additionally, placing one or more sensors 302 in the interior space and positioning the magnet outside of the interior space, as illustrated in FIG. 26, will also not work due to the constraints of the robotic joint design. A set of bearings which lie on the axis of rotation at the outer extremes of the joint precludes the use of sufficiently large disc shaped magnets. Furthermore, the bearings may be supported structurally in about 360 degrees, and have large unidirectional loading which precludes the use of a large toroidal shaped magnet.

Figure 27:
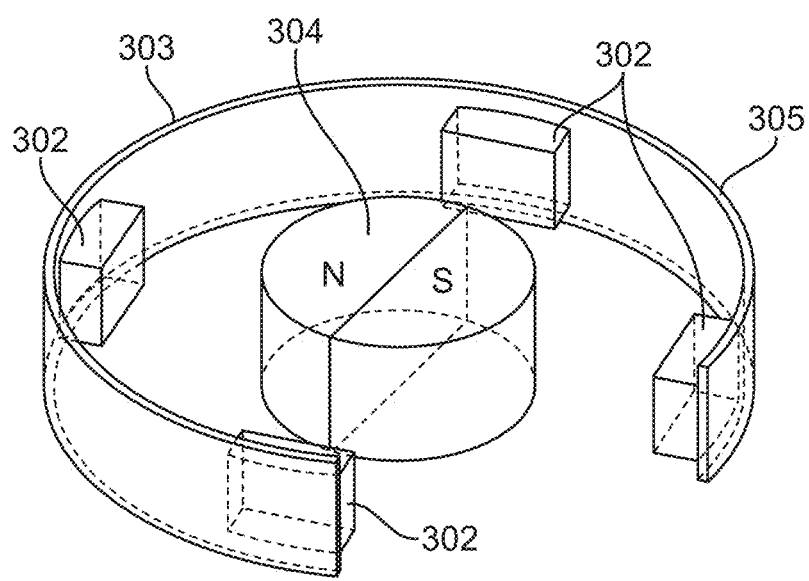

FIG. 26 is an isometric view of a system which places a sensor array 303 at the axis of a rotating magnet 304 separated axially by a distance. The sensor array 303 may comprise one or more sensors 302. FIG. 27 is an isometric view of a system which places a sensor array 303 on or near the plane through the center of a magnet 304 and perpendicular to the axis of rotation. The arrangements of the sensors 302 and magnets 304 shown in FIG. 26 and FIG. 27, may be limited to where they can be placed in a robotic joint due to the volume of space these arrangements may require, and thus may limit the design of a joint. The system may further comprise a flexible printed circuit board (PCB) 305 that extends around a circumferential portion of the system.

The system disclosed herein is generally directed to an arrangement of magnets and sensor array, such that their spacing and relative location provide sufficient space for numerous amounts of cables to be routed through the center of a joint, while allow for accurate sensor readings of the orientation and actuation of the joint. According to certain embodiments, the arrangement of magnets and sensor array of the system disclosed herein allows for magnetic energy to be distributed throughout the available space in a joint. In a way, the arrangement provides a simple and repeatable way of recovering joint displacement information with high resolution.

Figure 29:
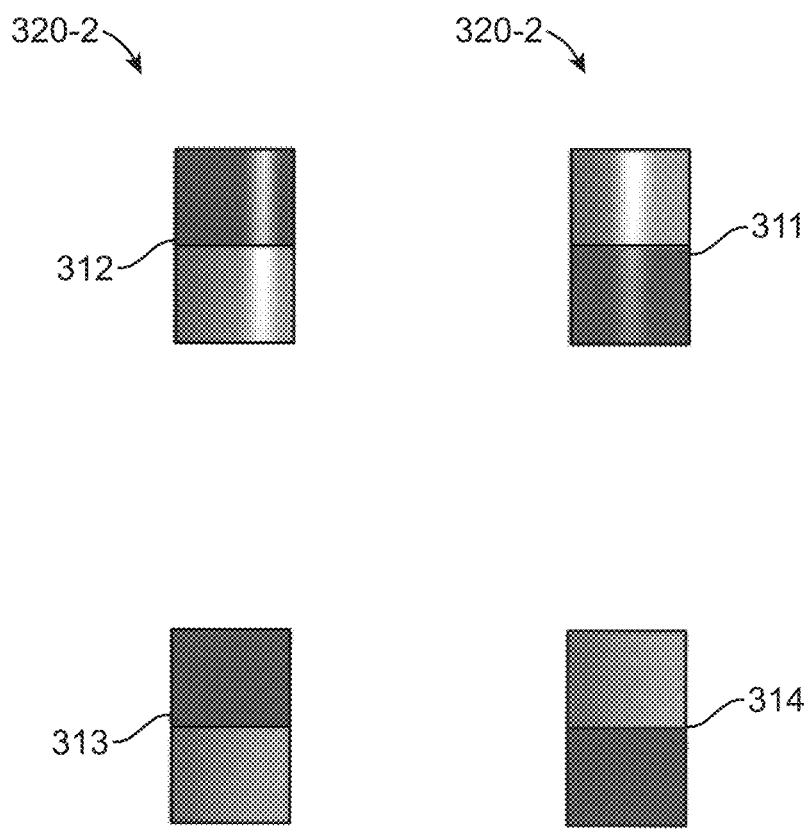
FIG. 29 illustrates an arrangement of magnets, in accordance with some embodiments.
Figure 30:
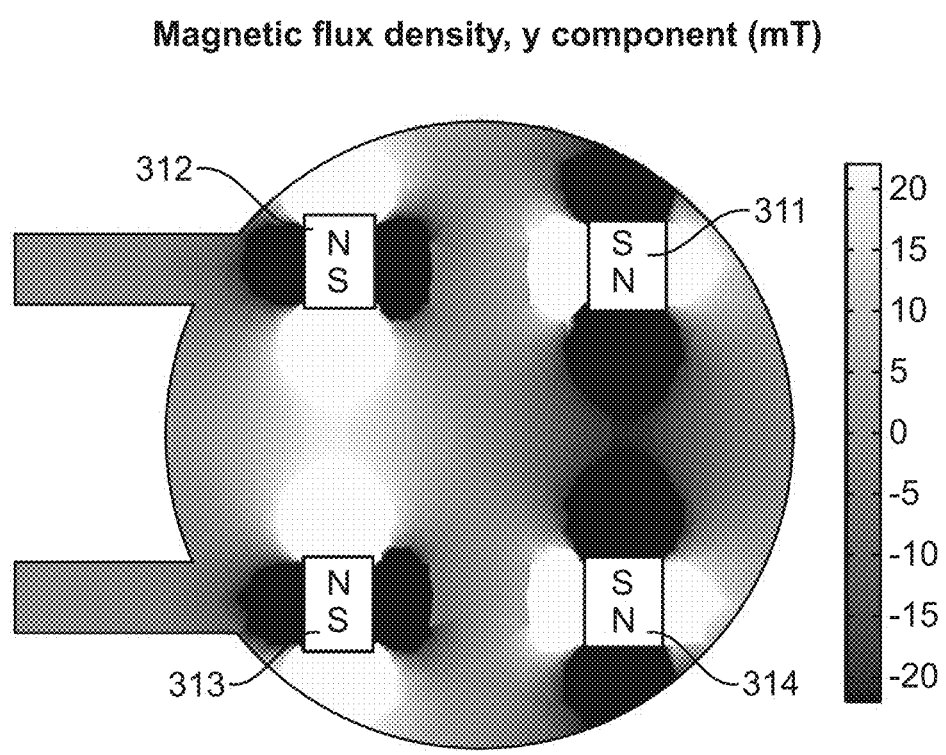
FIG. 30 illustrates a simulation of a magnetic field generated by an arrangement of magnets, in accordance with some embodiments.

FIG. 29 is a profile view of an arrangement of magnets 311, 312, 313, 314 of the system according to some embodiments. In FIG. 29, there are two columns of magnets 320-1 and 320-2. Column 1 (320-1) is comprised of magnet 1 (311) and magnet 4 (314), and column 2 (320-2) is comprised of magnet 2 (312) and magnet 3 (313). Column 1 (320-1) and column 2 (320-2) are a fixed distance apart from each other and each column is separated into two parts to create four quadrants. As seen in these embodiments, instead of using a single magnet near a sensor, a set of four magnets are arranged in quadrants, with magnetization directions aligned between magnet 1 (311) and magnet 4 (314), and magnetization directions aligned between magnet 2 (312) and magnet 3 (313). Additionally, in this embodiment, the magnetization direction between magnet 1 (311) and magnet 4 (314) is opposite of the magnetization direction between magnet 2 (312) and magnet 3 (313). FIG. 30 shows a simulation of the resulting field generated by the arrangement illustrated in FIG. 29. In some embodiments, the set of four magnets 311, 312, 313, 314 are neodymium permanent magnets.

Figure 32:
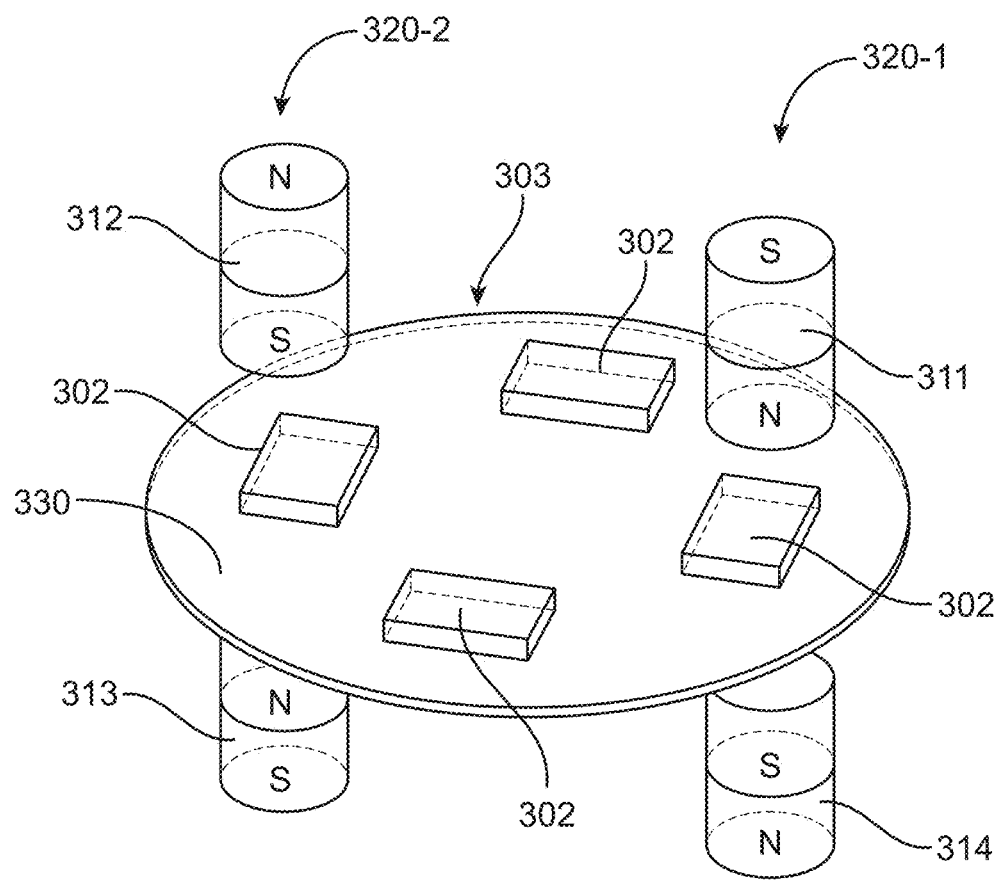
FIG. 32 illustrates a plurality of magnets and a sensor array for sensing a magnetic field generated by the plurality of magnets, in accordance with some embodiments.

As illustrated in FIG. 32, a sensor array 303 in the plane perpendicular to column 1 (320-1) and column 2 (320-2) occupies the space separating each column, sensing the field flowing from one magnet of one column to the corresponding magnet in the same column according to certain embodiments. In some embodiments, the components of the magnetic field sensed by the sensor array 303 may be orthogonal field components at a given point in space, individual parallel or non-parallel field components at varying points in space, or any combinations thereof. The data gathered by the sensor array 303 may then be used to infer the joint displacement, either by the one or more sensors 302 or via a remote calculation. The one or more sensors 302 may be disposed on a surface of a printed circuit board (PCB) substrate 330. According to certain embodiments, the result of the calculation is the same if one considers the magnet stationary and the sensor array 303 to be moving, or vice versa.

Figure 31:
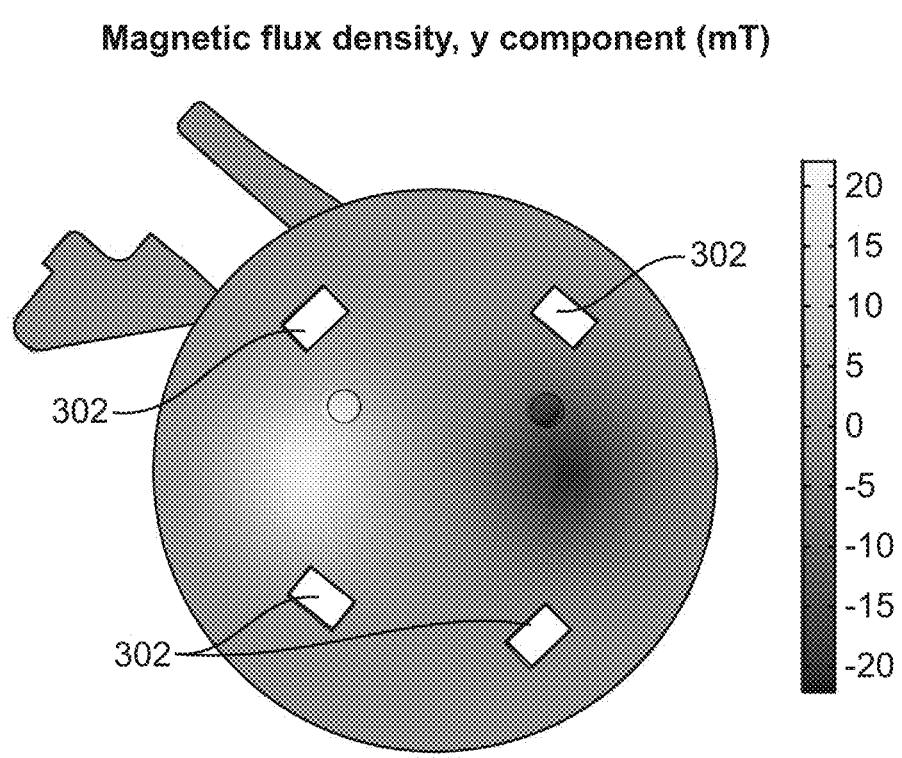
FIG. 31 illustrates a perpendicular component of the magnetic field generated by an arrangement of magnets, in accordance with some embodiments.
Figure 33:
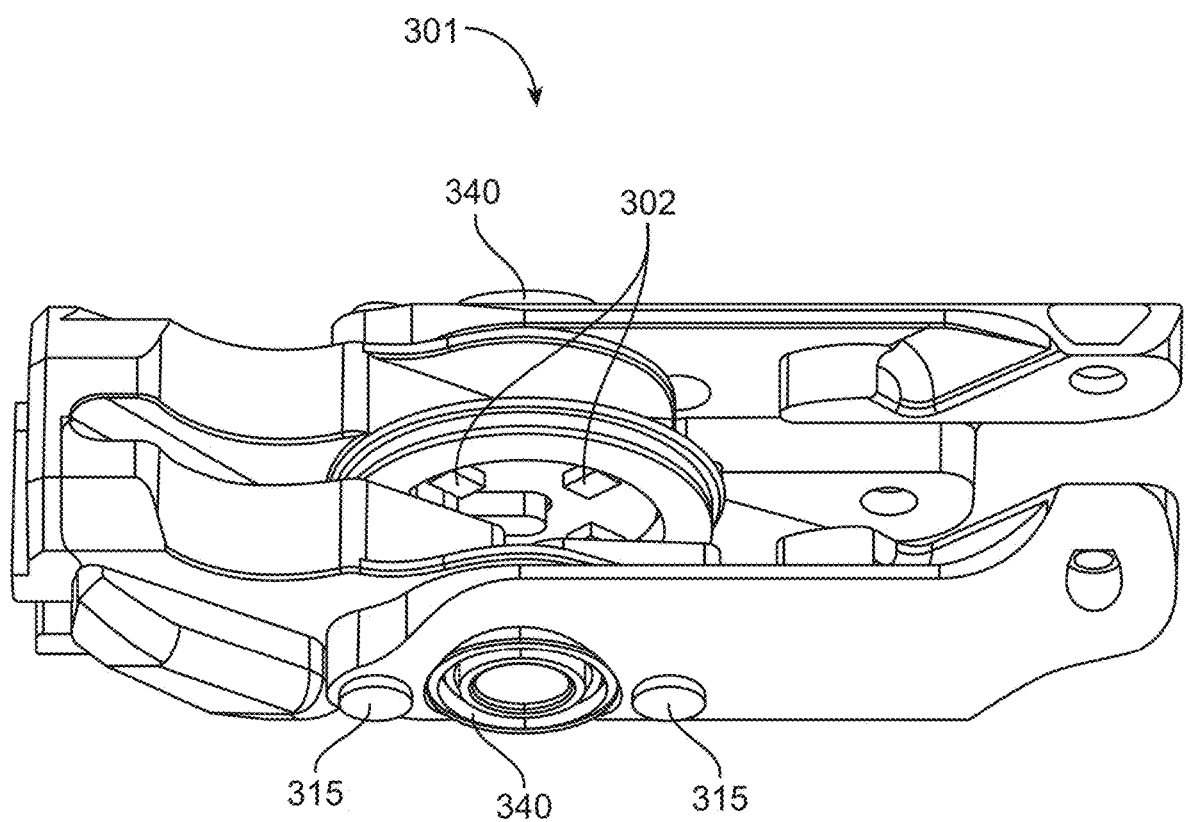
FIG. 33 illustrates a sensing system implemented in a joint, in accordance with some embodiments.

Referring back to FIG. 32, the sensors 302 closer to column 1 (320-1) sense the magnetic field generated by the magnets 311 and 314 of column 1 (magnets 1 and magnet 4), while the sensors 302 closer to column 2 (320-2) sense the magnetic field generated by the magnets 312 and 313 of column 2 (magnets 2 and magnets 3). The sensing read of this arrangement is illustrated in the simulation result shown in FIG. 31. FIG. 31 shows the perpendicular component of the magnetic field at the plane of the sensor array 303 between column 1 (320-1) and column 2 (320-2). As described above, the sensor array may comprise one or more sensors 302. In some embodiments, the exact spacing of the columns and the spacing between the magnets 311, 312, 313, 314 which makes up the columns may differ substantially based on the strength of the magnets, and/or the geometry and design specifications of the joint. The arrangement illustrated in FIG. 32 allows for a relatively slim plane of sensors 302 to be located in or near the center of a joint, while providing ample usable space throughout the center volume of the joint with several magnets located at the periphery of said joint. FIG. 33 shows an illustrative embodiment of the sensing system as implemented in a joint 301. As seen in FIG. 33, there is limited volume available for a sensing system, thus one or more magnets 315 are placed at the extremes of the joint 301 and the sensors 302 are centrally located. With this arrangement, numerous cables which drive distal joints can pass through the joint 301, allowing for smooth motion by integrating space for rolling-element bearings 340, and providing accurate sensing for closed-loop control of the joint's angular displacement.

Aspects of the subject matter described herein can be implemented in digital electronic circuitry, or in computer software, firmware, or hardware, including the structural means disclosed in this specification and structural equivalents thereof, or in combinations of them. Further, aspects of the subject matter described herein can be implemented using one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

It is contemplated that systems, devices, methods, and processes of the disclosure invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps.

It should be understood that the order of steps or order for performing certain action may be immaterial so long as the disclosure remains operable. Moreover, two or more steps or actions may be conducted simultaneously.

It is to be understood that the disclosed subject matter may not be limited in its application to the details of construction and to the arrangements of the components set forth above or illustrated in the drawings. The disclosed subject matter may be capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter.

Positioning of Electrical Communication Components within a Joint

In the following description, numerous specific details are set forth regarding the systems and methods of the disclosed subject matter and the environment in which such systems and methods may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are illustrative, and that it is contemplated that there are other systems, apparatuses, and/or methods that are within the scope of the disclosed subject matter.

While the present system/method is designed for routing electrical communication components through joints of a multiple degrees of freedom miniaturized surgical robotic device, this system/method can be implemented in any device desiring accurate sensing of the position and orientation of joints without limiting the motions of the joints.

The system/method disclosed herein, according to some embodiments, can be incorporated and utilized with the robotic arms disclosed in U.S. Pat. No. 10,285,765 B2 titled Virtual Reality Surgical Device, or with the wrist assemblies disclosed in International Patent Application No. PCT/US2018/60656 (published as International Patent Application No. WO2019094896A1) titled Virtual Reality Wrist Assembly, or with the camera system disclosed in U.S. patent application Ser. No. 16/130,734 titled Virtual Reality Surgical Camera System. The aforementioned references are attached in the appendix and are herein incorporated in their entirety. In some embodiments the system/method disclosed herein can be implemented and utilized by other existing and future surgical robotic systems or devices.

In a complex multi-degree of freedom system, having a continuous electrical communication component is not always feasible from an assembly or manufacturing standpoint. In some instances, to deal with the spatial constraints, multiple electrical communication components are utilized with the electrical communication components operably coupling to each other. Each communication component is designed such that it can be placed in a device whether or not the device is already assembled. This allows for ease of repair in the event of a failure or during repurposing after an operation. As the number of degrees of freedom increases, the amount of data increases as well, as each joint is independently sensed. Microcontrollers along the electrical communication components allow the data gathered at each sensor to be processed and retransmitted in such a way that the number of electrical conductors per component can be reduced. This allows for many sensors to be placed in a chain of electrical communication components with fewer number of conductors. As a result, the width or thickness of the electrical communication components will not be too large.

According to some embodiments, the systems disclosed herein are used to route electrical communication components through an eight degrees of freedom surgical robotic device that has position sensing elements to provide a closed loop control of each joint of the robotic device. The systems are configured to ensure the control input from the control system is achieved accurately and precisely. In some embodiments, different electrical communication components may be utilized, including but not limited to flexible printed circuit boards ("FPCB"), fiber optic cables and/or other communication elements known in the art capable of transmitting and receiving electrical signals.

Various methods for routing electrical communication components through different types of robotic joints and actuators are disclosed herein. Some examples of robotic joints are described in the aforementioned patent and patent application, including but not limited to hinge joints/actuators and rotary joints/actuators. According to some embodiments, the disclosed routing methods allow electrical signals and communications such as hall effect sensor readings and camera sensor readings to pass from a distal portion of a device to a control system or vice versa. In some embodiments, the electrical communication components have one or more moving sections, designed to move with respect to the motion of one or more robotic joints. To avoid fatiguing the electrical communication components, as they pass through each joint, the moving sections of the electrical communication components are designed to have as large of a radius of curvature as possible and to have any bending occur over multiple regions rather than over a single point. In some embodiments, the moving sections are constructed as coils of flexible circuits, wrapped around the axis of the joint or about another point. In some embodiments, the moving sections can be folded in half in a linear motion, where the two ends of the electronic communication component are fixed to two different bodies, and the folding (or bending) portions move relative to the fixed ends. In some embodiments, the moving sections are constructed as coils as discussed above with moving sections which can be folded in half. These disclosed systems/methods facilitate the transmission data out of a dynamic system without impacting the rest of system.

A robotic arm of a robotic system may comprise one or more joints. A joint of the robotic arm may comprise at least a portion of an electrical communication component. The electrical communication component may comprise a portion of which passes through the joint and operatively ends to two end points, such as operatively connecting an end effector with an origin of the robotic arm or operatively connecting an end effector (such as a surgical tool) with a control system. The electrical communication component may be configured to transmit one or more electrical signals to or from a portion of the robotic arm. The electrical communication component may be configured to transmit one or more electrical signals to or from a joint of the robotic arm. The portion of the electrical communication component may move during actuation or movement of the joint to permit range of motion of the joint, to prevent substantially bending, folding or damage to the portion, or a combination thereof. An arrangement of the portion to permit movement of the portion as the joint moves may preserve range of motion of the joint and protect the portion against damage to the electrical components from bending or distortion. During movement of a portion of the joint, an arrangement of a portion of the electrical communication component may be configured to substantially maintain a radius of curvature, such as by wrapping or forming a moving bend. An arrangement may comprise a wrapping arrangement, a moving bend arrangement or others. Additional elements that may assist in preventing damage to a portion of the electrical communication component may include incorporating a stopping element into a portion of the robotic arm to limit a range of motion of at least a portion of the robotic arm. A stopping element may at least partially limit an overextension or over-compression of a portion of the electrical communication component. Incorporation of a coating or a film that covers at least a portion of the electrical communication component may prevent damage to at least a portion of the electrical communication component. The coating or film may comprise a lubricant.

At least a portion of the electrical communication component within the joint may be wrapped around an axis of the joint (such as a rotary joint), to form at least a partial helical wrap or at least a partial coil. The number of wraps may be positioned within a housing of a joint. The number of wraps may be positioned outside of a shaft of a joint. The number of wraps may be positioned between an inner wall of a housing and an outer wall of a shaft of the joint. The number of wraps of the portion may vary as a joint moves. The number of wraps of the portion may vary proportionally to a range of motion of the joint. At a first range of motion of a joint, the number of wraps may be maximized. At a second range of motion of the joint, the number of wraps may be minimized. The number of wraps may be tightly wrapped around an axis of the joint (such as the shaft). The number of wraps may be expanded outwardly toward in inner wall of a housing and loosely wrapped around the shaft. During movement of the joint, the wrapping of the electrical component may be maintained with the number of wrapping varying. Joints having a wrapping of the electrical component may be a rotary joint or a hinge joint. Joints having the wrapping may be a rotary joint.

At least a portion of the electrical communication component may be extended within the joint (such as a hinge joint) to form a moving bend. During actuation of the joint, at least a portion of the moving bend may move. During actuation of the joint, at least a portion of the moving bend may move proportionally to a range of motion of the joint. Joints having a moving bend may be a rotary joint or a hinge joint. Joints having a moving bend may be a hinge joint.

A moving bend may be positioned outside of the joint. The moving bend may be positioned within a portion of the joint—such as a housing. The moving bend may be positioned within a channel of the housing. At least a portion of the channel may be physically separated from the joint. The channel may be positioned outside of a central axis of the joint. During movement of the joint, the amount of the moving bend positioned within the channel may vary. The amount of the moving bend positioned within the channel may vary proportionally to a range of movement of the joint. For example, at a first range of motion of the joint, a minimum amount of the moving bend may be positioned within the channel. At a second range of motion of the joint, a maximum amount of the moving bend may be positioned within the channel. The moving bend may fold upon itself and extend to accommodate different amounts of the moving bend within the channel.

Figure 34:
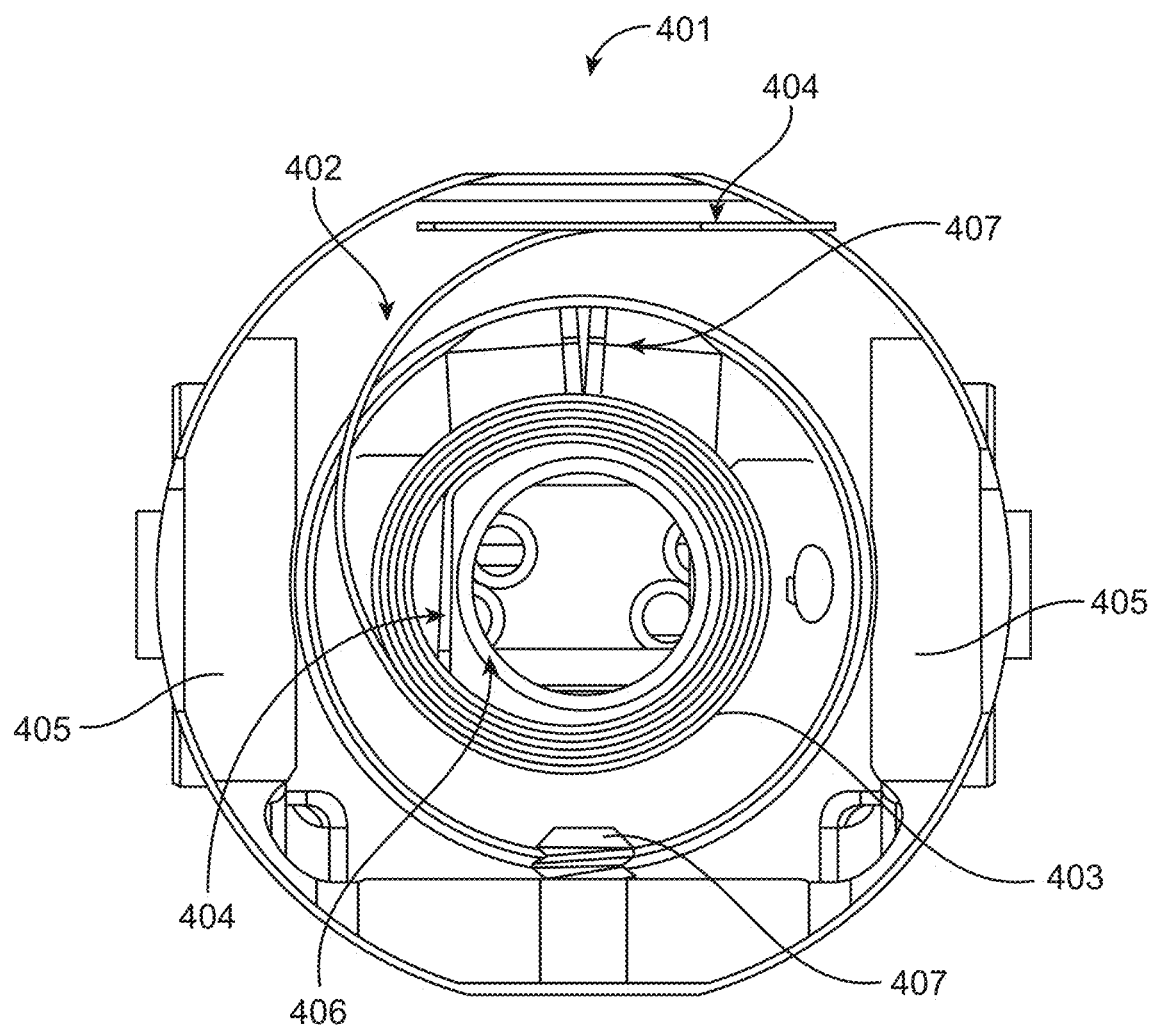
FIGS. 34 and 35 illustrate a rotary joint with a flexible printed circuit board wrapped around an axis of the joint, in accordance with some embodiments.
Figure 35:
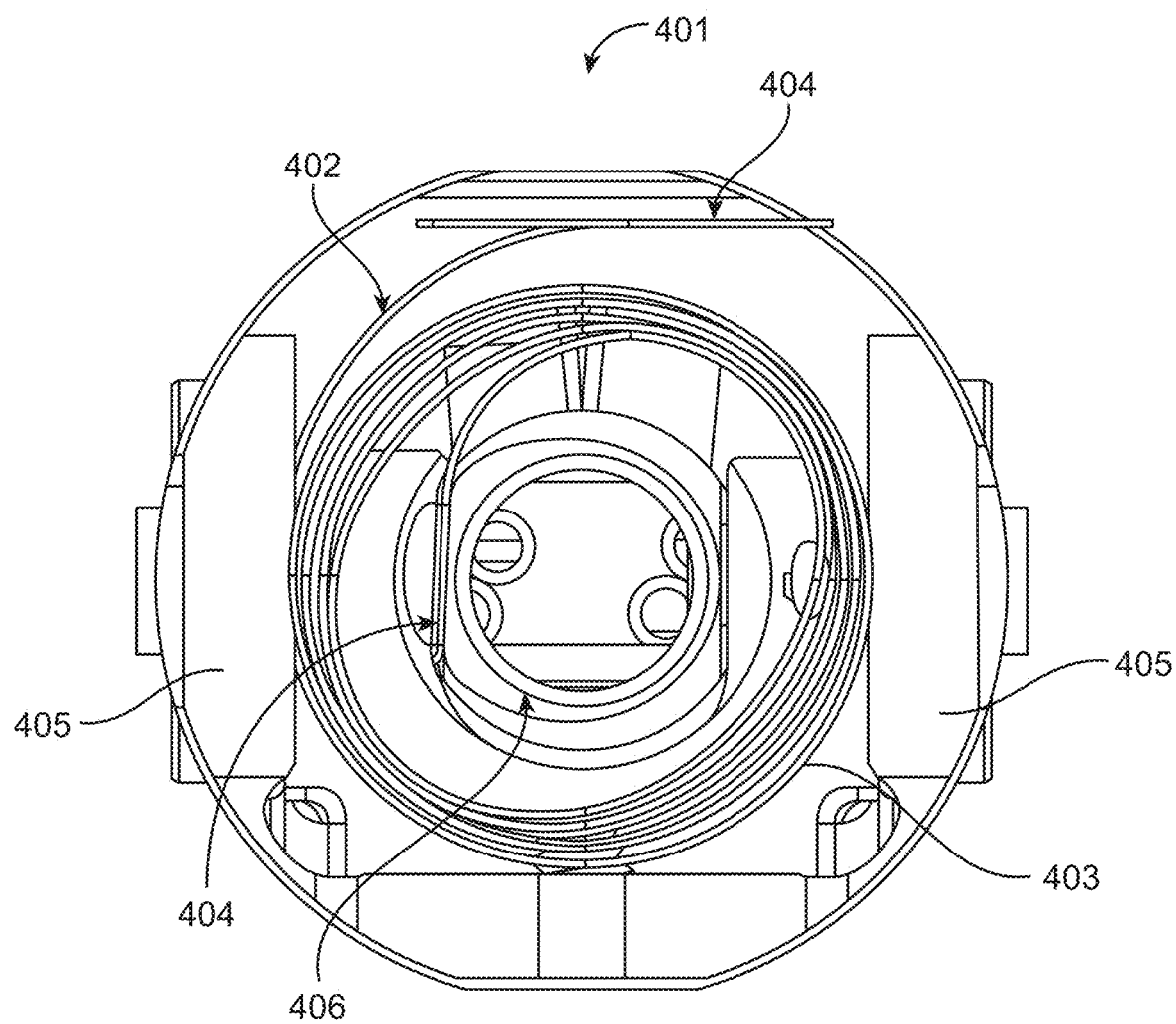

Different methods may be utilized to route electrical communication components through different types of robotic joints. FIGS. 34-35 show an embodiment of a rotary joint 401 with a FPCB 402 wrapped around the axis of the joint 401. In this embodiment, the FPCB 402 (or electrical communication component) is fabricated with a long section (also referred to as the rotary coil portion 403) and two short sections perpendicular to the long section. During actuation of the device, the long section is coiled around the axis of joint 401, with the number of wraps of the long section being dependent on the desired motion of the joint 401. The two short sections protrude into the distal and proximal portion of the joint 401, where they remain as stationary portions 404 relative to their respective housings 405, either distal or proximal. On each end, the two short sections expose solder pads for connecting to another FPCB, thus allowing the FPCBs to be connected, creating a chain to increase the length of data transmission, as well as for ease of assembly. In this embodiment, the rotary coil portion 403 of the FPCB 402 sits between two parts, one acting as a shaft 406, the other as a housing 405. When the joint 401 is at one extreme of its range of motions, the rotary coil 403 is wrapped tightly around the shaft 406, with a maximum number of wraps (FIG. 34), and at the other extreme of its range of motions, the rotary coil 403 is expanded as much as possible against the housing 405, with the minimum number of wraps (FIG. 35). The range of motions can be as little or as much as desired. In some embodiments, the rotary joint 401 may include a hard stop 407 to limit the range of motion. In these embodiments the hardstep 407 prevents the electrical communication component from over or under wrapping around the shaft 406 of the joint 401, thereby preventing tearing or bowing out of the electrical communication component. Additionally, in some embodiments, in order to reduce friction between the wraps of the coil 403 and between the coil 403 and the housing 405, the coil 403 is coated with a lubricant, such as dielectric grease. In some embodiments, a Teflon™ film is applied to the coil 403. In some embodiments, the housing 405 contains a Teflon™ coating or a diamond like coating to help reduce frictions during actuation of the joint 401, as well as to reduce the chance of only one portion or segment of the coil 403 expanding or contracting thus limiting the chance of the bowing out and/or tearing of the electrical communication component.

Figure 38:
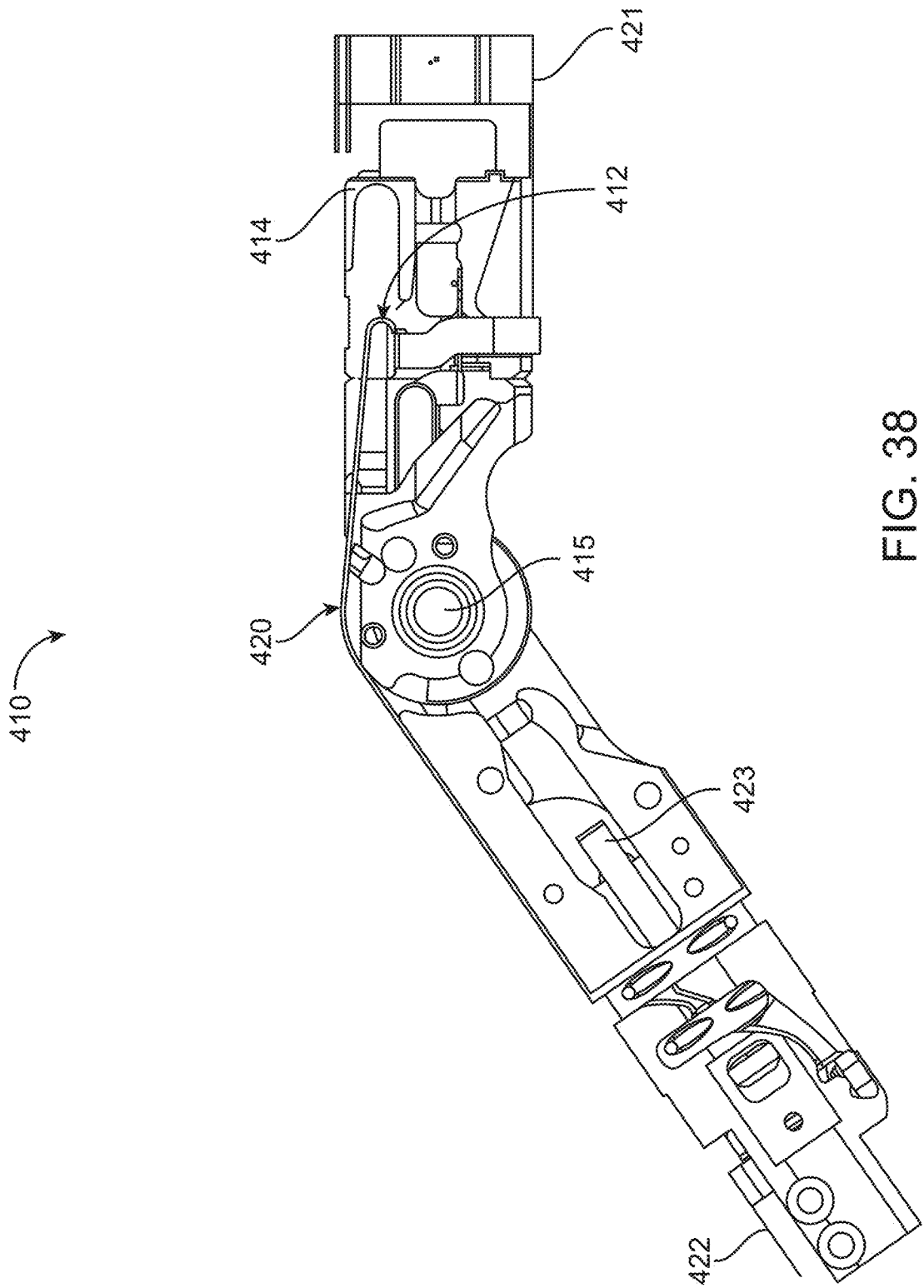
FIGS. 38 and 39 illustrate a hinge joint with an electrical communication component routed through the joint, in accordance with some embodiments.
Figure 39:
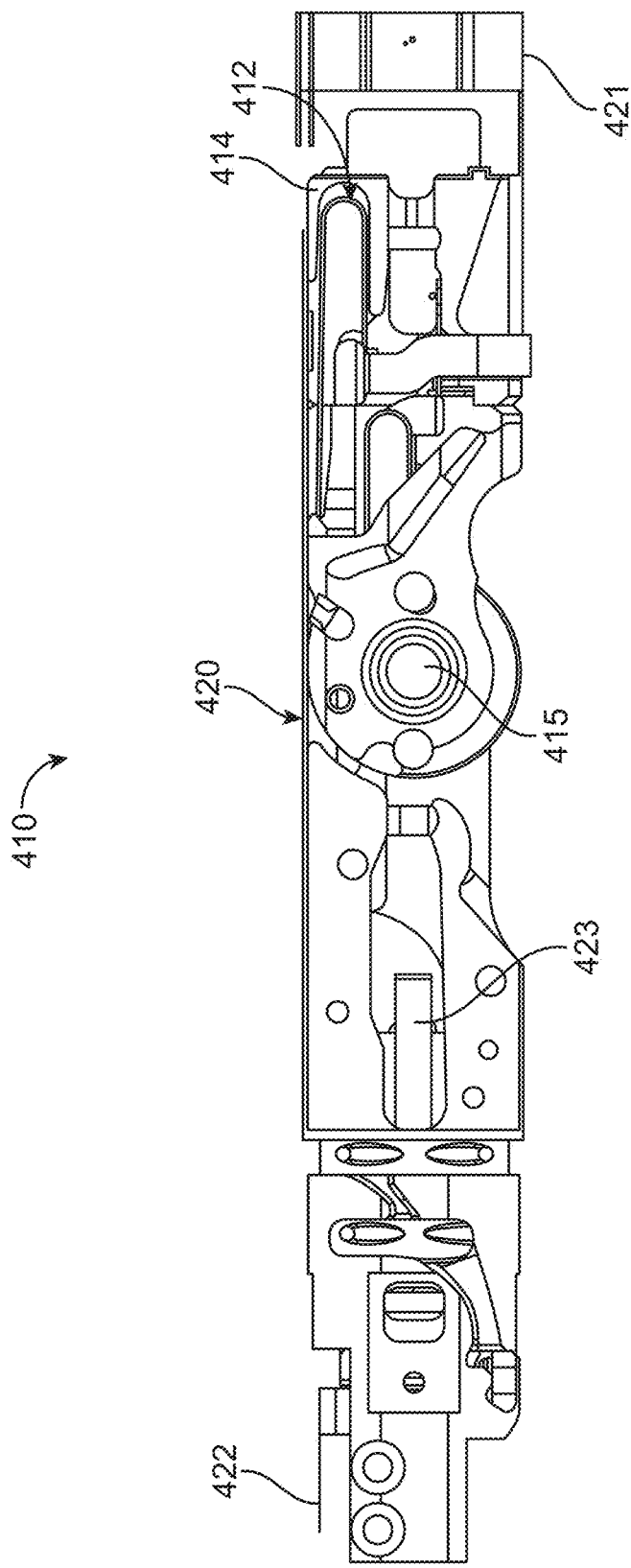

FIGS. 38-39 show an embodiment of a hinge joint 410 with an electrical communication component being routed through it. The electrical communication component may comprise an FPCB 420. Unlike the rotary joint discussed above, where the mechanical drive cables pass along/parallel to the axis of the joint, the mechanical drive cables in this hinge style joint 410 run perpendicular to the axis of the joint 410 thus may require a different routing technique. In this embodiment, the electrical communication component does not coil around the axis of the hinge joint 410 but instead passes outside of it and extends along a moving bend 412 situated within the Housing (channel) 414. During actuation of the joint 410, the moving bend 412 moves along the channel 414 such that at one extreme the moving bend 412 is close to the exit of the channel 414 (closer to the Axis 415) with a minimum amount of the electrical communication component within the channel 414 (FIG. 38). At the other extreme, the moving bend 412 is moved towards the base of the channel 414 (away from the Axis 415) with a maximum amount of electrical communication component within the channel 414 (FIG. 39). The hinge joint 410 may be configured to move a distal end 421 of a rotary FPCB relative to a proximal end 422 of the rotary FPCB. The proximal end 422 may be stationary during a movement of the distal end 421. The hinge joint 410 may be configured to move the distal end 421 of the rotary FPCB relative to a stationary portion 423 of the proximal end 422 of the rotary FPCB.

In some embodiments, passive and/or active retraction elements are used to ensure the electrical communication component bends in an expected manner during contraction. In some embodiments, an elastic element with low stiffness is coupled to one end of a mechanical housing of the joint and to the electrical communication component. During flexion of the joint, the moving bend 412 of the electrical communication component travels within the housing or channel 414, elongating the elastic element, creating a restoring force on the electrical communication component and to the hinge joint 410 which the joint 410 overcomes. During extension of the joint 410, the elastic element asserts a pulling force on the electrical communication component thus overcoming any frictional or bowing out forces, restoring the communication component to its original position in the channel 414. In some embodiments, the elastic element is fabricated as a rubber band or similar material. In some embodiments, a constant force spring or an actively controlled actuator is used.

In some embodiments, the motion of the joint itself dictates the position of the electrical communication component. In these embodiments, the moving portion of the joint 410 acts as a cam, and a pin located on the joint 410 acts as a cam follower. When the joint 410 moves in a first direction, the electrical communication component is pulled out of its channel 414 or housing, pulling the pin along with it. When the joint 410 moves in a second direction opposite of the first direction, the moving portion of the joint pushes the pin back into the electrical communication component thus forcing the component back into its housing or channel 414. These embodiments provide a low force upon the electrical communication component, with negligible resistance to joint motion compared to the use of an elastic element discussed above.

Figure 36:
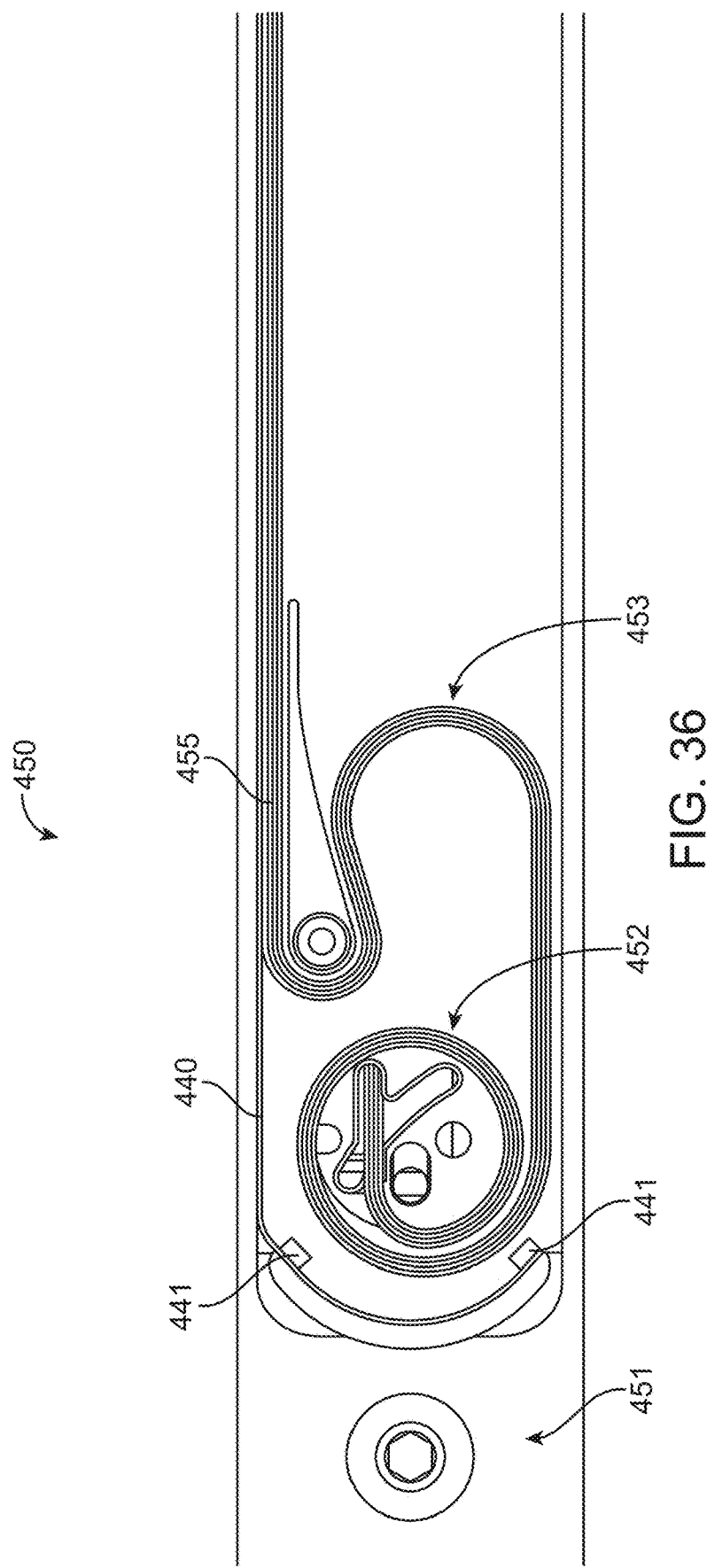
FIGS. 36 and 37 illustrate an electrical communication component and a retraction mechanism disposed around a joint, in accordance with some embodiments
Figure 37:
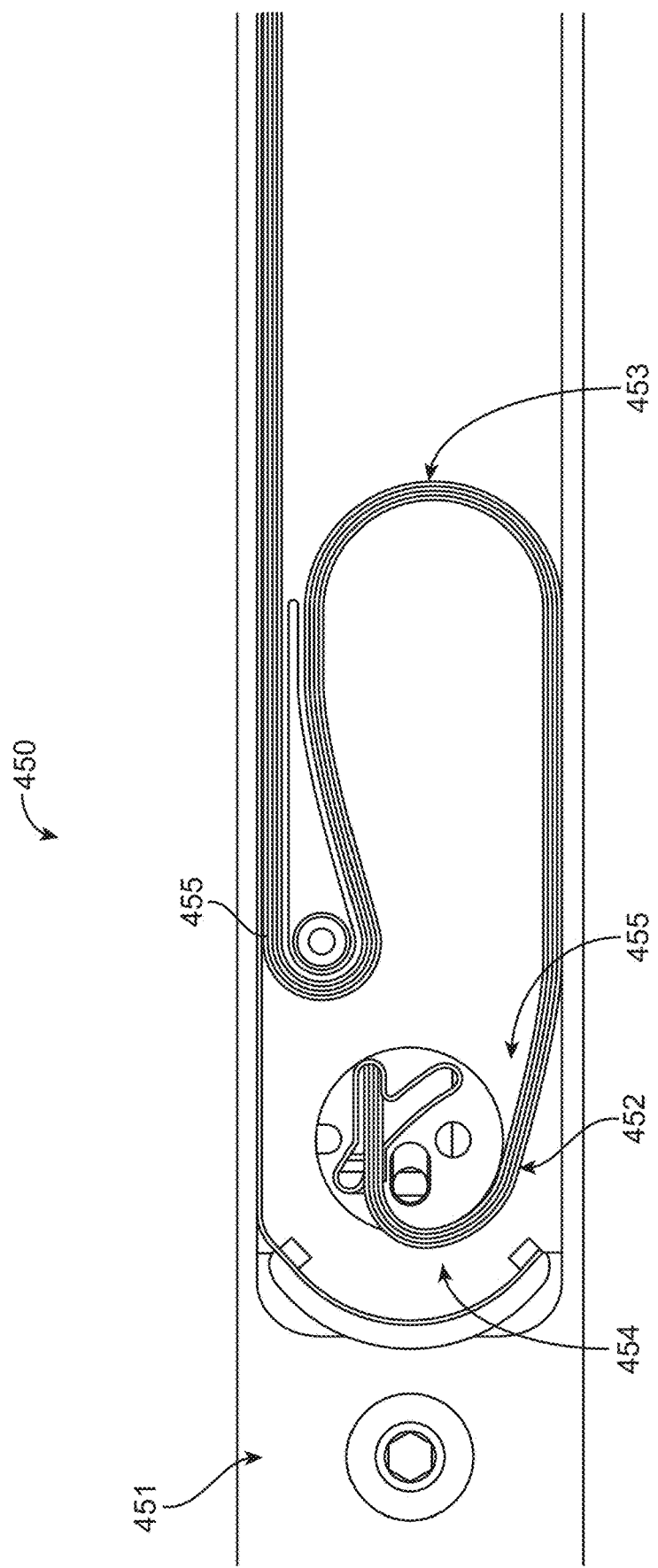

In some embodiments, both coils of electrical communication components and linear retraction mechanisms of electrical communication components are utilized. As illustrated in FIGS. 36-37, in some embodiments the electrical communication components may comprise an FPCB 440. One or more hall effect sensors 441 may be operatively coupled to the FPCB 440. FIGS. 36-37 show a camera device 450 where the primary joint is a rotary axis but due to the high range of motion, approximately 720 degrees, and the limited space around the joint, both rotary and linear mechanisms are utilized. The rotary and linear mechanisms may be disposed within a housing 451. In these embodiments, when the joint is at one extreme, the rotary portion (rotary coil 452) of the electrical communication component is wrapped tightly around the axis of the joint and the bend in the linear portion of the electrical communication component is close to the joint (FIG. 36). A constant force spring (not shown) is also wrapped around the axis of the joint, providing a force on the electrical communication component to prevent the electrical communication component from bowing out. The constant force spring ensures the wraps around the joint stay as small as possible to prevent the wraps from expanding unevenly. When the joint rotates to its other extreme, the coil 452 around the axis expands. Due to the limited radial space around and the constant force applied by the spring, the expanded portion of the coil 452 (coils on the moving bend 453) is pulled into the linear retraction section (away from the joint), thus preventing bowing out from occurring during expansion of the coil (FIG. 37).

To ensure the wraps around the joint stay as small as possible, according to some embodiments, the constant force spring is wrapped around the outer side 454 of the rotary coil 452 (see FIG. 37). In these embodiments, the constant force spring tightly compresses the rotary coil 452 against the joint when the rotary coil 452 is in the retracted state (as shown in FIG. 36). The length of the constant force spring can vary, depending on the length of the rotary coil 452 configured to be compressed against the joint. In some embodiments, the constant force spring is embedded within the rotary coil 452. In some embodiments, the constant force spring is attached to the inner side 455 of the rotary coil 452 (see FIG. 37). In these embodiments, the inner side of the constant force spring is wrapped around the joint in the retracted state (as shown in FIG. 36), and the outer side 454 of the spring is attached to the inner side 455 of the rotary coil 452. As the joint rotates to expand the rotary coil 452, the constant force spring is pulled away from the joint which would then cause the moving bend 453 to move away from the joint (FIG. 37). The rotary coil 452 may comprise a stationary portion 455.

Aspects of the subject matter described herein can be implemented in digital electronic circuitry, or in computer software, firmware, or hardware, including the structural means disclosed in this specification and structural equivalents thereof, or in combinations of them. Further, aspects of the subject matter described herein can be implemented using one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

It is contemplated that systems, devices, methods, and processes of the disclosure invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps.

It should be understood that the order of steps or order for performing certain action is immaterial so long as the disclosure remains operable. Moreover, two or more steps or actions may be conducted simultaneously.

It is to be understood that the disclosed subject matter may not be limited in its application to the details of construction and to the arrangements of the components set forth above or illustrated in the drawings. The disclosed subject matter may be capable of other embodiments and of being practiced and carried out in various ways. Also, it may be understood that the phraseology and terminology employed herein are for the purpose of description and should not be regarded as limiting. As such, those skilled in the art may appreciate that the conception, upon which this disclosure is based, may readily be utilized as a basis for the designing of other structures, methods, and systems for carrying out the several purposes of the disclosed subject matter.

Combination of Embodiments

Any embodiments as described herein can be utilized in combination with one another. For example, an arrangement of magnets and sensors of the magnetic sensing system can be utilized in combination with the wrapping or formation of a moving bend of the electrical communication components within a joint. For example, inclusion of a radial outward force by modifying a stiffness of a support tube coupled to a working end of the robotic system may be utilized in combination with a robotic arm having an elbow portion that movements independently from an end effector or point of origin, such as a shoulder.

EXAMPLES

The following illustrative examples are representative of embodiments of the stimulation, systems, and methods described herein and are not meant to be limiting in any way.

Example 1

A robotic assembly will comprise two robotic arms and a stereoscopic camera. The two robotic arms and camera will be individually coupled to a corresponding motor unit. There will be three motor units. Under working conditions, a working end of each of the two robotic arms and the camera will be inserted into a trocar for entry into a body cavity of a patient receiving a surgical procedure. The insertion of the three working ends will be sequential, such that the working end of the camera will be inserted first, followed by the working ends of each robotic arms. The working ends will each be coupled to the corresponding motor unit by a support tube that will carry one or more electrical components and one or more mechanical components. A stiffness of each support tube will create a force that will drive the working end radially outward upon exiting the trocar and will drive the portion of the support tube that remains within an inner lumen of the trocar against an inner wall of the trocar. Movement of the support tube against the inner wall will create sufficient cross-sectional area for the next working end to be inserted through the trocar. Each of the two robotic arms will comprise 3 rotary joints and 4 hinge joints. From origin to end effector, the order will be rotary joint, hinge joint, rotary joint, hinge joint, rotary joint, hinge joint, and hinge joint. This configuration of joints will permit each of the robotic arms to move with at least 8 degrees of freedom. An effective elbow joint of the robotic arm will move independently from the end effector and origin (shoulder). At least one joint of the robotic arm will comprise a magnetic sensing system for at least partially measuring joint displacement of the at least one joint. The magnetic sensing system will comprise an arrangement of 4 magnets and 4 sensors. The first and second magnet will be arranged in a first column and the third and fourth magnet will be arranged in a second column. The sensors will be positioned on a plane substantially perpendicular to the column of magnets. The magnets and sensors will be positioned substantially near a peripheral edge of the joint to permit centrally located space for other components of the robotic arm, such as cables. One of the joints of the robotic arm will comprise a length of cable wrapped around a shaft of the joint. The number of wraps of the cable will change as the joint moves, from tightly wrapped against the shaft to slack against a housing of the joint. Another joint of the robotic arm will comprise a length of cable formed into a moving bend. The moving bend will move during movement of the joint and the amount of the moving bend within a portion of the housing will change as the joint moves. The wrapping of cables and formation of the moving bend of cables will preserve the integrity of the cables and prevent damage to the cables while permitting sufficient movement of the joint.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

The invention claimed is:

1. A method for inserting a surgical robot through a trocar, the method comprising:
    (a) providing a first component of the surgical robot that is coupled at a proximal end of the first component to a support tube, wherein the first component comprises a camera or a robotic arm; and
    (b) inserting the first component and the support tube into the trocar, wherein as the first component exits the trocar, at least a portion of the support tube moves radially outward toward an inner wall of the trocar, thereby clearing a space within the trocar for passage of a second component of the surgical robot through the trocar.

2. The method of claim 1, wherein a transition element couples the support tube to the first component, and wherein the transition element is curved or tapered along at least a portion of its length.

3. The method of claim 2, wherein the transition element is configured to guide the first component radially outward upon the first component exiting the trocar.

4. The method of claim 1, wherein a stiffness of the support tube drives the support tube radially outward.

5. The method of claim 1, wherein the support tube is coupled to an elastic element, and wherein the elastic element drives the support tube radially outward.

6. The method of claim 5, wherein the elastic element comprises a spring.

7. The method of claim 1, wherein the inserting is performed by motor units coupled to the first component, and wherein the motor units are located outside of the trocar.

8. The method of claim 7, wherein the motor units comprise a mounting member configured to translate the motor units substantially parallel to an axis of insertion of the first component into the trocar.

9. The method of claim 7, wherein the first component is coupled to one of the motor units, and wherein the second component is coupled to another of the motor units.

10. The method of claim 1, wherein the support tube comprises a mechanical power element, an electrical power element, or a combination thereof.

11. The method of claim 1, wherein the support tube remains within the trocar throughout a surgical procedure carried out using the first component of the surgical robot.

12. The method of claim 1, wherein the first component comprises the robotic arm, and wherein the second component comprises a camera.

13. The method of claim 1, wherein at least a portion of the surgical robot is coupled to the trocar.

14. The method of claim 1, wherein a diameter of the support tube is less than a diameter of the first component.

15. A method for inserting a surgical robot through a trocar, the method comprising:
    (a) providing a first component of the surgical robot that is coupled at a proximal end of the first component to a support tube; and
    (b) inserting the first component and the support tube into the trocar, wherein as the first component exits the trocar, at least a portion of the support tube moves radially outward toward an inner wall of the trocar, thereby clearing a space within the trocar for passage of a second component of the surgical robot through the trocar, wherein a diameter of the trocar is too small to permit the trocar to enclose the first component and the second component simultaneously.

16. The method of claim 15, wherein the diameter of the trocar is sufficiently large to permit the trocar to enclose the support tube and the second component simultaneously.

17. The method of claim 1, further comprising positioning the first component relative to the second component once both the first component and the second component have exited the trocar.

18. The method of claim 15, wherein a transition element couples the support tube to the first component, and wherein the transition element is curved or tapered along at least a portion of its length.

19. The method of claim 18, wherein the transition element is configured to guide the first component radially outward upon the first component exiting the trocar.

20. The method of claim 15, wherein a stiffness of the support tube drives the support tube radially outward.

21. The method of claim 15, wherein the support tube is coupled to an elastic element, and wherein the elastic element drives the support tube radially outward.

22. The method of claim 15, wherein the inserting is performed by motor units coupled to the first component, and wherein the motor units are located outside of the trocar.

23. The method of claim 22, wherein the motor units comprise a mounting member configured to translate the motor units substantially parallel to an axis of insertion of the first component into the trocar.

24. The method of claim 22, wherein the first component is coupled to one of the motor units, and wherein the second component is coupled to another of the motor units.

25. The method of claim 15, wherein the support tube comprises a mechanical power element, an electrical power element, or a combination thereof.

26. The method of claim 15, wherein the support tube remains within the trocar throughout a surgical procedure carried out using the first component of the surgical robot.

27. The method of claim 15, wherein the first component comprises a robotic arm, and wherein the second component comprises a camera.

28. The method of claim 15, wherein at least a portion of the surgical robot is coupled to the trocar.

29. The method of claim 15, wherein a diameter of the support tube is less than a diameter of the first component.

30. The method of claim 15, further comprising positioning a first component relative to a second component once both the first component and the second component have exited the trocar.

* * * * *